(12) United States Patent
Qin et al.

(10) Patent No.: US 9,096,743 B2
(45) Date of Patent: Aug. 4, 2015

(54) PROCESS FOR FORMING FILMS, FIBERS, AND BEADS FROM CHITINOUS BIOMASS

(75) Inventors: Ying Qin, Tuscaloosa, AL (US); Robin D. Rogers, Tuscaloosa, AL (US); Daniel T. Daly, Tuscaloosa, AL (US)

(73) Assignee: The Board of Trustees of the University of Alabama, Tuscaloosa, AL (US)

( * ) Notice: Subject to any disclaimer, the term of this patent is extended or adjusted under 35 U.S.C. 154(b) by 558 days.

(21) Appl. No.: 13/375,245

(22) PCT Filed: Jun. 1, 2010

(86) PCT No.: PCT/US2010/036904
§ 371 (c)(1),
(2), (4) Date: Jan. 26, 2012

(87) PCT Pub. No.: WO2010/141470
PCT Pub. Date: Dec. 9, 2010

(65) Prior Publication Data
US 2012/0115729 A1    May 10, 2012

Related U.S. Application Data

(60) Provisional application No. 61/182,833, filed on Jun. 1, 2009.

(51) Int. Cl.
| | | |
|---|---|---|
| A61K 31/4164 | (2006.01) | |
| A61K 31/722 | (2006.01) | |
| C08K 5/3445 | (2006.01) | |
| C08L 5/08 | (2006.01) | |
| D01F 9/00 | (2006.01) | |
| A61K 8/49 | (2006.01) | |
| A61K 8/73 | (2006.01) | |
| D01F 1/10 | (2006.01) | |

(52) U.S. Cl.
CPC .............. C08L 5/08 (2013.01); A61K 8/4946 (2013.01); A61K 8/736 (2013.01); A61K 31/4164 (2013.01); A61K 31/722 (2013.01); C08K 5/3445 (2013.01); D01F 1/10 (2013.01); D01F 1/103 (2013.01); D01F 9/00 (2013.01)

(58) Field of Classification Search
CPC ........... C08K 5/3445; C08L 5/08; D01F 1/10; D01F 1/103; D01F 9/00; A61K 8/736; A61K 31/722; A61K 8/4946; A61K 31/4164
See application file for complete search history.

(56) References Cited

U.S. PATENT DOCUMENTS

| | | |
|---|---|---|
| 1,943,176 A | 1/1934 | Graenacher |
| 4,063,017 A | 12/1977 | Tsao et al. |
| 4,097,666 A | 6/1978 | Johnson et al. |
| 4,188,263 A | 2/1980 | Hulsmann et al. |
| 4,520,105 A | 5/1985 | Sinner et al. |
| 4,522,934 A | 6/1985 | Shum et al. |
| 4,970,156 A | 11/1990 | Avrameas et al. |
| 5,077,414 A | 12/1991 | Arduengo, III |
| 5,679,146 A | 10/1997 | Kalt et al. |
| 5,683,832 A | 11/1997 | Bonhote et al. |
| 5,714,536 A | 2/1998 | Ziolo et al. |
| 5,747,125 A | 5/1998 | Markulin |
| 5,792,399 A | 8/1998 | Meister et al. |
| 5,827,602 A | 10/1998 | Koch et al. |
| 5,836,970 A | 11/1998 | Pandit |
| 5,856,513 A | 1/1999 | Ue et al. |
| 6,376,712 B2 | 4/2002 | Narizuka et al. |
| 6,451,220 B1 | 9/2002 | Ziolo et al. |
| 6,613,310 B1 | 9/2003 | Campbell et al. |
| 6,808,557 B2 | 10/2004 | Holbrey et al. |
| 6,824,599 B2 | 11/2004 | Swatloski et al. |
| 7,198,695 B2 | 4/2007 | Kettenbach et al. |
| 7,253,289 B2 | 8/2007 | Ren et al. |
| 7,550,520 B2 | 6/2009 | Daly et al. |
| 8,030,030 B2 | 10/2011 | Varansi et al. |
| 8,038,840 B2 | 10/2011 | Li |
| 8,044,120 B2 | 10/2011 | D'Andola et al. |
| 8,110,667 B2 | 2/2012 | Zhang et al. |

(Continued)

FOREIGN PATENT DOCUMENTS

| | | |
|---|---|---|
| CA | 2479941 | 10/2003 |
| CH | 153446 | 6/1932 |

(Continued)

OTHER PUBLICATIONS

Hasegawa et al., New Pretreatment Methods Combining a Hot Water Treatment and Water/Acetone Extraction for Thermo-Chemical Conversion of Biomass, Energy and Fuels, 18:755-760 (2004).

Kenealy et al., Pretreatments for Converting Wood into Paper and Chemicals, Materials, Chemicals and Energy from Forest Biomass; Argyropoulos, D.; ACS Symposium Series; American Chemical Society, Washington, DC, chapter 25, pp. 392-408 (2007).

Office Action for U.S. Appl. No. 13/129,060 dated Apr. 8, 2013.

International Search Report and Written Opinion for Application No. PCT/US2010/055381 dated Aug. 2, 2011.

(Continued)

*Primary Examiner* — Abigail Fisher
(74) *Attorney, Agent, or Firm* — Meunier Carlin & Curfman LLC

(57) ABSTRACT

Disclosed is a process for forming films, fibers, and beads comprising a chitinous mass, for example, chitin, chitosan obtained from one or more biomasses. The disclosed process can be used to prepare films, fibers, and beads comprising only polymers, i.e., chitin, obtained from a suitable biomass, or the films, fibers, and beads can comprise a mixture of polymers obtained from a suitable biomass and a naturally occurring and/or synthetic polymer. Disclosed herein are the films, fibers, and beads obtained from the disclosed process. This Abstract is presented solely to aid in searching the subject matter disclosed herein and is not intended to define, limit, or otherwise provide the full scope of the disclosed subject matter.

25 Claims, 10 Drawing Sheets

(56) References Cited

U.S. PATENT DOCUMENTS

| | | |
|---|---|---|
| 8,182,557 B2 | 5/2012 | Argyropoulos |
| 2001/0024716 A1 | 9/2001 | Chen et al. |
| 2002/0010291 A1 | 1/2002 | Murphy |
| 2003/0059604 A1 | 3/2003 | Hattori et al. |
| 2003/0157351 A1 | 8/2003 | Swatloski et al. |
| 2003/0165445 A1 | 9/2003 | Malnou et al. |
| 2003/0233742 A1 | 12/2003 | Jones et al. |
| 2004/0038031 A1 | 2/2004 | Holbrey et al. |
| 2004/0077519 A1 | 4/2004 | Price et al. |
| 2005/0058694 A1 | 3/2005 | Nielsen |
| 2005/0061457 A1 | 3/2005 | Skuratowicz |
| 2005/0123851 A1 | 6/2005 | Shinbori et al. |
| 2005/0194561 A1 | 9/2005 | Davis |
| 2005/0196671 A1 | 9/2005 | Paonessa et al. |
| 2005/0285073 A1 | 12/2005 | Singh et al. |
| 2005/0288484 A1 | 12/2005 | Holbrey et al. |
| 2006/0118755 A1 | 6/2006 | Fujioka et al. |
| 2006/0128996 A1 | 6/2006 | Vaultier et al. |
| 2006/0194197 A1 | 8/2006 | Spangler et al. |
| 2006/0241287 A1* | 10/2006 | Hecht et al. ............ 530/356 |
| 2007/0006774 A1 | 1/2007 | Rogers et al. |
| 2007/0093462 A1 | 4/2007 | Rogers et al. |
| 2007/0112185 A1 | 5/2007 | Myllymaki |
| 2007/0215300 A1 | 9/2007 | Upfal et al. |
| 2007/0225191 A1 | 9/2007 | Scheibel et al. |
| 2008/0023162 A1 | 1/2008 | Myllymaki et al. |
| 2008/0097001 A1 | 4/2008 | Miraftab et al. |
| 2008/0190013 A1 | 8/2008 | Argyropoulos |
| 2008/0227162 A1 | 9/2008 | Varanasi et al. |
| 2008/0241536 A1 | 10/2008 | Luo et al. |
| 2009/0010983 A1 | 1/2009 | Melvik et al. |
| 2009/0088564 A1 | 4/2009 | Luo et al. |
| 2009/0099353 A1 | 4/2009 | Miraftab et al. |
| 2009/0215720 A1 | 8/2009 | Thibodeau et al. |
| 2010/0081798 A1 | 4/2010 | Balensiefer et al. |
| 2010/0087369 A1 | 4/2010 | Cutsem et al. |
| 2010/0112646 A1 | 5/2010 | Balensiefer et al. |
| 2010/0170504 A1 | 7/2010 | Zhang |
| 2010/0196967 A1 | 8/2010 | Edye et al. |
| 2010/0249432 A1 | 9/2010 | Siemer et al. |
| 2010/0287826 A1 | 11/2010 | Hoffman et al. |
| 2010/0319862 A1 | 12/2010 | Rahman |
| 2012/0245336 A1 | 9/2012 | Daly et al. |
| 2014/0027938 A1* | 1/2014 | Swatloski et al. ............ 264/10 |

FOREIGN PATENT DOCUMENTS

| | | |
|---|---|---|
| CN | 1380110 | 11/2002 |
| DE | 2703703 | 1/1977 |
| EP | 0780391 | 6/1997 |
| EP | 1222918 | 7/2002 |
| EP | 1854786 | 11/2007 |
| JP | 58183601 | 10/1983 |
| JP | 63056501 | 3/1988 |
| JP | 64017649 | 1/1989 |
| JP | 80089796 | 4/1996 |
| JP | 10265674 | 10/1998 |
| JP | 2002290011 | 10/2002 |
| JP | 2003171144 | 6/2003 |
| JP | 2003335887 | 11/2003 |
| WO | WO9420521 | 9/1994 |
| WO | WO9521871 | 8/1995 |
| WO | WO9606593 | 3/1996 |
| WO | WO0032658 | 6/2000 |
| WO | WO0181436 | 11/2001 |
| WO | WO02079269 | 10/2002 |
| WO | WO02100360 | 12/2002 |
| WO | WO02102586 | 12/2002 |
| WO | WO03029329 | 4/2003 |
| WO | WO03041692 | 5/2003 |
| WO | WO03074031 | 9/2003 |
| WO | WO2004027897 | 4/2004 |
| WO | WO2005017252 | 2/2005 |
| WO | 2006097571 A1 | 9/2006 |
| WO | 2006116126 A2 | 11/2006 |
| WO | WO2007005388 | 1/2007 |
| WO | WO2007063327 | 6/2007 |
| WO | WO2007111605 A1 | 10/2007 |
| WO | WO2009105236 | 8/2009 |
| WO | WO2010056790 | 5/2010 |

OTHER PUBLICATIONS

Deng et al., Phase Diagram of [Amim]CI + Salt Aqueous Biphasic Systems and Its Application for [Amim]CI Recovery, J. Chem. Eng. Data, 54:2470-2473 (2009).

Fukuyama et al., A Copper-Free Sonogashira Coupling Reaction in Ionic Liquids and Its Application to a Microflow System for Efficient Catalyst Recycling, Org. Lett.,4(10):1691-1694 (2002).

Gutowski et al., Controlling the Aqueous Miscibility of Ionic Liquids: Aqueous Biphasic Systems of Water-Miscible Ionic Liquids and Water-Structuring Salts for Recycle, Metathesis, and Separations, J. Am. Chem. Soc., 125:6632-6633 (2003).

Mathews et al., Palladium catalysed Suzuki cross-coupling reactions in ambient temperature ionic liquids, Chem. Commun., 1249-1250 (2000).

Qin et al., Dissolution or extraction of crustacean shells using ionic liquids to obtain high molecular weight purified chitin and direct production of chitin films and fibers, Green Chem., 12:968-971 (2010).

Remsing et al., Mechanism of cellulose dissolution in the ionic liquid 1-n-butyl-3-methylimidazolium chloride: a 13C and 35137CI NMR relaxation study on model systems, Chem. Commun., 1271-1273 (2006).

Scurto et al., Carbon dioxide induced separation of ionic liquids and water, Chem. Commun., 572-573 (2003).

Stepnowski, Solid-phase extraction of room-temperature imidazolium ionic liquids from aqueous environmental samples, Anal. Bioanal. Chem., 381:189-193 (2005).

Sun et al., Complete dissolution and partial delignification of wood in the ionic liquid 1-ethyl-3-methylimidazolium acetate, Green Chem., 11:646-655 (2009).

Vijayaraghavan et al., An Assessment on the Interaction of a Hydrophilic Ionic Liquid with Different Sorbents, Ind. Eng. Chem. Res., 48:7283-7288 (2009).

Wu et al., Do we understand the recyclability of ionic liquids?, Chem. Eur. J., 15:1804-1810 (2009).

Huddleston et al., Room Temperature Ionic Liquids as Novel Media for 'Clean' Liquid-Liquid Extraction, Chem. Commun., 1765-1766 (1998).

Husemann et al., Homogeneous Acetylation of Cellulose, Buletinul Institutului Politehnic Din Lasi, 1(1-2):47-51 (1970) (abstract).

Illanes et al., Immobilization of Lactase and Invertase on Crosslinked Chitin, in Bioreactor Immobilized Enzymes and Cells, Moo-Young, Ed., Elsevier Applied Science: London, 233-249 (1998).

Illanes, Stability of Biocatalysts, Elec. J. Biotechnol., 2(1):1-9 (1999).

International Search Report and Written Opinion for PCT/US2009/64105 issued Jan. 13, 2010.

International Search Report and Written Opinion for PCT/US2009/01066 issued Jun. 22, 2009.

International Search Report and Written Opinion for PCT/US2006/24863 issued Jan. 3, 2007.

International Search Report and Written Opinion for PCT/US2006/020941 issued Feb. 27, 2008.

International Search Report and Written Opinion for PCT/US2005/010235 issued Jan. 3, 2007.

Kilpeläinen et al., Dissolution of wood in ionic liquids, J. Agric. Food Chem., 55:9142-9148 (2007).

Kirk-Othmer, Encyclopedia of Chemical Technology, 4 Ed., 5:476-563 (1993).

Krajewska, Application of Chitin- and Chitosan-based Materials for Enzyme Immobilizations: A Review, Enz. Microb. Techno., 35:126-139 (2004).

Lau et al., Dissolution of Candida Antarctica Lipase B in Ionic Liquids: Effects on Structure and Activity, Green Chem., 6:483-487 (2004).

(56) References Cited

OTHER PUBLICATIONS

Lee et al., Ionic Liquid-Mediated Selective Extraction of Lignin from wood leading to enhanced enzymatic cellulose hydrolysis, Biotech. and Bioeng., 102(5):1368-1376 (2009).
Leipner et al., Structural Changes of Cellulose Dissolved in Molten Salt Hydrates, Macromol Chem Phys, 201 (15):2041-2049 (2000).
Liebert et al., Tailored Cellulose Esters: Synthesis and Structure Determination, Biomacromolecules, 6:333-340 (2005).
Linko et al., Cellulose Bead Entrapped Microbial Cells Biotechnical Applications, Enzyme Microb. Technol., 1:26-30 (1979).
Ma et al., Reverse Atom Transfer Radical Polymerization of Methyl Methacrylate in Room-Temperature Ionic Liquids, J. Polymer Sci. Pt. A-Polymer Chem., 41:143-151 (2003).
Maia et al., Cellulose Organic Solvents. 1. The Structure of Anhydrous N-Methylmorpholine N-Oxide and N-Methylmorphline N-Oxide Monohydrate, Acta Cryst., B37:1858-1862 (1981).
Mais et al., Modification of Cellulose Using Cellulose p-Toluene-Sulfonates as Intermediates, Zeszyty Naukowe Politechniki Slaskiej Chemm., 140:121-125 (1999).
Manangeeswaran et al., Degradation of indulin, a kraft pine lignin, by Serratia marcescens, J. Environ. Sci. Health, Part B: Pesticides, Food Contaminants, and Agricultural Wastes, 42(3):321-327 (2007).
Marson et al., A Novel, Efficient Procedure for Acylation of Cellulose Under Homogeneous Solution Conditions, J. Appl. Polymer Sci., 74:1355-1360 (1999).
Mazurkiewicz et al., Conducting Polymer Electrochemistry in Ionic Liquids, Synthetic Metals, 135:31-32 (2003).
Nara et al., Lipase-Catalysed Polyester Synthesis in 1-Butyl-3-Methylimidazolium Hexafluorophosphate Ionic Liquid, Tetrahedron Lett., 44:1371-1373 (2003).
Ngo et al., Thermal Properties of Imidazolium Ionic Liquids, Thermochimica Acta, 357-358:97-102 (2000).
Ohno et al., A New Type of Polymer Gel Electrolyte: Zwitterionic Liquid/Polar Polymer Mixture, Electrochimica Acta, 48:2079-2083 (2003).
Okamato et al., Synthesis, Spectra, and Reactions of N-Triphenylmethylpyridinium Salts. Reactions of Triphenylmethyl Chlordie with Pyridine Under High Pressure, J. Org. Chem., 35(11):3752-3756 (1970).
Padhye et al., Cellulose Degradation in Xanthate Process, J. App. Polymer Sci., 36:1475-1478 (1988).
Perrier et al., Reversible Addition—Fragmentation Chain Transfer Polymerization of Methacrylate, Acrylate and Styrene Monomers in 1-Alkyl-3-Methylimidazolium Hexfluorophosphate, European Polymer J., 39(3):417-422 (2003).
Pu et al., Ionic liquid as a green solvent for lignin, J. Wood Chem. Technol, 27:23-33 (2007).
Ren et al., Synthesis of 1-Allyl-3-Methylimidazolium-Based Room Temperature Ionic Liquid and Preliminary Study of its Dissolving Cellulose, Acta Polymerica Sinica, 3:448-451 (2003) (abstract).
Rogers et al., Ionic Liquids—Solvents of the Future?, Science, 302:792-793 (2003).
Sakai, Determination of Pore Size and Pore Size Distribution, J. Membr. Sci., 96:91-130 (1994).
Shriver et al., Inorganic Chemistry, W. H. Freeman & Co., New York, pp. 405-407 (1990).
Snedden et al., Cross-Linked Polymer-Ionic Liquid Composite Materials, Macromolecules, 36(12):4549-4556 (2003).
Stöllner et al., Activation of Cellulose Membranes with 1,1'-Carbonyldiimidazole or 1-Cyano-4-Dimethylaminopyridinium Tetrafluoroborate as a Basis for the Development of Immunosensors, Anal. Biochem., 304:157-165 (2002).
Suarez et al., Synthesis and Physical-Chemical Properties of Ionic Liquids Based on 1-n-Butyl-3-Methylimidazolium Cation, J. Chim. Phys., 95:1626-1639 (1998).
Sun et al., Magnetite-Embedded Cellulose Fibers Prepared From Ionic Liquid, J. Mat. Chem., 18:283-290 (2008).
Supplemental Search Report for EP4757863 issued May 12, 2009.
Swatloski et al., Dissolution of Cellulose with Ionic Liquids, J. Am. Chem. Soc., 124:4974-4975 (2002).
Swatloski et al., Ionic Liquids for the Dissolution and Regeneration of Cellulose, in Molten Salts XIII: Proceedings of the International Symposium, Trulove, P.C., DeLong, H.C., Mantz, R.A., Stafford, G.R., Matsunaga, M., Eds., The Electrochemical Society: Pennington, NJ, 19:155-164 (2002).
Tiller et al., A Novel Efficient Enzyme-Immobilization Reaction on NH2 Polymers by Means of L-Ascorbic Acid, Biotechnol. Appl. Biochem., 30:155-162 (1999).
Turner et al., Production of Bioactive Cellulose Films Reconstituted from Ionic Liquids, Biomacromolecules, 5:1379-1384 (2004).
Turner, Immobilization of Biocatalysts Using Novel IL-Reconstituted Cellulosic Support Materials, presentation on Apr. 19, 2005.
Visser et al., Task Specific Ionic Liquids for the Extraction of Metal Ions from Aqueous Solutions, Chem. Commun., 135-136 (2001).
Weckstrom et al., Entrapment of Whole Cell Yeast β-Galactosidase in Precipated Cellulose Derivatives, Food Process Eng., vol. 2, Applied Science Publishers Ltd., pp. 148-151 (1979).
Wilkes et al., Air and Water Stable 1-Ethyl-3-methylimidazolium Based Ionic Liquids, J. Chem. Soc. Chem. Commun., 13:965-967 (1992).
Willauer et al., Investigation of aqueous biphasic systems for the separation of lignins from cellulose in paper pulping process, J. Chromatogr. B: Biomed. Sci. Applic., 743(1-2):127-135 (2000).
Wu et al., Homogeneous Acetylation of Cellulose in a New Ionic Liquid, Biomacromol., 5:266-268 (2004).
Office Action for U.S. Appl. No. 12/735,827 dated Feb. 6, 2013.
Armstrong et al., Structure and properties of high stability geminal dicationic ionic liquids, J. Amer. Chem. Soc., 127(2):593-604 (2005).
Black et al., The estimation of chitin and chitin nitrogen in crawfish waste and derived products, Analyst, 75:185-189 (1950).
Brugnerotto et al., An infrared investigation in relation with chitin and chitosan characerization, Polymer, 42:3569-3580 (2001).
Holbrey et al., Mercury(II) partitioning from aqueous solutions with a new, hydrophobic ethylene-glycol functionalized bis-imidazolium ionic liquid, Green Chem., 5:129-135 (2003).
International Search Report and Written Opinion for PCT/US2010/036904 dated Jan. 3, 2011.
Kadokawa et al., A facile preparation of gel materials from a solution of cellulose in ionic liquid, Carbohydrate Research, 343:769-772 (2008).
Min et al., Chitin and chitosan nanofibers: electrospinning of chitin and deacetylation of chitin nanofibers, Polymer, 45:7137-7142 (2004).
Official Methods of Analysis of the Association of Official Analytical Chemists, 13a ed.; Horwitz, W. Ed.; AOAC International, Washington, DC, pp. 14-15 (1980).
Rødde et al., A Seasonal Study of the Chemical Composition and Chitin Quality of Shrimp Shells obtained from Northern Shrimp (*Pandalus borealis*), Carbohydrate Polymers, 71:388-393 (2008).
Sukhanova et al., Vysokomol. Soedin. Ser. B 31 (1989) 381; Chem. Abstr. 111(20):175985n.
Sun et al., Magnetite-embedded cellulose fibers from ionic liquid, J. Mater. Chem. 18:283-290 (2008).
Xie et al., Chitin and chitosan dissolved in ionic liquids as reversible sorbents of CO2, Green Chem., 8:630-633 (2006).
Wu et al., A novel biomass-ionic liquid platform for the utilization of native chitin, Polymer, 49:2321-2327 (2008).
Al-Adhami et al., Immobilization of Wood-Rotting Fungi Laccases on Modified Cellulose and Acrylic Carriers, J. Process Biochemistry, 37:1387-1394 (2002).
Ast et al., Efficient Assembly of Peptomers on Continous Surfaces, Tetrahedron Lett., 40:4317-4318 (1999).
Axegård, The Future Pulp Mill-A Biorefinery? Presentation at 1st International Biorefinery Workshop, Washington, DC., Jul. 20-21, 2005.
Benton et al., Effect of Room-Temperature Ionic Liquids as Replacements for Volatile Organic Solvents in Free-Radical Polymerization, Ionic Liquids, 818:125-133 (2002).
Biedron et al., Ionic Liquids as reaction Media for Polymeriazation Processes: Atom Transfer Radical Polymerization (ATRP) of Acrylates in Ionic Liquids, Polymer Int'l., 52(10):1584-1588 (2003).

(56) References Cited

OTHER PUBLICATIONS

Blankemeyer-Menge et al., Simultaneous Multiple Synthesis of Protected Peptide Fragments on 'Ally!'—Functionalized Cellulose Disc Supports, Tetrahedron Lett., 29:5871-5874 (1988).
Bonhôte et al., Hydrophobic, Highly Conductive Ambient-Temperature Molten Salts, Inorg. Chem., 35:1168-1178 (1996).
Bora et al., A Simple Method for Functionalization of Cellulose Membrane for Covalent Immoblization of Biomolecules, J. Membr. Sci., 250:215-222 (2005).
Cateto et al., Monitoring of lignin-based polyurethane synthesis by FTIR-ATR, Ind. Crops Prod., 27(2):168-174 (2008).
Chesney et al., Amino-Derivatised Beaded Cellulose Gels, Novel Accessible and Biodegradable Scavenger Resins for Solution Phase Cominatorial Synthesis, Green Chem., 2:57-62 (2000).
Earle et al., Ionic liquids. Green Solvents for the future, Pure Appl. Chem., 72(7):1391-1398 (2000).
El Seoud et al., Applications of ionic liquids in carbohydrate chemistry: A window of opportunities, Biomacromol, 8 (9):2629-2647 (2007).
Endres, Ionic Liquids: Solvents for the Electrodeposition of Metals and Semiconductors, Chem. Phys. Chem., 3 (2):144-154 (2002).
Fannin et al., Properties of 1,3-Dialkylimidazolium Chloride-Aluminum Choride Ionic Liquids. 2. Phase Transitions, Densities, Electrical Conductivities, and Viscosities, J. Phys. Chem., 88:2614-2621 (1984).
Fischer et al., Structural Changes of Cellulose Dissolved in Molten Salt Hydrates, 219th ACS National Meeting, San Francisco, CA (2000) (abstract).
Fort et al., Can ionic liquids dissolve wood? Processing and analysis of lignocellulosic materials with 1-n-butyl-3-methylimidazolium chloride, Green Chem., 9:63-69 (2007).
Froehner et al., Properties of the Glycoprotein Laccase Imobilised by Two Methods, Acta Chem Scand B, 29:691-694 (1975).
Fukaya et al., Cellulose dissolution with polar ionic liquids under mild conditions: required factors for anions, Green Chem., 10:44-46 (2008).
Gallezot, Process options for converting renewable feedstocks to bioproducts, Green Chem., 9:295-302 (2007).
Gelbrich, Colloidal Structures Based on Topochemically Modified Cellulose, Papier (Heidelberg), 52:755-758 (1998).
Gemeiner, Immobilized Enzymes, Organelles and Cells, in Enzyme Engineering, Gemeiner, Ed., Ellis Horwood Series in Biochemistry and Biotechnology, Ellis Horwood Limited: West Sussex, England, pp. 158-179 (1992).
Gordon et al., Fused Organic Salts. 8. Properties of Molten Straight-Chain Isomers of Tetra-n-Pentylammonium Salts, J. Amer. Chem. Soc., 100(24):7445-7454 (1978).
Harkin et al., Lignification in Trees: Indication of Exclusive Peroxidase Participation, Science, 180:296-98 (1973).
Heinze et al., Unconventional Methods in Cellulose Functionalization, Prog. Polym. Sci., 26:1689-1762 (2001).
Hirayama, Rapid Confirmation and Revision of the Primary Structure of Bovine Serum Albumin by ESIMS and Frit-FAB LC/MS, Biochem. Biophys. Comm., 173:639-646 (1990).
Holbrey et al., The Phase Behaviour of 1-Alkyl-3-Methlimidazolium Tetrafluoroborates; Ionic Liquids and Ionic Liquid Crystals, J. Chem. Soc. Dalton Trans., 2133-2139 (1999).
Huddleston et al., Characterization and Comparison of Hydrophilic and Hydrophobic Room Temperature Ionic Liquids Incorporating the Imidazolium Cation, Green Chem, 3:156-164 (2001).
Yamazaki et al., An acidic cellulose-chitin hybrid gel as novel electrolyte for an electric double layer capacitor, Electrochem. Commun., 11:68-70, 2009.
International Search Report and Written Opinion, dated Aug. 27, 2014, received in connection with International Application No. PCT/US2014/034793.

\* cited by examiner

PROCESS FOR FORMING FILMS, FIBERS, AND BEADS FROM CHITINOUS BIOMASS

CROSS REFERENCE TO RELATED APPLICATIONS

This application claims the benefit of priority to U.S. Provisional Application No. 61/182,833, filed Jun. 1, 2009, which is incorporated by reference herein in its entirety.

FIELD OF THE DISCLOSURE

Disclosed herein is a process for forming films, fibers, and beads comprising a chitinous mass, for example, chitin and chitosan obtained from one or more biomasses. The disclosed process can be used to prepare films, fibers, and beads comprising only polymers, e.g., chitin, obtained from a suitable biomass, or the films, fibers, and beads can comprise a mixture of polymers obtained from a suitable biomass and a naturally occurring and/or synthetic polymer. Also, disclosed herein are the films, fibers, and beads obtained from the disclosed process.

BACKGROUND

Each year humans place an increasingly greater demand on the biosphere. The world's increasing level of industrialization has come to produce a surge in the consumption of natural resources, while at the same time producing an equally large amount of waste material that is either non-recyclable or simply not recycled. The replacement of metals by plastics in the last century somewhat abated the growth in the demand for this resource commodity. But with the rise in synthetic polymer technology, came an explosion in the use of synthetic polymers with the result that today plastics and other synthetic polymers are the most utilized category of non-naturally occurring materials.

Polymers, however, are ubiquitous in nature. These natural building blocks have been used by mankind since antiquity, for example, fibers made of hemp, cotton, wool, and silk are all a part of human development. Processes directed to the manufacture of articles comprising recyclable plant polymers such as cellulose, are well known and have been under development for many centuries. Less well studied are processes that utilize natural polymers derived from non-plant sources, i.e., the hard outer shells of marine animals.

Chitin is the most abundant polymer in the marine environment. Chitin is the main component of the exoskeletons of arthropods, such as crustaceans and in the cell walls of fungi. It has been a major source of surface pollution in coastal areas. Both chitin and its major derivative chitosan (obtained by deacetylation of chitin) have numerous applications. The bioactivity, biocompatibility, and low toxicity of native or chemically-modified chitin and chitosan make them suitable for controlled drug release, cosmetics, food preservation, fertilizer, or biodegradable packaging materials, or waste water processing and other industrial applications. Chitin, however, is highly hydrophobic and is insoluble in water and most organic solvents due to the high density of hydrogen bonds of the adjacent chains in solid state. The difficulty in the dissolution restricts the use of chitin as a replacement for synthetic polymers.

Crustacean shells are currently the major source of chitin available for industrial processing. The best characterized sources of chitin are shellfish (including shrimp, crab, lobster, and krill), oyster, and squids. Annual synthesis of chitin in freshwater and marine ecosystem is about 600 and 1600 million tons, respectively. Producing chitin in industry is primarily from the exoskeletons of marine crustacean shell waste by a chemical method that involves acid demineralization, alkali deproteinization, and followed by decolorization. Even though the current industrialized chemical process isolates chitin from crustacean shells efficiently, disadvantages exist in these procedures, including, inter alia, the use of corrosive acids, bases, and strong oxidants which are not environmentally friendly. In addition, these processes can modify or nullify the desired physiochemical properties of chitin, for example, by acid demineralization, shorting the chitin chain length, as well as, degrading the chitin during deproteinization in hot alkali solutions. These undesired changes in the properties of chitin can have a profound affect when the chitin obtained therefrom must have specific molecular weight distributions and degrees of acetylation (DA).

As such, there is a long felt need for films, fibers, and beads formed from chitin wherein the chitin has both consistent, as well as, desirable properties. There is also a need for chitin compositions that can be efficiently and reproducibly manufactured under environmentally friendly and mild conditions. Disclosed herein are processes and compositions that address these and other needs.

SUMMARY OF THE DISCLOSURE

The present disclosure relates to processes for forming films, fibers, and beads from a chitinous biomass. In one aspect, chitin can be directly extracted from a chitinous biomass, for example, from shrimp or crab shells and directly used to form fibers, films, and beads which comprise chitin having a higher molecular weight than chitin derived from practical grade or pure grade sources. In another aspect, an ionic liquid can be used to dissolve a source of chitin in the first step of the process. In a further aspect, a combination of an ionic liquid and a co-solvent, for example, DMSO, can be used to dissolve a source of chitin in the first step of the process. In a yet further aspect, an organic solvent, for example, DMSO, can be used to dissolve a source of chitin in the first step of the process. In a still further aspect, the purified chitinous biomass can be combined with a naturally occurring or synthetic polymer, inter alia, cellulose, poly(2-hydroxyethyl methacrylate (PHEMA), to form composite films, fibers, and beads.

Additional advantages of the disclosed process will be set forth in part in the description which follows, and in part will be obvious from the description, or can be learned by practice of the disclosed process. The advantages of the disclosed process will be realized and attained by means of the elements and combinations particularly pointed out in the appended claims. It is to be understood that both the foregoing general description and the following detailed description are exemplary and explanatory only and are not restrictive of the disclosed process, as claimed.

DETAILED DISCLOSURE

Figure 1:
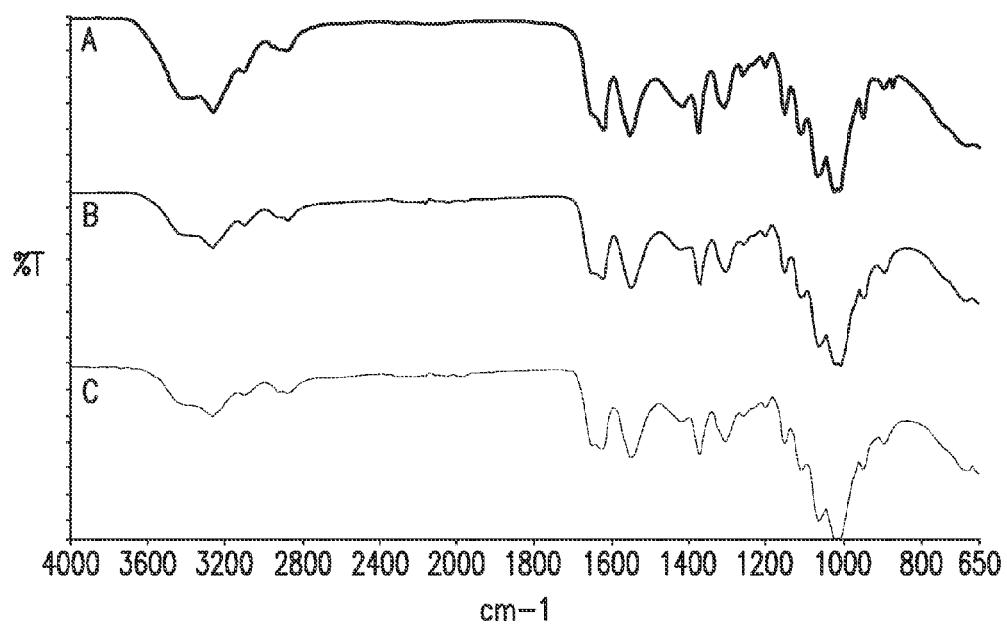
FIG. 1 is the IR spectra of polymer films prepared by the disclosed process. Spectrum 1A depicts the IR spectrum of a polymer film comprising chitin derived from shrimp shells according to Example 1. Spectrum 1B depicts the IR spectrum of a polymer film comprising practical grade chitin according to Example 2. Spectrum 1C depicts the IR spectrum of a polymer film comprising practical grade chitin according to Example 3.

The materials, compounds, compositions, articles, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and, unless a particular term is specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ionic liquid" includes mixtures of two or more such ionic liquids, reference to "the compound" includes mixtures of two or more such compounds, and the like. "Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "dissolving or dispersing" means contacting a source of a chitinous biomass with an ionic liquid, an organic solvent, or mixture thereof to solublize the chitan, chitosan, or other polysaccharide materials present in the biomass. Depending upon the relative purity of the biomass, some of the material present, especially impurities, will not dissolve and it is this undissolved material that is removed from the solublized biomass. As such, relatively pure grades of the biomass, for example, pure or practical grade chitin, will be completely "dissolved," whereas dried, ground biomass, for example, shrimp or crab shells will be "dispersed" with the effect that the chitin will be solublized and the impurities will not be.

As used herein, the term "chitinous biomass" means any source of chitin, chitosan, or other polysaccharide derived from a marine exoskeleton (e.g., the shells of crustaceans like shrimp, crab, lobster, crawfish, prawns, etc.). Chitosan is typically deacetylated chitin.

As used herein, the term "chitosan" means deacetylated chitin or any other form of chemically modified chitin.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both (e.g., zwitterions) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, etc.

The term "anion" is a type of ion and is included within the meaning of the term "ion". An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion". A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$D^1$," "$D^2$," "$D^3$," and "$D^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as -$OD^1$ where $D^1$ is alkyl as defined above.

The term "alkenyl" as used herein is a hydrocarbon group of from 2 to 24 carbon atoms with a structural formula containing at least one carbon-carbon double bond. Asymmetric structures such as $(D^1D^2)C{=}C(D^3D^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $ND^1D^2D^3$, where $D^1$, $D^2$, and $D^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)$D^1$ or —C(O)O$D^1$, where $D^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $D^1OD^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $D^1C(O)D^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiD^1D^2D^3$, where $D^1$, $D^2$, and $D^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfo-oxo" as used herein is represented by the formulas —S(O)$D^1$, —S(O)$_2D^1$, —OS(O)$_2D^1$, or —OS(O)$_2$O$D^1$, where $D^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above. Throughout this specification "S(O)" is a short hand notation for S=O.

The term "sulfonyl" is used herein to refer to the sulfo-oxo group represented by the formula —S(O)$_2D^1$, where $D^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "sulfone" as used herein is represented by the formula $D^1S(O)_2D^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfoxide" as used herein is represented by the formula $D^1S(O)D^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The world market for chitin-based materials exceeded $2 billion annually in the year 2005. Analysts also predict that markets for these materials are likely to grow rapidly over the next ten years. Chitin has been known to form microfibrillar arrangements in living organisms. The presence of microfibrils suggests that chitin has characteristics which make it a good candidate for fiber spinning. To spin chitin fibers, the raw polymer must be suitably redissolved after removal of extraneous material such as calcium carbonate and proteins, which encase the microfibrils, indicating the purification and complete dissolution of chitin are key steps in chitin fiber making. As such, the following is a disclosure of a process for forming chitin-based films, fibers, and beads.

The following are non-limiting examples of aspects, iterations, and examples of the disclosed process. The following are not meant to be limiting in scope, but to provide an overview of the process and the combinations of steps that can comprise the disclosed process.

Chitin derived from crustaceans is available from suppliers as "pure chitin" and as "practical grade chitin." These forms of chitin undergo a process similar to the Kraft Process for obtaining cellulose from wood or other sources of cellulose. During the process of preparing pure chitin and practical grade chitin, there is a break down of the polysaccharide chains such that the resulting chitin has a shorter chain length and therefore a lower average molecular weight than it had before it was processed. The disclosed processes provide a method of directly extracting chitin from a chitinous biomass without substantially shortening the polysaccharide chains. As such, the films, fibers, and beads formed from the disclosed process wherein the chitin is directly extracted from the chitinous biomass provides the first method for obtaining polymeric materials comprising chitin that has the original full polysaccharide chain length (and molecular weight). Moreover the disclosed chitin can be substantially free of agents that are typically found in pure and practical grade chitin, such as methanesulfonic acid, trichloroacetic acid, dichloroacetic acid, formic acid, and dimethylacetamide.

Direct Extraction of Chitin from a Biomass

In one embodiment, the disclosed process, wherein chitin is extracted directly from a chitinous biomass, can comprise:
a) contacting an ionic liquid with a chitinous biomass to form a residue and a chitin comprising solution; and
b) adding a coagulant to the solution formed in step (a) and casting the chitin comprising solution into a film, a fiber, or a bead.

In a further embodiment, the process wherein chitin is extracted directly from a chitinous biomass, can comprise:
a) contacting an ionic liquid with a chitinous biomass to form a residue and a chitin comprising solution;
b) adding an adjunct ingredient to the chitin comprising solution; and
c) adding a coagulant to the solution formed in step (a) and casting the chitin comprising solution into a film, a fiber, or a bead.

However, this process can be used to prepare high molecular weight chitin, by:
a) contacting an ionic liquid with a chitinous biomass to form a residue and a chitin comprising solution;
b) separating the chitin comprising solution from the residue; and
c) adding a coagulant to the solution that is separated in step (b) to form a high molecular weight regenerated chitin.

These processes can also be performed using pure chitin and practical grade chitin. However, because of the commercial processing used to provide pure chitin and practical grade chitin, the chitin in these sources has a lower molecular weight than it had prior to processing (i.e., in the unprocessed chitinous biomass). Consequently, the regenerated chitin obtained when using the disclosed processes with these sources of chitin will likewise be of lower molecular weight than had the disclosed processes been followed with unprocessed chitinous biomass.

Ionic Liquids Used for the Dissolution of the Source of Chitin

One aspect of the present disclosure relates to a process for preparing chitin films, fibers, or beads comprising:
a) dissolving or dispersing a source of chitin in an ionic liquid to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

One iteration of this aspect of the disclosed process relates to a process for preparing chitin films, fibers, or beads and comprises:
a) dissolving or dispersing a source of chitin in an ionic liquid at a temperature of from about 70° C. to about 130° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

One example of this iteration relates to a process for preparing chitin films, fibers, or beads, and comprises:
a) dissolving or dispersing a source of chitin in an ionic liquid at a temperature of from about 90° C. to about 110° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

Another example of this iteration relates to a process for preparing chitin films, fibers, or beads, and comprises:
a) dissolving or dispersing a source of chitin in an ionic liquid at a temperature of about 100° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

Another iteration of this aspect of the disclosed process relates to a process for preparing chitin films, fibers, or beads, and comprises:
a) dissolving or dispersing a source of chitin in an ionic liquid to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of from about 70° C. to about 130° C.; and
f) adding a coagulant and casting the regenerated chitin from step (e) into a film, a fiber, or a bead.

One example of this iteration relates to a process for preparing chitin films, fibers, or beads, and comprises:
a) dissolving or dispersing a source of chitin in an ionic liquid to form a first solution;
b) separating the undissolved material to form a second solution;

c) adding a coagulant to the second solution to form regenerated chitin;
d) isolating the regenerated chitin;
e) dissolving the regenerated chitin in an ionic liquid at a temperature of from about 90° C. to about 110° C.; and
f) adding a coagulant and casting the regenerated chitin from step (e) into a film, a fiber, or a bead.

Another example of this iteration relates to a process for preparing chitin films, fibers, or beads, and comprises:
a) dissolving or dispersing a source of chitin in an ionic liquid to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of about 100° C.; and
f) adding a coagulant and casting the regenerated chitin from step (e) into a film, a fiber, or a bead.

Another iteration of this aspect of the disclosed process relates to a process for preparing chitin films, fibers, or beads and comprises:
a) dissolving or dispersing a source of chitin in an ionic liquid at a temperature of from about 70° C. to about 130° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of from about 70° C. to about 130° C.; and
f) adding a coagulant and casting the regenerated chitin from step (e) into a film, a fiber, or a bead.

One example of this iteration relates to a process for preparing chitin films, fibers, or beads and comprises:
a) dissolving or dispersing a source of chitin in an ionic liquid at a temperature of from about 90° C. to about 110° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of from about 90° C. to about 110° C.; and
f) adding a coagulant and casting the regenerated chitin from step (e) into a film, a fiber, or a bead.

Another example of this iteration relates to a process for preparing chitin films, fibers, or beads and comprises:
a) dissolving or dispersing a source of chitin in an ionic liquid at a temperature of about 100° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of about 100° C.; and
f) adding a coagulant and casting the regenerated chitin from step (e) into a film, a fiber, or a bead.

A further iteration of this aspect of the disclosed process relates to a process for preparing chitin films, fibers, or beads and comprises:

a) dissolving or dispersing a source of chitin in 3-ethyl-1-methyl-1H-imidazol-3-ium acetate, [C$_2$mim]OAc, having the formulae:

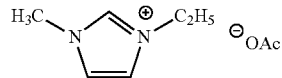

at a temperature of from about 70° C. to about 130° C. to form a first solution;
b) separating the undissolved material to form a second solution;
c) adding a coagulant to the second solution to form regenerated chitin;
d) isolating the regenerated chitin;
e) dissolving the regenerated chitin in 3-ethyl-1-methyl-1H-imidazol-3-ium acetate, [C$_2$mim]OAc, having the formulae:

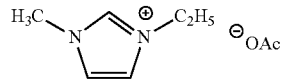

at a temperature of from about 70° C. to about 130° C.; and
f) adding a coagulant and casting the regenerated chitin from step (e) into a film, a fiber, or a bead.

One example of this iteration relates to a process for preparing chitin films, fibers, or beads and comprises:
a) dissolving or dispersing a source of chitin in 3-ethyl-1-methyl-1H-imidazol-3-ium acetate, [C$_2$mim]OAc, having the formulae:

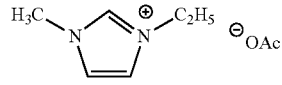

at a temperature of from about 90° C. to about 110° C. to form a first solution;
b) separating the undissolved material to form a second solution;
c) adding a coagulant to the second solution to form regenerated chitin;
d) isolating the regenerated chitin;
e) dissolving the regenerated chitin in 3-ethyl-1-methyl-1H-imidazol-3-ium acetate, [C$_2$mim]OAc, having the formulae:

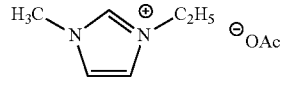

at a temperature of from about 90° C. to about 110° C.; and
f) adding a coagulant and casting the regenerated chitin from step (e) into a film, a fiber, or a bead.

Another example of this iteration relates to a process for preparing chitin films, fibers, or beads and comprises:
a) dissolving or dispersing a source of chitin in 3-ethyl-1-methyl-1H-imidazol-3-ium acetate, [C$_2$mim]OAc, having the formulae:

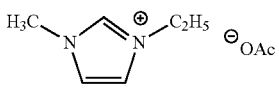

at a temperature of about 100° C. to form a first solution;
b) separating the undissolved material to form a second solution;
c) adding a coagulant to the second solution to form regenerated chitin;
d) isolating the regenerated chitin;
e) dissolving the regenerated chitin in 3-ethyl-1-methyl-1H-imidazol-3-ium acetate, [C₂mim]OAc, having the formulae:

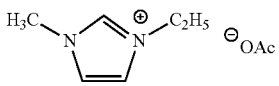

at a temperature of about 100° C.; and
f) adding a coagulant and casting the regenerated chitin from step (e) into a film, a fiber, or a bead.

A further aspect of the present disclosure relates to a process for preparing chitin films, fibers, or beads and comprises:
a) dissolving or dispersing a source of chitin in an ionic liquid to form a first solution;
b) separating the undissolved material to form a second solution;
c) adding a coagulant to the second solution to form regenerated chitin;
d) isolating the regenerated chitin;
e) dissolving the regenerated chitin in an ionic liquid to form a solution;
f) adding an adjunct ingredient to the solution formed in step (e) to form a chitin/adjunct ingredient admixture solution; and
g) adding a coagulant to the solution of step (f) and casting the regenerated chitin/adjunct ingredient admixture into a film, a fiber, or a bead.

It is noted that while the above examples disclose the ionic liquid [C₂mim]OAc, the disclosed processes can use other ionic liquids, for example, [C$_n$mim]RCO₂, where n is an integer of from 1 to 8 and R is H or substituted or unsubstituted C$_{1-8}$ alkyl.

Co-solvent Used for Dissolution of the Source of Chitin

Another aspect of the present disclosure relates to a process for preparing chitin films, fibers, or beads and comprises:
a) dissolving or dispersing a source of chitin in an ionic liquid and a co-solvent to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

One iteration of this aspect of the disclosed process relates to a process for preparing chitin films, fibers, or beads and comprises:
a) dissolving or dispersing a source of chitin in an ionic liquid and a co-solvent at a temperature of from about 70° C. to about 130° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

One example of this iteration relates to a process for preparing chitin films, fibers, or beads and comprises:
a) dissolving or dispersing a source of chitin in an ionic liquid and a co-solvent at a temperature of from about 90° C. to about 110° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

Another example of this iteration relates to a process for preparing chitin films, fibers, or beads and comprises:
a) dissolving or dispersing a source of chitin in an ionic liquid and a co-solvent at a temperature of about 100° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid; and
f) adding a coagulant and casting the regenerated chitin from step (e) into a film, a fiber, or a bead.

Another iteration of this aspect of the disclosed process relates to a process for preparing chitin films, fibers, or beads and comprises:
a) dissolving or dispersing a source of chitin in an ionic liquid and a co-solvent to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of from about 70° C. to about 130° C.; and
f) adding a coagulant and casting the regenerated chitin from step (e) into a film, a fiber, or a bead.

One example of this iteration relates to a process for preparing chitin films, fibers, or beads and comprises:
a) dissolving or dispersing a source of chitin in an ionic liquid and a co-solvent to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of from about 90° C. to about 110° C.; and
f) adding a coagulant and casting the regenerated chitin from step (e) into a film, a fiber, or a bead.

Another example of this iteration relates to a process for preparing chitin films, fibers, or beads and comprises:
a) dissolving or dispersing a source of chitin in an ionic liquid and a co-solvent to form a first solution;
b) separating the undissolved material to form a second solution;
c) adding a coagulant to the second solution to form regenerated chitin;

d) isolating the regenerated chitin;
e) dissolving the regenerated chitin in an ionic liquid at a temperature of about 100° C.; and
f) adding a coagulant and casting the regenerated chitin from step (e) into a film, a fiber, or a bead.

Another iteration of this aspect of the disclosed process relates to a process for preparing chitin films, fibers, or beads and comprises:
a) dissolving or dispersing a source of chitin in an ionic liquid and a co-solvent at a temperature of from about 70° C. to about 130° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of from about 70° C. to about 130° C.; and
f) adding a coagulant and casting the regenerated chitin from step (e) into a film, a fiber, or a bead.

One example of this iteration relates to a process for preparing chitin films, fibers, or beads and comprises:
a) dissolving or dispersing a source of chitin in an ionic liquid and a co-solvent at a temperature of from about 90° C. to about 110° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of from about 90° C. to about 110° C.; and
f) adding a coagulant and casting the regenerated chitin from step (e) into a film, a fiber, or a bead.

Another example of this iteration relates to a process for preparing chitin films, fibers, or beads and comprises:
a) dissolving or dispersing a source of chitin in an ionic liquid and a co-solvent at a temperature of about 100° C. to form a first solution;
b) separating the undissolved material to form a second solution;
c) adding a coagulant to the second solution to form regenerated chitin;
d) isolating the regenerated chitin;
e) dissolving the regenerated chitin in an ionic liquid at a temperature of about 100° C.; and
f) adding a coagulant and casting the regenerated chitin from step (e) into a film, a fiber, or a bead.

A further iteration of this aspect of the disclosed process relates to a process for preparing chitin films, fibers, or beads and comprises:
a) dissolving or dispersing a source of chitin in 3-ethyl-1-methyl-1H-imidazol-3-ium acetate, [C$_2$mim]OAc, having the formulae:

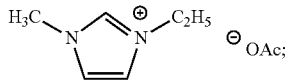

and
dimethylsulfoxide at a temperature of from about 70° C. to about 130° C. to form a first solution;
b) separating the undissolved material to form a second solution;
c) adding a coagulant to the second solution to form regenerated chitin;
d) isolating the regenerated chitin;
e) dissolving the regenerated chitin in 3-ethyl-1-methyl-1H-imidazol-3-ium acetate, [C$_2$mim]OAc, having the formulae:

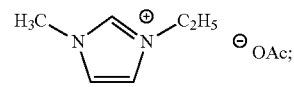

and
dimethylsulfoxide at a temperature of from about 70° C. to about 130° C.; and
f) adding a coagulant and casting the regenerated chitin from step (e) into a film, a fiber, or a bead.

Another example of this iteration relates to a process for preparing chitin films, fibers, or beads and comprises:
a) dissolving or dispersing a source of chitin in 3-ethyl-1-methyl-1H-imidazol-3-ium acetate, [C$_2$mim]OAc, having the formulae:

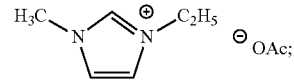

and
dimethylsulfoxide at a temperature of about 100° C. to form a first solution;
b) separating the undissolved material to form a second solution;
c) adding a coagulant to the second solution to form regenerated chitin;
d) isolating the regenerated chitin;
e) dissolving the regenerated chitin in 3-ethyl-1-methyl-1H-imidazol-3-ium acetate, [C$_2$mim]OAc, having the formulae:

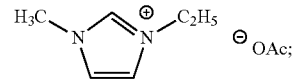

and
dimethylsulfoxide at a temperature of about 100° C.; and
f) adding a coagulant and casting the regenerated chitin from step (e) into a film, a fiber, or a bead.

A further aspect of the present disclosure relates to a process for preparing chitin films, fibers, or beads and comprises:
a) dissolving or dispersing a source of chitin in an ionic liquid and a co-solvent to form a first solution;
b) separating the undissolved material to form a second solution;
c) adding a coagulant to the second solution to form regenerated chitin;
d) isolating the regenerated chitin;
e) dissolving the regenerated chitin in an ionic liquid to form a solution;
f) adding an adjunct ingredient to the solution formed in step (e) to form a chitin/adjunct ingredient admixture solution; and
g) adding a coagulant to the solution of step (f) and casting the regenerated chitin/adjunct ingredient admixture into a film, a fiber, or a bead.

It is noted that while the above examples disclose the ionic liquid [C$_2$mim]OAc, the disclosed processes can use other ionic liquids, for example, [C$_n$mim]RCO$_2$, where n is an integer of from 1 to 8 and R is H or substituted or unsubstituted C$_{1-8}$ alkyl.

Organic Solvent Used for Dissolution of the Source of Chitin

Another aspect of the present disclosure relates to a process for preparing chitin films, fibers, or beads and comprises:
 a) dissolving or dispersing a source of chitin in an ionic liquid, a co-solvent, or a mixture of an ionic liquid and an organic solvent to form a first solution;
 b) separating the undissolved material to form a second solution;
 c) adding a coagulant to the second solution to form regenerated chitin;
 d) isolating the regenerated chitin;
 e) dissolving the regenerated chitin in an ionic liquid to form a solution;
 f) dissolving one or more polymers in an ionic liquid to form a solution;
 g) combining the solution from step (e) and step (f) to form an polymer admixture solution; and
 h) adding a coagulant to the polymer admixture solution of step (g) and casting the polymer admixture from step (g) into a film, a fiber, or a bead.

One iteration of this aspect of the disclosed process relates to a process for preparing chitin films, fibers, or beads and comprises:
 a) dissolving or dispersing a source of chitin in an ionic liquid, a co-solvent, or a mixture of an ionic liquid and an organic solvent to form a first solution;
 b) separating the undissolved material to form a second solution;
 c) adding a coagulant to the second solution to form regenerated chitin;
 d) isolating the regenerated chitin;
 e) dissolving the regenerated chitin in an ionic liquid to form a solution;
 f) dissolving cellulose in an ionic liquid to form a solution;
 g) combining the solution from step (e) and step (f) to form an polymer admixture solution; and
 h) adding a coagulant to the polymer admixture solution of step (g) and casting the polymer admixture from step (g) into a film, a fiber, or a bead.

Another iteration relates to a process for preparing chitin films, fibers, or beads, and comprises:
 a) dissolving or dispersing a source of chitin in an ionic liquid, a co-solvent, or a mixture of an ionic liquid and an organic solvent to form a first solution;
 b) separating the undissolved material to form a second solution;
 c) adding a coagulant to the second solution to form regenerated chitin;
 d) isolating the regenerated chitin;
 e) dissolving the regenerated chitin in an ionic liquid to form a solution;
 f) dissolving poly(2-hydroxyethyl methacrylate) (PHEMA) in an ionic liquid to form a solution;
 g) combining the solution from step (e) and step (f) to form an polymer admixture solution; and
 h) adding a coagulant to the polymer admixture solution of step (g) and casting the polymer admixture from step (g) into a film, a fiber, or a bead.

A further aspect of the present disclosure relates to a process for preparing chitin films, fibers, or beads and comprises:
 a) dissolving or dispersing a source of chitin in an ionic liquid, a co-solvent, or a mixture of an ionic liquid and an organic solvent to form a first solution;
 b) separating the undissolved material to form a second solution;
 c) adding a coagulant to the second solution to form regenerated chitin;
 d) isolating the regenerated chitin;
 e) dissolving the regenerated chitin in an ionic liquid to form a solution;
 f) adding an adjunct ingredient to the solution formed in step (e) to form a chitin/adjunct ingredient admixture solution; and
 g) adding a coagulant to the solution of step (f) and casting the regenerated chitin/adjunct ingredient admixture into a film, a fiber, or a bead.

The following is a description of the process wherein the resulting films, fibers, or beads comprise chitinous materials.

Step (a): Dissolving or Dispersing a Source of Chitin to Form a First Solution

Step (a) of the disclosed process relates to dissolving or dispersing a source of chitin. The source of chitin can be chitinous biomass, pure chitin, technical or practical grade chitin, ground or pulverized exoskeleton of arthropods, i.e., crustaceans. In one embodiment, the source of chitin is pure chitin, for example, pure chitin obtained from crab shells, C9752, available from Sigma™ St. Louis, Mo. In another embodiment, the source of chitin is practical grade chitin obtained from crab shells, C7170, available from Sigma™ St. Louis, Mo. In a further embodiment, the source of chitin is chitinous biomass, such as shrimp shells that are removed from the meat by peeling and processed to insure all shrimp meat is removed. However, any biomass comprising chitin or mixtures of chitin and chitosan, or mixtures of chitin, chitosan, and other polysaccharides can be used as the source of chitin in step (a).

When contemplating the source of chitin, the formulator can take into consideration the amount of chitin that comprises the source of chitin. For example, "pure chitin" can comprise from about 75% to about 85% by weight of chitin. In one example, pure chitin comprises about 81.8% of chitin. "Technical grade" or "practical grade" chitin can comprise from about 70% to about 80% by weight of chitin. In one example, practical chitin comprises about 78.9% of chitin. As it relates to crude biomass sources, one example of shrimps skins or shells comprises 27.2% chitin, while, one example of crab shells comprises 23.9% chitin by weight.

In one aspect of the disclosed process, high molecular weight chitin is obtained by directly dissolving or dispersing a chitinous biomass in an ionic liquid. The chitin obtained by this process is not broken down into small polysaccharide chains as is the case with practical grade or pure grade chitin. As such, direct dissolution of chitin from a biomass allows the formulator to obtain high molecular weight chitin than can be subsequently used to form films, fibers, or beads having different properties than in the case wherein the source of chitin is not directly extracted from a chitinous biomass. In addition, as disclosed herein, the biomass derived chitin can be admixed with one or more adjunct ingredients to form polymeric compositions have properties not obtainable from pure or practical grade chitin.

The source of chitin can be dissolved in an ionic liquid alone, an organic solvent alone, or in a mixture of an ionic liquid and an organic solvent. In one embodiment, the source of chitin is dissolved in an ionic liquid. The source of chitin can be dissolved or dispersed at a temperature of from about 70° C. to about 130° C. In one iteration of this embodiment, the source of chitin can be dissolved or dispersed at a temperature of from about 90° C. to about 110° C. In one particular example, the source of chitin can be dissolved or dispersed at a temperature of about 100° C. However, the source of chitin can be dissolved or dispersed at any temperature, for example, 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., and 130° C.

In one embodiment of step (a), microwave heating is used to dissolve chitin when the source of chitin is a chitinous biomass, for example, shrimp shells. In one iteration, the chitinous biomass can be combined with an ionic liquid or an ionic liquid/co-solvent. The mixture is charge to a source of microwave radiation and the mixture heated to extract the chitin. In one example, short 1 to 5 second pulses are used, however, and pulse time can be used to extract the biomass chitin, i.e., 1 second, 2 seconds, 3 seconds, 4 seconds, or 5 seconds, or any fractional part thereof. For this embodiment, the temperature can be critical, however, microwave heating provides an efficient and desirable method for extracting high molecular weight chitin from a biomass.

Ionic Liquids

The following is a non-limiting disclosure of the ionic liquids suitable for use in the disclosed process.

Ionic liquids are a class of solvents composed of ionized species in contrast to traditional organic or aqueous solvents which are molecular non-ionics. Ionic liquids are salts that exist in the liquid phase at a temperature from about −70° C. to about 300° C. The ionic liquids of the present disclosure comprise an organic cation and an organic or inorganic anion. The organic cation is typically formed by alkylation of a neutral organic species capable of holding a positive charge when a suitable anion is present.

Cations

The organic cation of the ionic liquids disclosed herein can comprise a linear, branched, or cyclic heteroalkyl unit. The term "heteroalkyl" refers to a cation as disclosed herein comprising one or more heteroatoms chosen from nitrogen, oxygen, sulfur, boron, or phosphorous capable of forming a cation. The heteroatom can be a part of a ring formed with one or more other heteroatoms, for example, pyridinyl, imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed. For example, the cation [$C_n$mim] where n is an integer of from 1 to 8 can be used. Preferably, ionic liquids with the cation [$C_{1-4}$mim] can be used. A particularly useful ionic liquid is 1-ethyl-3-methyl-1H-imidazol-3-ium acetate, [$C_2$mim]OAc, having the formulae:

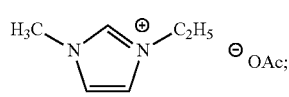

is an example of an ionic liquid comprising a cyclic heteroalkyl cation; a ring comprising 3 carbon atoms and 2 nitrogen atoms.

Other non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxahospholes, pyrroles, boroles, furans, thiphenes, phospholes, pentazoles, indoles, indolines, oxazoles, isothirazoles, tetrazoles, benzofurans, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, and quinoxalines.

The following are examples of heterocyclic units that are suitable for forming a cyclic heteroalkyl cation unit of the disclosed ionic liquids:

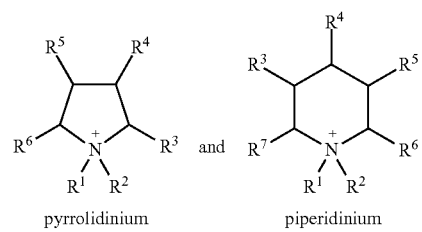

pyrrolidinium            piperidinium

The following are further examples of heterocyclic units that are suitable for forming a cyclic heteroalkyl cation unit of the disclosed ionic liquids:

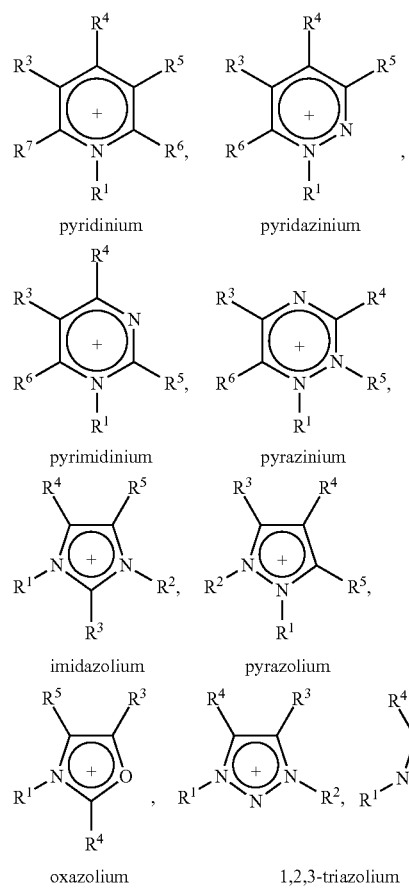

pyridinium            pyridazinium pyrimidinium          pyrazinium imidazolium           pyrazolium oxazolium             1,2,3-triazolium -continued

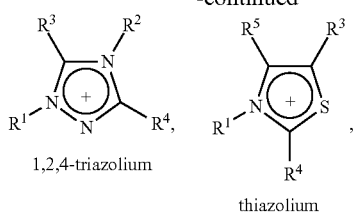

1,2,4-triazolium thiazolium

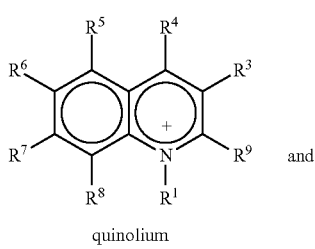

quinolium

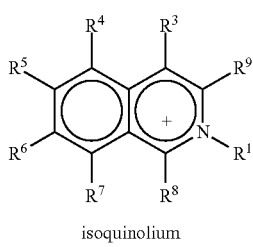

isoquinolium where each $R^1$ and $R^2$ is, independently, a substituted or unsubstituted linear, branched, or cyclic $C_1$-$C_6$ alkyl, or substituted or unsubstituted linear, branched, or cyclic $C_1$-$C_6$ alkoxy; each $R^3$, $R^4$, $R^5$, $R^6$, $R^7$, $R^8$, and $R^9$ is, independently, hydrogen, substituted or unsubstituted linear, branched, or cyclic $C_1$-$C_6$ alkyl, substituted or unsubstituted linear, branched, or cyclic $C_1$-$C_6$ alkoxy, or substituted or unsubstituted linear or branched, $C_1$-$C_6$ alkoxyalkyl.

The following comprises yet another set of examples of heterocyclic units that are suitable for forming heterocyclic dication units of the disclosed ionic liquids and are referred to as such or as "geminal ionic liquids:" See Armstrong, D. W. et al., Structure and properties of high stability geminal dicationic ionic liquids, *J. Amer. Chem. Soc.* 2005; 127(2):593-604; and Rogers, R. D. et al., Mercury(II) partitioning from aqueous solutions with a new, hydrophobic ethylene-glycol functionalized bis-imidazolium ionic liquid, *Green Chem.* 2003; 5:129-135 included herein by reference in its entirety.

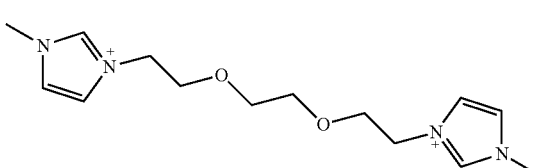

1,1'-[1,2-ethanediylbis(oxy-1,2-ethanediyl)]bis[3-methyl-1H-imidazolium-1-yl]

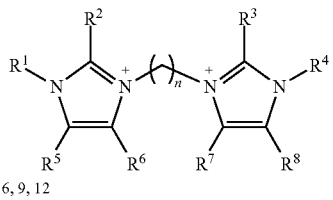

n = 3, 6, 9, 12

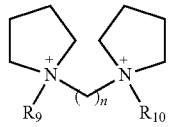

n = 3, 9 imidazolium and pyrrolidinium based di-cations where $R^1$, $R^4$, $R^9$, and $R^{10}$ comprise a substituted or unsubstituted linear, branched, or cyclic $C_1$-$C_6$ alkyl, or substituted or unsubstituted linear, branched, or cyclic $C_1$-$C_6$ alkoxy; each $R^5$, $R^6$, $R^7$, and $R^8$ is, independently, hydrogen, substituted or unsubstituted linear, branched, or cyclic $C_1$-$C_6$ alkyl, substituted or unsubstituted linear, branched, or cyclic $C_1$-$C_6$ alkoxy, or substituted or unsubstituted linear or branched, $C_1$-$C_6$ alkoxyalkyl.

The following is a description of the short hand method used throughout the specification for referring to the imidazolium-based ionic liquids disclosed herein. The template:

[$C_n$mim]

represents the cation portion of the ionic liquid wherein $C_n$ represent an alkyl or substituted alkyl moiety having n number of carbon atoms. The term "mim" refers to "methyl substituted imidazolium." $C_n$mPy is likewise used to refer to Cn-methyl substituted pyridinium. Referring to the generic imidazolium formula:

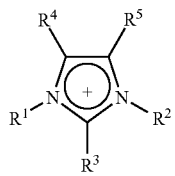

wherein $R^3$, $R^4$, and $R^5$ are each hydrogen, can also be written as follows:

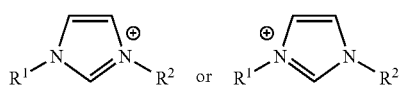

wherein either nitrogen can be depicted as having a positive charge. By the convention used herein the methyl group of "mim" refers to the $R^1$ moiety and the $C_n$ substituent is the $R^2$ moiety. Therefore [$C_2$mim] represents a cation having the formula:

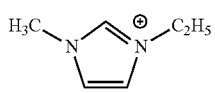

which can be equally well represented by the formula:

Anions

The choice of the anion in the ionic liquid can be particularly relevant to the rate and level of chitin dissolution. While not wishing to be bound by theory, the primary mechanism of solvation of carbohydrates by an ionic liquid is the anion's ability to break the extensive hydrogen-bonding networks by specific interactions with hydroxyl groups. Thus, it is believed that that the dissolution of chitin is enhanced by increasing the hydrogen bond acceptance and basicity of the anion. Anions that also form less viscous ionic liquids are also preferred. By using anions that can accept hydrogen bonds and that are relatively basic, one can not only dissolve pure chitin, but one can dissolve practical grade chitin and even extract chitin from raw chitinous biomass, as described herein. Accordingly, preferred anions are substituted or unsubstituted acyl units $R^{10}CO_2$, for example, formate $HCO_2$, acetate $CH_3CO_2$, proprionate, $CH_3CH_2CO_2$, butyrate $CH_3CH_2CH_2CO_2$, and benzylate, $C_6H_5CO_2$; substituted or unsubstituted sulfates: $(R^{10}O)S(=O)_2O$; substituted or unsubstituted sulfonates $R^{10}SO_3$, for example $(CF_3)SO_3$; substituted or unsubstituted phosphates: $(R^{10}O)_2P(=O)O$; and substituted or unsubstituted carboxylates: $(R^{10}O)C(=O)O$. Non-limiting examples of $R^{10}$ include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno. In especially preferred embodiuments, the anion is $C_{1-6}$ carboxylate.

Still further examples of preferred anion are deprotonated amino acids, for example, Isoleucine, Alanine, Leucine, Asparagine, Lysine, Aspartic Acid, Methionine, Cysteine, Phenylalanine, Glutamic Acid, Threonine, Glutamine, Tryptophan, Glycine, Valine, Proline, Selenocysteine, Serine, Tyrosine, Arginine, Histidine, Ornithine, Taurine.

It is also contemplated that other anions, though not preferred, can still be used in some instances. However, in these instances, higher concentrations, longer mixing times, and higher temperatures can be required. One can use halogens, (i.e., F, Cl, Br, and I), $CO_3^{2-}$; $NO_2^-$, $NO_3^-$, $SO_4^{2-}$, $CN^-$, arsenate(V), $AsX_6$; $AsF_6$, and the like; stibate(V) (antimony), $SbX_6$; $SbF_6$, and the like. Borides $BX_4$, wherein X represents halogen (i.e., $BF_4$, $BCl_4$), and phosphates(V), $PX_6$; $PF_6$, have, however, been found not to work.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

One embodiment of ionic liquids comprise an anion chosen from formate, acetate, propionate, butyrate, $(CF_3)SO_3$, $(R^{10}O)S(=O)_2O$; $(R^{10}O)_2P(=O)O$; $(R^{10}O)C(=O)O$; and $R^{10}CO_2$; each $R^{10}$ is independently $C_1$-$C_6$ alkyl. Anions that are chosen from $R^{10}CO_2$ have been found to be convenient in forming the compositions of step (a) in the compositions and processes disclosed herein.

The anion portion of the ionic liquid is written without the charge, for example, OAc, $CHO_2$, Cl, Br, $RCH_3OPO_2$, and $PF_6$.

IL EXAMPLES

The following are non-limiting examples of ionic liquids written in the short hand convention with the corresponding formula:

i) [$C_2$mim]OAc having the formula:

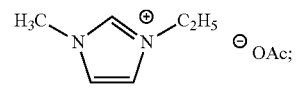

ii) [$C_2$mim]($C_2H_5O$)$SO_3$ having the formula:

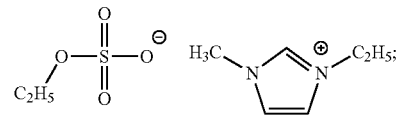

iii) [$C_2$mim]X, where X is chloride or bromide, having the formula:

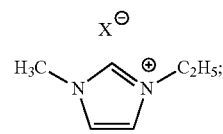

iv) [$C_2$mim]$RCH_3OPO_2$, where $RCH_3OPO_2$ is an alkane phosphonate with R being an alkyl chain, having the formula:

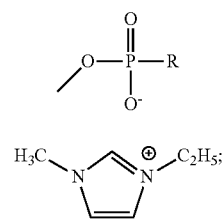

v) [C₂mim](C₂H₅O)₂PO₂ having the formula:

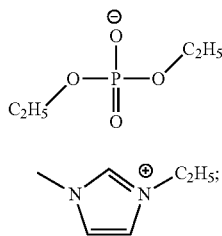

vi) [Amim]CHCO₂, where A is allyl, having the formula:

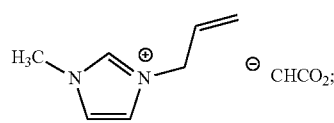

vii) [Amim]X, where A is allyl, and X is Cl or Br, having the formula:

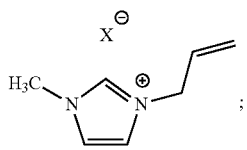

viii) [C₄mim]X, where X is Cl or Br, having the formula:

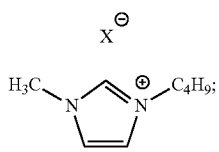

ix) [C₄mim]OAc having the formula:

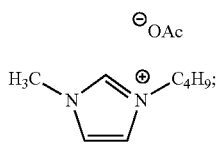

x) [C₄mim]CHCO₂ having the formula:

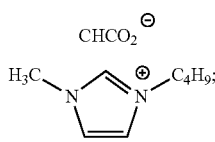

and xi) [C₄miPy]X, where X is Cl or Br, Py is pyrimidyl, having the formula:

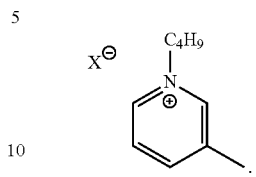

Of course, any of the anions in these specific examples can be combined with any other cations in these specific examples to form ionic liquids suitable for use herein. In one iteration of this embodiment, 3-ethyl-1-methyl-1H-imidazol-3-ium acetate, [C₂mim]OAc, having the formulae:

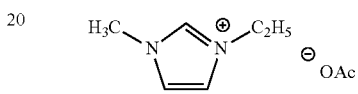

is used to dissolve or disperse the source of chitin in step (a) of the disclosed process.

In another embodiment, the source of chitin is dissolved in an organic solvent. The source of chitin can be dissolved or dispersed at a temperature of from about 0° C. to about 50° C. In one iteration of this embodiment, the source of chitin can be dissolved or dispersed at a temperature of from about 15° C. to about 30° C. In one particular example, the source of chitin can be dissolved or dispersed at a temperature of about 25° C. However, the source of chitin can be dissolved or dispersed at any temperature, for example, 0° C., 1° C., 2° C., 3° C., 4° C., 5° C., 6° C., 7° C., 1° C., 2° C., 3° C., 4° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., and 50° C.

Any organic solvent that effectively dissolves the chitin, chitosan, other polysaccharides present in the source of chitin can be used for this step. What is meant by "effectively dissolves" is at least about 25% by weight of the chitin present is solubilized. In one embodiment, at least about 45% of the chitin, chitosan, other polysaccharides present is solubilized. In another embodiment, at least about 60% of the chitin, chitosan, other polysaccharides present is solubilized. In a further embodiment, at least about 75% of the chitin, chitosan, other polysaccharides present is solubilized. In a still further embodiment, at least about 90% of the chitin, chitosan, other polysaccharides present is solubilized.

In one iteration of this embodiment, dimethylsulfoxide, DMSO, is used as the organic solvent in step (a). Other suitable solvents include, dimethylformamide, DMF, hexamethyl-phosphoramide, HMPA, and the like.

In a further embodiment, the source of chitin is dissolved in an admixture of an ionic liquid and a co-solvent. The source of chitin can be dissolved or dispersed at a temperature of from about 70° C. to about 130° C. In one iteration of this embodiment, the source of chitin can be dissolved or dispersed at a temperature of from about 90° C. to about 110° C. In one particular example, the source of chitin can be dissolved or dispersed at a temperature of about 100° C. However, the source of chitin can be dissolved or dispersed at any temperature, for example, 70° C., 71° C., 72° C., 73° C., 74°

C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., and 130° C.

The term "co-solvent" as used herein means any suitable solvent other than an ionic liquid, for example, DMSO. This embodiment also includes multiple solvents, for example, two or more ionic liquids and one co-solvent, one ionic liquid and two or more co-solvents, and two or more ionic liquids and two or more co-solvents. For this embodiment, any ratio of ionic liquid to co-solvent can be used, for example, from about 5:95 ionic liquid/co-solvent to 95:5 ionic liquid/co-solvent weight/weight. In one example, the ratio of ionic liquid to co-solvent is 25:1.

In one aspect of the disclosed process, an adjunct ingredient can be added to the solution or dispersion obtained in step (a), especially for embodiments wherein chitin is directly cast into films, fibers, or beads by the subsequent addition of a coagulant. This aspect can be summarized as a process comprising:

a) contacting an ionic liquid with a chitinous biomass to form a residue and a chitin comprising solution;
b) adding an adjunct ingredient to the chitin comprising solution; and
c) adding a coagulant to the solution formed in step (a) and casting the chitin comprising solution into a film, a fiber, or a bead.

The following are non-limiting examples of adjunct ingredients that can be added to the solution in step (a) or to the process in any of the succeeding steps.

The disclosed process does not limit the time necessary to dissolve or disperse the source of chitin in step (a), nor does the presently disclosed process require that all of the source of chitin that can be solublized in step (a) must be solublized before proceeding to step (b). As such, the undissolved material separated in step (b), as disclosed herein below, can be recycled back into step (a) and any unsolublized source of chitin can suffice as part of a feedstock source of chitin.

Step (b): Separating the Undissolved Material to Form a Second Solution.

Step (b) relates to separating any non-solublized material from the solublized chitin, chitosan, or other polysaccharides present. The non-solublized material can be inorganic matter, as can be the case when clam shells or shrimp skins/shells are used as the source of chitin. In one embodiment, the non-solublized material is solublizable chitin, however, due to the process conditions chosen by the formulator, the solids are separated before all of the solublizable chitin is in solution. In practice, undissolved chitin can be recycled into step (a) as part of the source of chitin.

The undissolved material can be removed by any process chosen by the formulator. For example, the material can be removed by centrifugation, filtration, or by decanting the liquid phase.

Step (c): Adding a Coagulant to the Second Solution to Regenerate the Solublized Chitin Step (c) of the disclosed process relates to adding a coagulant to the insoluble material-free solution obtained in step (b). The coagulant causes the solubilized matter to be regenerated in solid form. The formulator can use any coagulant suitable for the disclosed process.

The coagulant can be water, a $C_1$-$C_{12}$ linear or branched alcohol, or other organic solvent not suitable for dissolving or dispersing the source of chitin in step (a). In one embodiment, the coagulant is water. In another embodiment, the coagulant is a $C_1$-$C_4$ linear or branched alcohol, for example, methanol, ethanol, propanol, iso-propanol, butanol, sec-butanol, iso-butanol, or tert-butanol. In one example, ethanol is used as the coagulant. In a further embodiment, a mixture of water and a $C_1$-$C_4$ linear or branched alcohol can be used as a coagulant, for example, water/methanol, water/ethanol, and the like. For this embodiment, any ratio of water to solvent can be used, for example, from about 5:95 water/solvent to 95:5 water/solvent.

The formulator can select the ionic liquid suitable for use in this step of the disclosed process by the one or more factors, for example, solubility of the source of chitin and/or the naturally occurring or synthetic polymer used in the embodiments which produce blended fibers, films, or beads. One method of determining the choice of ionic liquid is as follows. The source of chitin is dissolved in an ionic liquid and heated in an oil at 100° C. for 19 hours in air. For example, practical grade (1 g) or pure chitin (0.5 g) are dissolved in 10 g of an ionic liquid. After heating, the undissolved residues from the sample are diluted with a small amount of DMSO (to reduce the viscosity, as well as remove any dissolved substances adsorbed or trapped within the solid texture), and then the solids are separated by centrifugation, washed with DI water, and then dried in an oven at 80° C. for 20 hours.

Table I below shows non-limiting examples of the solubility of various grades of a suitable starting material in various ionic liquids at 100° C. wherein the solution is stirred for 19 hours. For pure chitin as the source of chitin, 0.5 g was dissolved in 2 g of the corresponding ionic liquid. For practical grad and shrimps shells as the source of chitin, 1 g is dissolved in 10 g of the corresponding ionic liquid.

TABLE I

| | Percent mass dissolved, % | | |
|---|---|---|---|
| | [$C_2$mim]Cl | [$C_4$mim]Cl | [$C_2$mim]OAc |
| Pure Chitin | 13.9 | 24.4 | 80.0 |
| Practical Grade Chitin | 4.2 | 6.8 | 15.2 |
| Shrimp shells | 9.7 | 10.0 | 46.0 |

Surprisingly, [$C_2$mim]OAc dissolved over five times as much pure chitin, over three times as much practical grade chitin, and nearly five times as much chitin from shrimp shells as [$C_2$mim]Cl. This data evidences the surprising effect the nature of the anion has on ionic liquid solvation of chitin. This data also shows that [$C_4$mim]Cl provides better solvation than [$C_2$mim]Cl. It is also noted that in all cases more pure chitin dissolved than practical grade chitin, likely because of the higher mineral content in the practical grade chitin.

Step (d): Isolating the Regenerated Chitin

Step (d) relates to isolating the regenerated chitin from the coagulant/ionic liquid phase. As disclosed herein above, the coagulant/ionic liquid phase may comprise coagulant/ionic liquid, coagulant/ionic liquid co-solvent admixture, or coagulant/organic solvent. The regenerated chitin can be isolated in any manner chosen by the formulator, for example, the regenerated chitin can be removed by centrifugation, filtration, or by decanting the liquid phase.

Step (e): Dissolving the Regenerated Chitin in an Ionic Liquid

Step (e) relates to dissolving the regenerated chitin in an ionic liquid. The regenerated chitin can be dissolved or dispersed at a temperature of from about 0° C. to about 50° C. In one iteration of this embodiment, the regenerated chitin can be dissolved or dispersed at a temperature of from about 15°

C. to about 30° C. In one particular example, the regenerated chitin can be dissolved or dispersed at a temperature of about 25° C. However, the regenerated chitin can be dissolved or dispersed at any temperature, for example, 0° C., 1° C., 2° C., 3° C., 4° C., 5° C., 6° C., 7° C., 1° C., 2° C., 3° C., 4° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., and 50° C.

Any suitable ionic liquid as disclosed herein is suitable for use in dissolving the regenerated chitin in step (e). In one embodiment, the ionic liquid in step (e) is 3-ethyl-1-methyl-1H-imidazol-3-ium acetate, [C₂mim]OAc, having the formula:

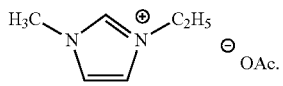

Step (f): Adding a Coagulant and Casting the Regenerated Chitin into a Film, a Fiber, or a Bead.

Step (f) relates to adding a coagulant to the solution formed in step (e) and subsequently casting the chitinous material that regenerates into a film, a fiber, or a bead. The rate at which the coagulant is added can be adjusted by the formulator to control the rate at which the chitinous material regenerates.

The coagulant useful for step (f) can be water, a $C_1$-$C_{12}$ linear or branched alcohol, or other organic solvent not suitable for dissolving or dispersing the source of chitin in step (a). In one embodiment, the coagulant is water. In another embodiment, the coagulant is a $C_1$-$C_4$ linear or branched alcohol, for example, methanol, ethanol, propanol, iso-propanol, butanol, sec-butanol, iso-butanol, or tert-butanol. In one example, ethanol is used as the coagulant. In a further embodiment, a mixture of water and a $C_1$-$C_4$ linear or branched alcohol can be used as a coagulant, for example, water/methanol, water/ethanol, and the like. For this embodiment, any ratio of water to solvent can be used, for example, from about 5:95 water/solvent to 95:5 water/solvent.

The films, fibers, or beads can be formed by any process chosen by the formulator. The disclosed fibers can be manufactured by extrusion, i.e., by forcing the solution in step (f) comprising regenerated chitinous material through the tiny holes of a spinneret to form continuous filaments of semi-solid polymer. The spinnerets used can be any chosen by the formulator that is consistent with the properties of the regenerated chitinous mass and properties of the composition obtained in step (f). For example, the spinneret may have from one to several hundred holes. Because the disclosed process provides highly purified chitin, there are few, if any, impurities to occlude the tiny openings. Each of the four general methods for spinning filament, for example, wet, dry, melt, and gel spinning can be adapted for use with the present process.

The following is a description of the process wherein the resulting films, fibers, or beads comprise an admixture of chitinous material and a naturally occurring or synthetic polymer. In general, this aspect comprises:

a) dissolving or dispersing a source of chitin in an ionic liquid, a co-solvent, or a mixture of an ionic liquid and an organic solvent to form a first solution;

b) separating the undissolved material to form a second solution;

c) adding a coagulant to the second solution to form regenerated chitin;

d) isolating the regenerated chitin;

e) dissolving the regenerated chitin in an ionic liquid to form a solution;

f) dissolving one or more polymers in an ionic liquid to form a solution;

g) combining the solution from step (e) and step (f) to form a polymer admixture solution; and h) adding a coagulant to the polymer admixture solution of step (g) and casting the polymer admixture from step (g) into a film, a fiber, or a bead.

Steps (a) through (d) of this aspect can be conducted in the same manner as disclosed herein above for films, fibers, and beads comprising chitinous material.

Steps (e) and (f) relate to separately dissolving regenerated chitin and a naturally occurring or synthetic polymer in an ionic liquid. These two steps can be done in any order. In one embodiment, however, the formulator can combine these two steps into one step by admixing the regenerated source of chitin with a naturally occurring or synthetic polymer and dissolving the admixture in a one or more ionic liquids. When using this embodiment, step (g) of the disclosed process is obviated.

In one embodiment, the second polymeric material is a naturally occurring polymer, for example, a cellulosic material. As such, for this embodiment the regenerated chitin is dissolved in a suitable ionic liquid. The regenerated chitin can be dissolved at a temperature of from about 70° C. to about 130° C. In one iteration of this embodiment, the regenerated chitin can be dissolved or dispersed at a temperature of from about 90° C. to about 110° C. In one particular example, the regenerated chitin can be dissolved or dispersed at a temperature of about 100° C. However, the regenerated chitin can be dissolved or dispersed at any temperature, for example, 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., and 130° C., where any of the stated values can form an upper or lower endpoint of a range.

The cellulose can be dissolved at a temperature of from about 70° C. to about 130° C. In one iteration of this embodiment, the cellulose can be dissolved or dispersed at a temperature of from about 90° C. to about 110° C. In one particular example, the cellulose can be dissolved or dispersed at a temperature of about 100° C. However, the cellulose can be dissolved or dispersed at any temperature, for example, 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., and 130° C., where any of the stated values can form an upper or lower endpoint of a range.

In another embodiment, the second polymeric material is a synthetic polymer, for example, poly(2-hydroxyethyl methacrylate) (poly-HEMA). As such, for this embodiment the synthetic polymer is dissolved in a suitable ionic liquid. Depending upon the specific synthetic polymer, the temperature at which the polymer is dissolved in an ionic liquid will depend upon the solubility of the particular polymer or upon the concentration of polymer that is desired by the formulator. In one example, poly-HEMA is dissolved at a temperature of from about 70° C. to about 130° C. In one iteration of this embodiment, the poly-HEMA can be dissolved or dispersed at a temperature of from about 90° C. to about 110° C. In one particular example, the poly-HEMA can be dissolved or dispersed at a temperature of about 100° C. However, the poly-HEMA can be dissolved or dispersed at any temperature, for example, 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., and 130° C., where any of the stated values can form an upper or lower endpoint of a range.

The ionic liquid used in steps (e) and (f) can be the same or different, for example, a first ionic liquid can be used to dissolve the regenerated chitin and a second ionic liquid can be used to dissolve the naturally occurring or synthetic polymer. Alternatively, an admixture of ionic liquids can be used to dissolve separately both the regenerated chitin and the polymer. The ratio of the two ionic liquids when mixtures are used can be the same for the regenerated chitin and polymer, or the ratio can be different to aid in solublizing the respective ingredients.

Step (g): Combining the Solution from Step (e) and Step (f) to Form a Polymer Admixture Solution Step (g) relates to combining the regenerated chitin solution with the polymer solution. As discussed herein above, this step can be obviated if the formulator elects to combine the regenerated chitin and polymer and dissolve the two in one or more ionic liquids. Once combined, the temperature of the polymer admixture solution can be raised, lowered or held constant such that the casting solution formed in step (h) has the desired properties for the product being formed, i.e., film, fiber, or bead.

Step (h): Adding a Coagulant to the Polymer Admixture Solution of Step (g) and Casting the Polymer Admixture from Step (g) into a Film, a Fiber, or a Bead The coagulant useful for step (h) can be water, a $C_1$-$C_{12}$ linear or branched alcohol, or other organic solvent not suitable for dissolving or dispersing the source of chitin in steps (e) and (f). In one embodiment, the coagulant is water. In another embodiment, the coagulant is a $C_1$-$C_4$ linear or branched alcohol, for example, methanol, ethanol, propanol, iso-propanol, butanol, sec-butanol, iso-butanol, or tert-butanol. In one example, ethanol is used as the coagulant. In a further embodiment, a mixture of water and a $C_1$-$C_4$ linear or branched alcohol can be used as a coagulant, for example, water/methanol, water/ethanol, and the like. For this embodiment, any ratio of water to solvent can be used, for example, from about 5:95 water/solvent to 95:5 water/solvent.

The films, fibers, or beads can be formed by any process chosen by the formulator. The disclosed fibers can be manufactured by extrusion, i.e., by forcing the solution in step (h) comprising regenerated chitinous material and one or more polymers through the tiny holes of a spinneret to form continuous filaments of semi-solid polymer. The spinnerets used can be any chosen by the formulator that is consistent with the properties of the regenerated chitinous/polymer mass and properties. The spinneret may have from one to several hundred holes. Because the disclosed process provides highly purified chitin, there are few, if any, impurities to occlude the tiny openings. Each of the four general methods for spinning filament, for example, wet, dry, melt, and gel spinning can be adapted for use with the present process.

The following are non-limiting examples of several aspects of the disclosed process. These examples are not intended to circumscribe the full scope of the disclosed process, but to provide the formulator with suitable examples that can serve as the basis for executing the iterations, examples, and embodiments embraced within the present disclosure.

The ionic liquids, i.e., [C$_2$mim]Cl, [C$_4$mim]Cl, and [C$_2$mim]OAc (purity≥95%) were obtained from BASF™ and dried in a vacuum oven at ~70° C. for 20 hours before use. Dimethyl sulfoxide (DMSO) (≥99.6%) and Poly(2-hydroxyethyl methacrylate) (Poly-HEMA) were purchased from Aldrich (St. Louis, Mo.) and used as received. Deionized (DI) water was obtained from a commercial deionizer (Culligan™: Northbrook, Ill.) with specific resistivity of 17.25 MΩ-cm at 25° C. Pure chitin (from crab shells, Cat. No. C9752) and practical grade chitin (from crab shells, Cat. No. C7170) were purchased from Sigma™ (St. Louis, Mo.) and used directly without further purification. Frozen shrimp were obtained from Cox's Wholesale Seafood, Inc. (Tampa, Fla.). The shrimp were thawed, carefully peeled to make sure no obvious shrimp meat was left, and the back and tail of the shells were retained. The shells were washed three times with tap water and then dried in oven (Precision Econotherm Laboratory oven) at 80° C. for 2 days. The dried shells were ground for 1 minute using a Janke & Kunkel™ mill (Ika Laborteehnik, Wilmington, N.C.) and separated using a sieve into particle sizes of 0.125 to 0.5 mm. Crab legs were obtained from a local market and processed in a similar manner.

General Procedure for Determining the Amount of Regenerated Chitin Available From a Source of Chitin Approximately 1 g ($m_I$) of pure or practical grade chitin, or dried, ground chitinous biomass (shrimp shells or crab shells) is mixed with 10 g ($m_{IL}$) of dried IL in a 50 mL Pyrex™ glass beaker. The mixture is vigorously stirred (~700 rpm) and heated in an oil bath at 100° C. in air. One method of heating can be accomplished by using a digital magnetic stirring hot plate, for example, an Isotemp™ brand plate available from Fisher Scientific. After heating for approximately 19 hours, or until the formulator is satisfied the chitin is fully dissolved, the mixture is transferred to a 20 mL glass vial, and about 10 mL of DMSO is added to the mixture to reduce the viscosity and remove any dissolved substances adsorbed or trapped within the solid texture. The mixture is vortexed for 30 seconds then centrifuged at 100×g for 10 minutes. A Thermolyne™ type 37600 mixer and a Clay Adams™ Brand DYNAC centrifuge are suitable for this step. The undissolved residue is then separated, washed with DI water (3×20 mL) and dried in an oven at 80° C. for 20 hours. The dried residue is weighed and the dry mass ($m_R$) is used to calculate the percent dissolved using equation 1 to calculate the amount of chitin present and equation 2 to determine the amount of chitin dissolved in solution.

$$\text{Percent Dissolved} = \frac{m_I - m_R}{m_I} \times 100 \quad \text{Equation 1}$$

$$\text{Dissolution (wt \%)} = \frac{m_I - m_R}{m_{IL} + (m_I - m_R)} \times 100 \quad \text{Equation 2}$$

where $m_I$ is the initial mass of dried chitinous sample, and $m_{IL}$ is the mass of IL used in the dissolution. The clear ionic liquid solution is poured slowly into a beaker contains 200 mL of coagulating solvent (DI water or ethanol) and a flocculant will immediately form. Each mixture was then stirred at room temperature for 3 hours and poured into 4 separate 50 mL glass vials for centrifugation. After centrifugation at 100×g for 10 min, the settled flocculants are triply washed with DI water (100 mL), and dried at 80° C. for 20 hours in an oven. The yield of reconstituted chitin is calculated using equation 3:

$$\text{Chitin Reconstitution Yield (wt \%)} = \frac{m_{RC} \times C_{RC}}{m_D \times C_{DC}} \times 100 \quad \text{Equation 3}$$

where in partial dissolution, $m_{RC}$ is the mass of dried reconstituted chitin and $m_D$ is the mass of dissolved chitinous material ($m_D = m_I - m_R$); and where in complete dissolution, $m_D$ is the total amount of chitinous sample dissolved in IL. $C_{RC}$ is the chitin content (wt %) of the reconstituted chitin, $C_{DC}$ is the chitin content (wt %) of the dissolved chitinous sample. Both $C_{RC}$ and $C_{DC}$ were determined according to the Black and Schwartz methodology (See, M. Black, H. Schwartz, *Analyst*, 1950, 75, 185-189). The Kjeldahl nitrogen analysis can also be used to obtain the amount of nitrogen present, and hence the amount of chitin. See, for example, *Official Methods of Analysis of the Association of Official Analytical Chemists*, 13a ed.; Horwitz, W. Ed.; AOAC international: Washington, D.C., 1980, pp 14-15 and Rødde, R. H.; Einbu, A.; Vårum, K. M. *Carbohydrate Polymers*, 2008, 71, 388-393.

The following are non-limiting examples of preparing the disclosed films, fibers, and beads by the disclosed process.

Uses:

The disclosed compositions and solutions can have many uses. They can be fashioned into beads, fibers, films, aerosols, or shaped into particles or other forms. In a particularly useful method, chitin fibers can be prepared according to the disclosed methods and be used in bandages, coated sutures. Other medical applications include contact lenses. The disclosed chitin compositions can also be impregnated with actives and be used for drug delivery. Still further, the disclosed compositions can be used in various cosmetic applications, such as toothpaste, moisturizers, body creams, and make-up. The disclosed compositions can be used in various food applications as preservatives, color stabilizers, or animal feed additives. The disclosed compositions can be used in various agricultural applications, such as a seed coating, leaf coating, or for controlled agrochemical release. The disclosed compositions can be used in environmental applications, such as water treatment, oil remediation, metal ion removal, or as flocculants/coagulants. The disclosed compositions can be used in biotechnology, e.g., for cell immobilization and recovery, protein separations, or glucose electrodes.

Example 1

Approximately 0.5 g ($m_I$) of crude chitin (pure or practical grade), or dried, ground chitinous biomass (shrimp shells or crab shells) was mixed with 10 g ($m_{IL}$) of dried [C₂mim]OAc in a 50-mL Pyrex® glass beaker. The mixture was magnetically vigorously stirred (~700 rpm) and heated in an oil bath at 100° C. in air by a digital stirring hot plate. After heating for 19 hours, the dissolved chitin was separated and reconstituted by the method hereinabove. The dried reconstituted chitin was then re-dissolved in 10 g fresh [C₂mim]OAc and stirred at 100° C. until complete dissolution was achieved.

Example 2

Crude chitin (practical grade) or shrimp/crab shells are pretreated by mixing 0.5 g chitinous sample with 10 g DMSO at room temperature until dissolved with occasional stirring. The mixture was transferred to a 20-mL glass vial and centrifuged at 100×g for 10 min. The light yellow DMSO was decanted and only the settled solid chitinous sample was collected. The wet pretreated chitinous sample was then mixed with 10 g fresh [C₂mim]OAc and stirred at 100° C. for 1-2 hours until a viscous but clear dark red solution was obtained.

Example 3

0.5 g Crude chitin (practical grade) or shrimp/crab shells was mixed with 10 g [C₂mim]OAc and 0.4 g DMSO in a 50-mL Pyrex® glass beaker. The mixture was stirred and heated in an oil bath at 100° C. in air by a digital stirring hot plate till complete dissolution was reached (approximately 1-2 hours).

Example 4

A chitin/cellulose composite fiber/film/bead was made by dissolving each of pure chitin (0.3 g) and cellulose (0.39 g) in 3 g [C₂mim]OAc. The two mixtures were then mixed together and stirred at 100° C. for 30 minutes to produce a homogenous clear solution containing chitin/cellulose (3:4, wt/wt) wherein the total biomass concentration was 10.3 wt % in [C₂mim]OAc. The solution was used to produce chitin/cellulose composite fiber/film/bead by the methods described herein.

Example 5

Cellulose (2 g) was dissolved in 10 g [C₂mim]OAc at 100° C. over a period of 2 hours to give a clear dissolution solution. Cleaned, pulverized shrimp shells (0.5 g) were mixed with 10 g [C₂mim]OAc and the mixture was stirred at 100° C. for 19 hours. After heating, the solution was centrifuged at 100×g for 10 minutes, the upper layer (4.6 wt % of shrimp shell dissolved in [C₂mim]OAc, which equals to 1.25 wt % of chitin in [C₂mim]OAc was separated by decanting and mixed with the produced cellulose [C₂mim]OAc solution. The mixture was stirred at 100° C. for 30 minutes to produce a homogenous clear solution contains chitin/cellulose (0.06:1, wt/wt) in the total biomass concentration of 9.6 wt % in IL. The solution was used to produce a shrimp shell derived chitin/cellulose composite fiber/film/bead by the herein described methods.

Example 6

In the third example, pure chitin (0.2 g) and Poly(2-hydroxyethyl methacrylate) (Poly-HEMA) (0.4 or 0.6 g) were dissolved in 2 g of [C₂mim]OAc, respectively. The two mixtures were then mixed and stirred at 100° C. for 30 min to produce a homogenous clear solution contains chitin/Poly-HEMA (2:3, wt/wt) in the total polymer concentration of 13.0-16.7 wt % in IL. The solution was used to produce chitin/Poly-HEMA composite film by casting. Poly-HEMA belongs to acrylics, which could be used as binders (the actual film forming component of paint) to impart adhesion and bind the components together.

Example 7

One further advantage of the disclosed process is the ability to use microwave radiation as a source of heating the solutions. For example, approximately 0.04 g of practical grade chitin was mixed with 2 g of dried [C$_2$mim]OAc in a 20 mL pyrex vial. The mixture was heated in a domestic microwave oven (SHARP Carousel R-209KK, Mahwah, N.J.) using 3 second pulses at full power (CAUTION: care must be taken to avoid overheating the [C$_2$mim]OAc). Between each pulse, the vial was removed, the mixture was manually stirred by a glass rod and then replaced in the microwave. Complete dissolution was monitored by removing a drop of the mixture and placing it in between two pieces of closely contacted glass slides for observation of any undissolved residue using an optical microscope (Reichert Stereo Star Zoom 580, Depew, N.Y.). After 40 pulses (total time of 2 minutes) the solution was homogeneous. This solution is used directly to form films, fibers, and beads.

Example 8

Approximately 0.4 g of shrimp shells was mixed with 10 g of dried [C$_2$mim]OAc in a 50 mL pyrex vial. The mixture was heated in a domestic microwave oven (SHARP Carousel R-209KK, Mahwah, N.J.) using 3 second pulses at full power (CAUTION: care must be taken to avoid overheating the [C$_2$mim]OAc). Between each pulse, the vial was removed, the mixture was manually stirred by a glass rod and then replaced in the microwave. Complete dissolution was monitored by removing a drop of the mixture and placing it in between two pieces of closely contacted glass slides for observation of any undissolved residue using an optical microscope (Reichert Stereo Star Zoom 580, Depew, N.Y.). After 40 pulses (total time of 3 minutes) the solution was homogeneous. This solution is used directly to form films, fibers, and beads.

Determination of the Amount of Biomass Dissolved in an Ionic Liquid

Samples of chitin obtained from various sources, inter alia, shrimp shells, practical grade chitin, were added in portions of 0.01 g at a time to 10 g on an ionic liquid in a 50 mL Pyrex® glass beaker with a magnetic stir bar, causing a stepwise increase of 0.1 wt % of chitin concentration in the ionic liquid solution. For dissolution of pure chitin, 0.1 wt % of pure chitin was mixed with 2 g of dried ionic liquid in a 20 mL glass vial with a magnetic stir bar. The mixture was vigorously stirred (~700 rpm) and heated in an oil bath at 100° C. in air using a digital stirring hotplate (Isotemp™, Fisher Scientific, Dubuque, Iowa). Complete dissolution was monitored by using an optical microscope as explained above. After each portion was completely dissolved, another portion was added to the mixture until complete dissolution could not be achieved. The maximum amount of biomass dissolved in IL solution is reported in wt % and is calculated using eq. 3:

$$\text{Maximium amount of biomass dissolved in } IL \text{ (wt \%)} = \frac{m_D}{m_{IL} + m_D} \times 100 \qquad \text{Equation 4}$$

where $m_D$ is the mass of dissolved chitinous material and $m_{IL}$, is the mass of ionic liquic used in the dissolution.

Example 9 Comparative

A polymer comprising 11.5 weight % of cellulose is made by the process disclosed in Example 1. The resulting fibers, films and beads are used to illustrate the difference between polymers and polymer blends formed from chitin by the disclosed process and polymers comprising cellulose.

The chitin-[C$_2$mim]OAc complete dissolution mixtures obtained in Examples 1-6 can be used to produce chitin fiber/film/bead. Chitin fiber was produced by the dry jet wet spinning process (see, Sun, N.; Swatloski, R. P.; Maxim, M.; Rahman, M.; Harland, A. G.; Hague, A.; Spear, S. K.; Daly, D. T.; Hague, A.; Harland, A. G.; Rogers, R. D. "Magnetite-embedded cellulose fibers from ionic liquid" *J. Mater. Chem.* 2008, 18, 283-290).

Chitin film was produced by pouring the dissolution mixture carefully on a glass plate, then casting into a film using RDS laboratory coating rod with winding wire on the rod surface (Webster, N.Y.). The film thickness can be controlled by the size of the winding wire on the rod, the bigger the wire diameter, the thicker film can be cast.

Chitin beads were made by dispersing the dissolution mixture into a mechanically vigorously stirring coagulate bath. DI water is used as the coagulant. The produced fiber/film/bead was soaked in warm DI water for 1-2 days to remove the residue IL and then air dried. The diameters of the produce dry fiber, film and bead were in the range of 0.12 mm to 0.2 mm, 0.05 mm to 0.2 mm and 0.25 mm to 1 mm, respectively.

The disclosed process relates to forming films, fibers, and beads which comprise a mixture of chitin and one or more naturally occurring or synthetic polymers. In one iteration, this aspect comprises
  a) dissolving or dispersing a source of chitin in an ionic liquid to form a first solution;
  b) adding one or more naturally occurring or synthetic polymers to form a polymer admixture; and
  c) adding a coagulant to the solution of step (b) and casting the chitin/one or more naturally occurring or synthetic polymers admixture into a film, a fiber, or a bead.

A further iteration of this aspect comprises:
  a) dissolving or dispersing a source of chitin in an ionic liquid to form a first solution;
  b) adding one or more naturally occurring or synthetic polymers to form a polymer admixture;
  c) separating any undissolved material in step (b) to form a second solution;
  d) adding a coagulant to the second solution to form a regenerated chitin/one or more naturally occurring or synthetic polymers composition;
  e) dissolving the composition from step (d) in an ionic liquid to form a solution; and
  f) adding a coagulant to the solution of step (e) and casting the chitin/one or more naturally occurring or synthetic polymers admixture into a film, a fiber, or a bead.

Another iteration of this aspect comprises
  a) dissolving or dispersing a source of chitin in an ionic liquid and a co-solvent to form a first solution;
  b) adding one or more naturally occurring or synthetic polymers to form a polymer admixture; and
  c) adding a coagulant to the solution of step (b) and casting the chitin/one or more naturally occurring or synthetic polymers admixture into a film, a fiber, or a bead.

A yet further iteration of this aspect comprises:
  a) dissolving or dispersing a source of chitin in an ionic liquid and a co-solvent to form a first solution;
  b) adding one or more naturally occurring or synthetic polymers to form a polymer admixture;
  c) adding one or more adjunct ingredients to the polymer admixture; and
  d) adding a coagulant to the solution of step (b) and casting the chitin/one or more naturally occurring or synthetic polymers admixture into a film, a fiber, or a bead.

The disclosed process can be used to make blended polymers that comprise crosslinking agents or that do not comprise a crosslinking agent. Examples of chitin blends comprising a crosslinker include chitin/1,6-diisocyanatohexane, chitin/gluteraldehyde, chitin/glyoxal, chitin/starch/guteraldehyde, and chitin/collagen/gluteraldehyde. Examples of chitin blends without a crosslinker includes chitin/starch/ chitin/gelatin, chitin, collagen, chitin/poly(vinyl alcohol), chitin/poly(caprolactone) and chitin/polyethylene glycol.

Characterization of the Polymers Formed by the Disclosed Process.

The chitin used as a starting material and the regenerated chitin was characterized by elemental analysis, Energy Dispersive X-ray Spectroscopy (EDS), infrared spectroscopy (IR), powder X-ray diffraction (PXRD), scanning electron microscopy (SEM), and tensile strength testing.

Elemental analyses (CHNO) of the source of chitin or of reconstituted chitin were obtained from Galbraith Laboratories, Inc (Knoxyille, Tenn.). EDS spectra were recorded on a Philips XL30 SEM-EDS (Eindhoven, Netherlands) where the SEM was equipped with elemental analysis capabilities. The SEM images were taken with a Philips XL30 SEM instrument. Samples were sputter-coated with gold to improve the conductivity. IR spectroscopy was carried out on a PerkinElmer Spectrum 100 FT-IR spectrometer (Bucks, UK) equipped with an attenuated total reflectance (ATR) cell by accumulation of 4 scans, with a resolution of 2 cm$^{-1}$. The PXRD diffractograms were measured using a Rigaku D/MAX-2BX horizontal X-ray diffractometer (Arlington Heights, Ill.) in the scanning range of 5-40° with scanning speed of 1°/min and step size of 0.1°. The samples were stabilized on silicon wafer substrate using vacuum grease and the silicon wafer mounted on an aluminum sample holder with vacuum suction. The tensile testing was applied on chitin fibers using a MTS QTest/25 tensile testing machine attached with a specially designed pneumatic grip suitable for thin and flexible fiber testing. A gauge length of 72 mm was employed for the measurements. A load cell of 22.4 Newton capacity was used for load measurement. The cross head speed was maintained at 1.27 mm/min and the test data in terms of stress and strain were obtained using a data acquisition system. For sample preparation, 25.4 cm long fibers were cut and used for each testing. At least three samples were tested in each category. For each fiber sample, the diameter was measured by a caliper at ten different position of the fiber and the average was taken and used.

The thermostability of the ILs was monitored by thermogravimetric analysis (TGA). The chitin/IL or IL solutions were characterized by $^{13}$C NMR. The chitin or regenerated chitin was characterized by elemental analysis, energy dispersive X-ray spectroscopy (EDS), infrared (IR) spectroscopy, powder X-ray diffraction (PXRD), TGA, differential scanning calorimetry (DSC), and scanning electron microscopy (SEM).

IR spectroscopy was carried out using a PerkinElmer Spectrum 100 FT-IR spectrometer (Bucks, UK) equipped with an attenuated total reflectance (ATR) cell by accumulation of 4 scans, with a resolution of 2 cm$^{-1}$. The degree of acetylation (DA) of chitinous samples was calculated using eq. 4:

$$A_{1320}/A_{1420} = 0.3822 + 0.03133 \times DA \quad (4)$$

where $A_{1320}$ is the area under the peak at 1320 cm$^{-1}$, and $A_{1420}$ is the area under the peak at 1420 cm$^{-1}$. The baselines were chosen according to the literature, See, J. Brugnerotto et al., *Polymer*, 2001, 42, 3569-3580) and the peak areas were calculated by the IR software.

The PXRD diffractograms were measured using a Rigaku D/MAX-2BX horizontal X-ray diffractometer (Arlington Heights, Ill.) in the scanning range of 5-40° with scanning speed of 1°/min and step size of 0.1°. The samples were stabilized on a silicon wafer substrate using vacuum grease and the silicon wafer was mounted on an aluminum sample holder with vacuum suction. The crystallinity index (CrI) was determined according to the method proposed for chitin and chitosan using eq. 5:

$$CrI_{110} = 100 \times (I_{110} - I_{am})/I_{110} \quad (5)$$

where $I_{110}$ is the maximum intensity of the (110) lattice diffraction (in our case, it is located at 19.1°), and $I_{am}$ is the intensity of amorphous diffraction at 2θ=16°.

The chitin/IL solutions were characterized by $^{13}$C NMR at 70° C. using a Bruker Avance 500 NMR spectrometer (Billerica, Mass.) with a 5 mm BBO probe. A total of 20,000 scans were collected at 125.76 MHz and spectra were processed with a 10 Hz line-broadening factor. To prepare a chitinous solution NMR sample, chitinous material was dissolved in [C$_2$mim]OAc and then mixed with DMSO-d$_6$ to final concentrations of 5 wt % chitinous material, 80 wt % IL, and 15 wt % DMSO.

The choice of coagulant by the formulator can be based on either the properties of the regenerated chitin, the solubility of the source of chitin in a particular ionic liquid, the amount of chitin obtained when regenerating the chitin, or on the availability, cost, or other factors related to a particular ionic liquid. For example, the recovery of chitin dissolved in [C$_2$mim]OAc using three different coagulants is depicted in Table II herein below. For pure chitin, 0.4 g was dissolved in 2 g [C$_2$mim]OAc at 100° C. for 2 hour and complete dissolution was achieved. For shrimp shells, 1 g was mixed with 10 g [C$_2$mim]OAc and the mixture heated at 100° C. for 19 hours, which yielded partial dissolution.

As shown, for pure chitin from 77.5% to 92.5% wt %/wt % of chitin is obtained from the original mass as regenerated chitin. For the case wherein the source of chitin is shrimp shells, from 30% to 35% wt %/wt % is obtained from the original mass as regenerated chitin. Table II herein below summarizes the effect of different coagulants on the efficiency of chitin regeneration.

TABLE II

| | | Coagulant used | | |
|---|---|---|---|---|
| | | DI Water | Ethanol | Methanol |
| Pure chitin | Mass dissolved, g | 0.40 | 0.40 | 0.40 |
| | Reconstituted chitin, (g) | 0.37 | 0.31 | 0.35 |
| Shrimp shells | Mass dissolved, (g) | 0.46 | 0.43 | 0.45 |
| | Reconstituted chitin, (g) | 0.08 | 0.12 | 0.14 |

Table III provides a summary of the elemental analysis of the regenerated chitin depicted in Table II.

TABLE III

| Entry | Theoretical value for chitin (C$_8$H$_{13}$NO$_5$)$_n$ | | C, % | H, % | N, % | O, % |
|---|---|---|---|---|---|---|
| | | | 47.29 | 6.40 | 6.90 | 39.41 |
| 1 | Pure chitin | Result | 42.47 | 6.89 | 6.16 | 42.81 |
| | | % error | 10.19 | 7.66 | 10.72 | 8.63 |
| 2 | Reconstituted pure chitin by H$_2$O | Result | 46.52 | 6.64 | 6.54 | 38.82 |
| | | % error | 1.63 | 3.75 | 5.22 | 1.50 |
| 3 | Reconstituted pure chitin by EtOH | Result | 45.66 | 6.51 | 6.86 | 40.58 |
| | | % error | 3.45 | 1.72 | 0.58 | 2.97 |

TABLE III-continued

| Entry | Theoretical value for chitin (C$_8$H$_{13}$NO$_5$)$_n$ | | C, % 47.29 | H, % 6.40 | N, % 6.90 | O, % 39.41 |
|---|---|---|---|---|---|---|
| 4 | Reconstituted pure chitin by MeOH | Result % error | 44.95 4.95 | 6.40 0.00 | 6.69 3.04 | 40.92 3.83 |
| 5 | Practical grade chitin | Result % error | 44.25 6.43 | 6.89 7.66 | 5.89 14.64 | 39.28 0.33 |
| 6 | Reconstituted practical grade chitin by H$_2$O | Result % error | 45.51 3.76 | 6.50 1.56 | 6.17 10.58 | 39.47 0.15 |
| 7 | Reconstituted chitin from shrimp shells by H$_2$O | Result % error | 44.18 6.58 | 6.72 5.00 | 6.64 3.77 | 41.61 5.58 |
| 8 | Reconstituted chitin from shrimp shells by EtOH | Result % error | 34.47 27.11 | 5.48 14.38 | 5.46 20.87 | 35.00 11.19 |
| 9 | Reconstituted chitin from shrimp shells by MeOH | Result % error | 39.65 16.16 | 5.77 9.84 | 8.73 26.52 | 28.07 28.77 |

Figure 4:
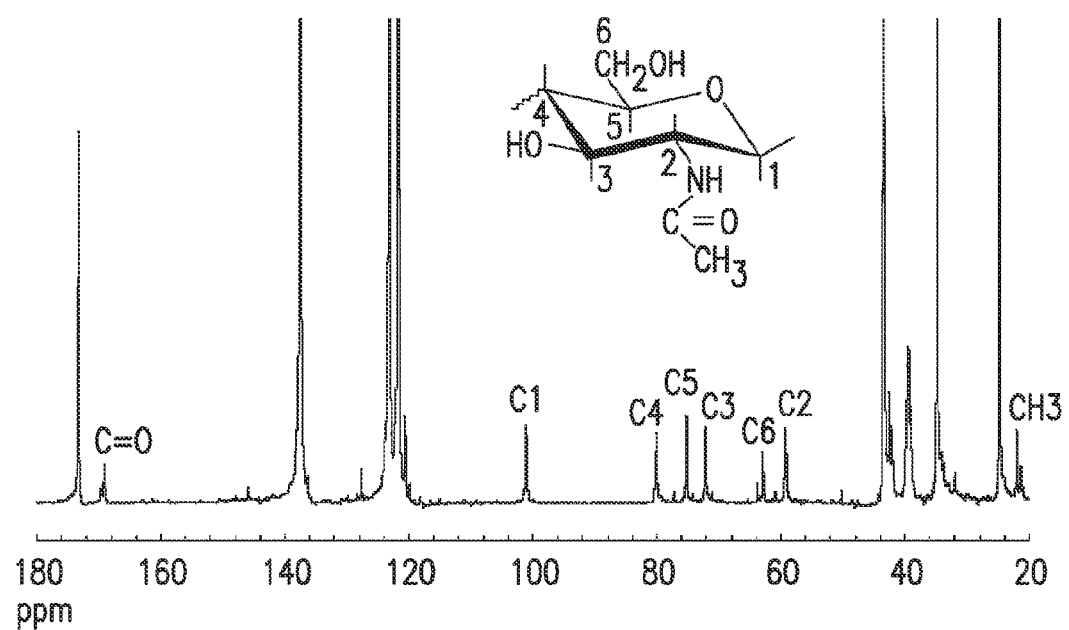
FIG. 4 is the $^{13}$C NMR spectra of reconstituted pure chitin dissolved in [$C_2$mim]OAc.
Figure 5:
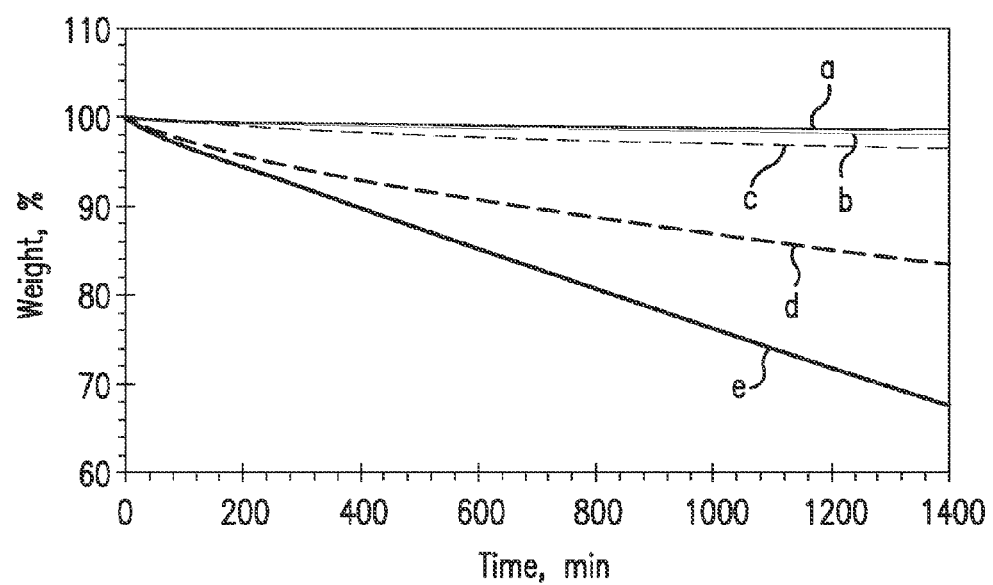
FIG. 5 is a graph of TGA of [$C_2$mim]OAc by heating at target temperature and environment for 24 h: (a) 100° C. in $N_2$; (b) 100° C. in air; (c) 110° C. in $N_2$; (d) 110° C. in air; and (e) 130° C. in air.
Figure 6:
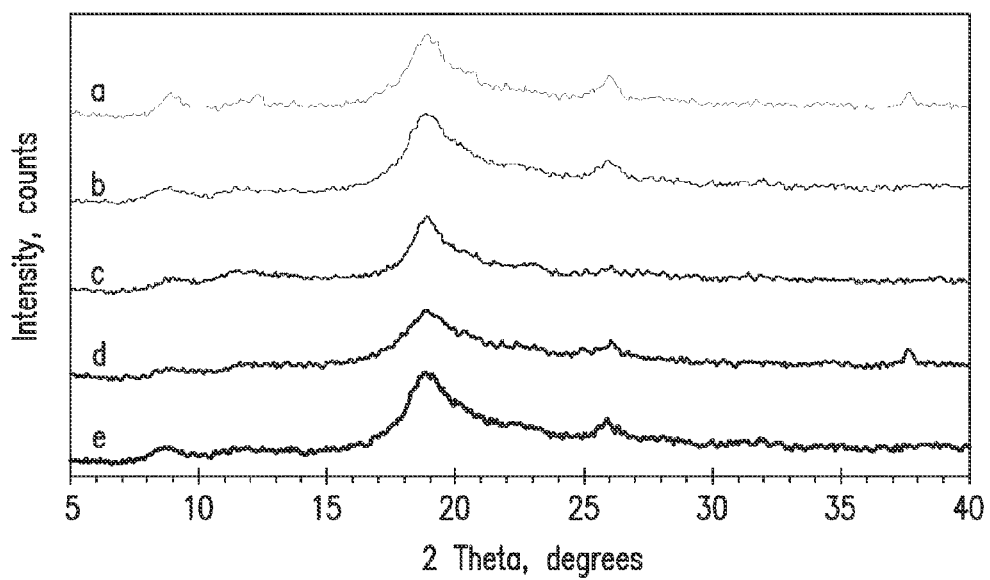
FIG. 6 is a plot of X-ray diffractograms of (a) pure chitin; (b) reconstituted pure chitin; (c) practical grade chitin; (d) reconstituted practical grade chitin; and (e) reconstituted chitin from shrimp shells.
Figure 7:
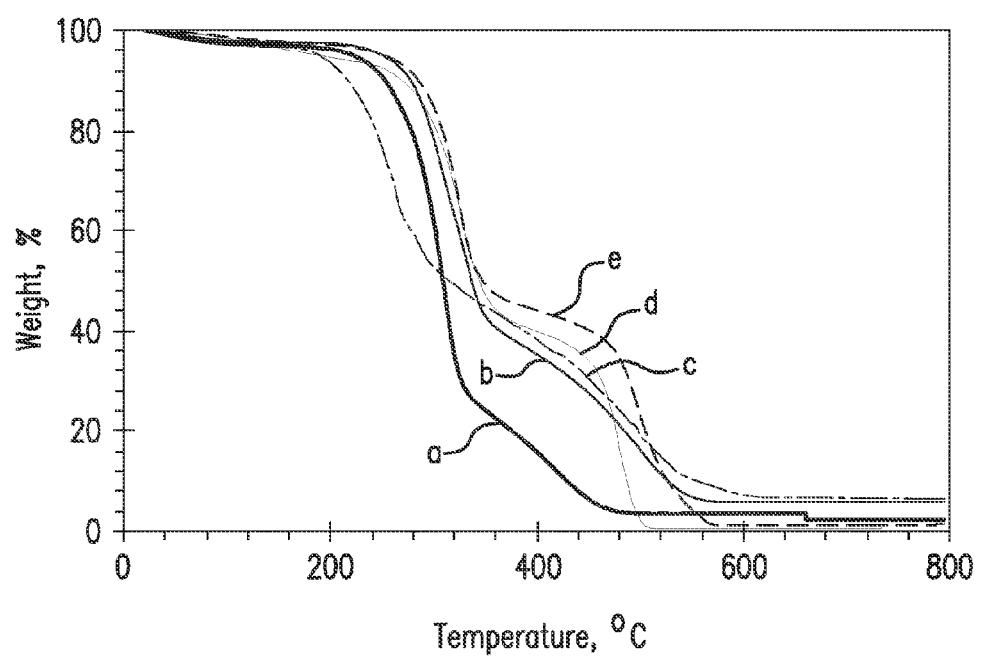
FIG. 7 is a TGA of (a) practical grade chitin; (b) reconstituted pure chitin; (c) pure chitin; (d) reconstituted practical grade chitin; and (e) reconstituted chitin from shrimp shells.
Figure 8B:
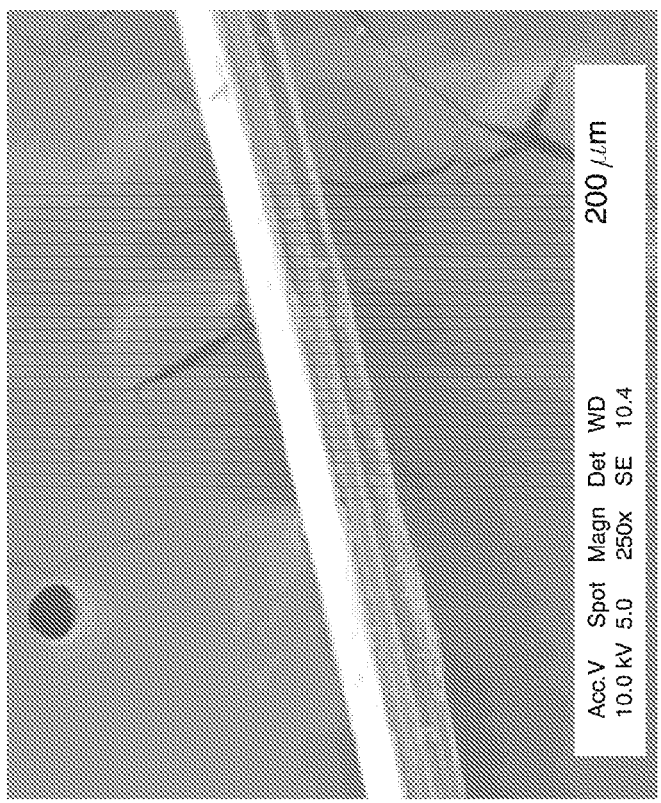
FIG. 8 is a pair of SEM micrographs of the chitin fibers: (a) from shrimp shells and (b) from PG-chitin.
Figure 8A:
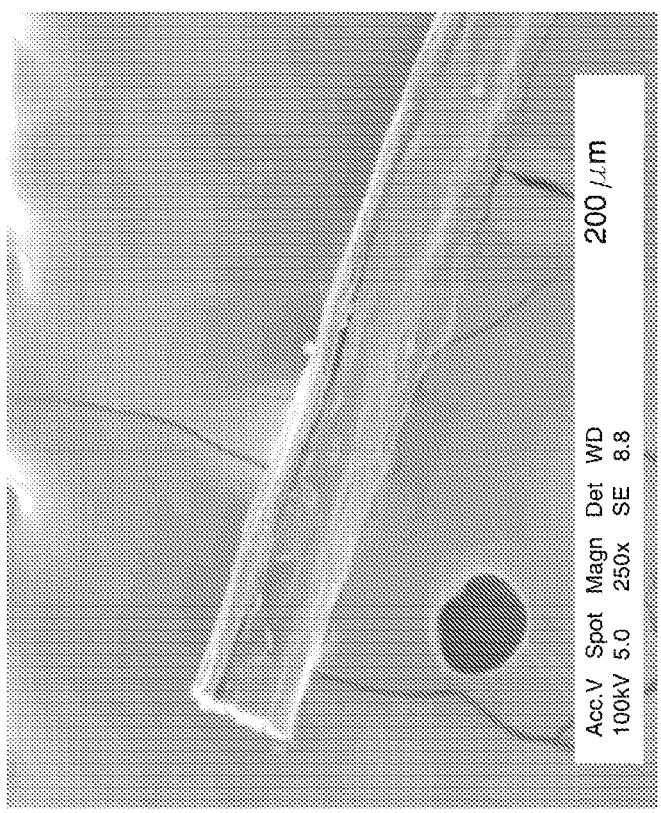
Figure 9A:
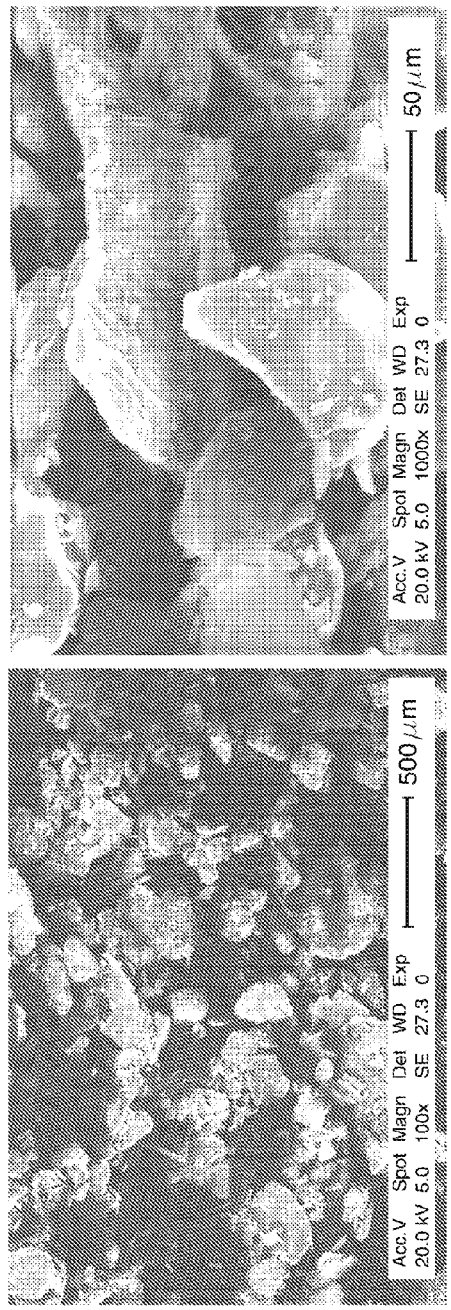
FIG. 9 is a group of SEM micrographs obtained for (a) shrimp shells; (b) undissolved shrimp shell residue; and (c) reconstituted chitin from shrimp shells.
Figure 9B:
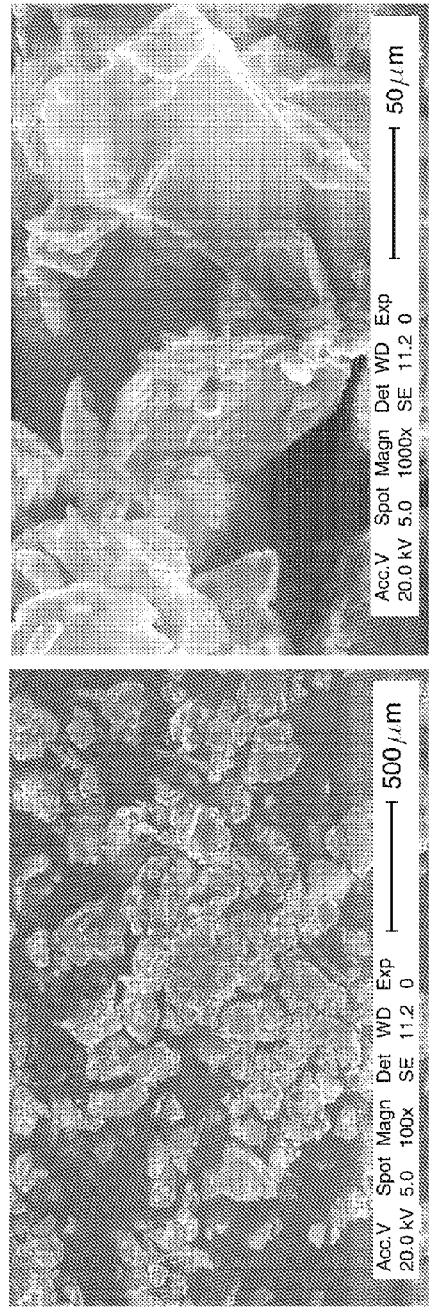
Figure 9C:
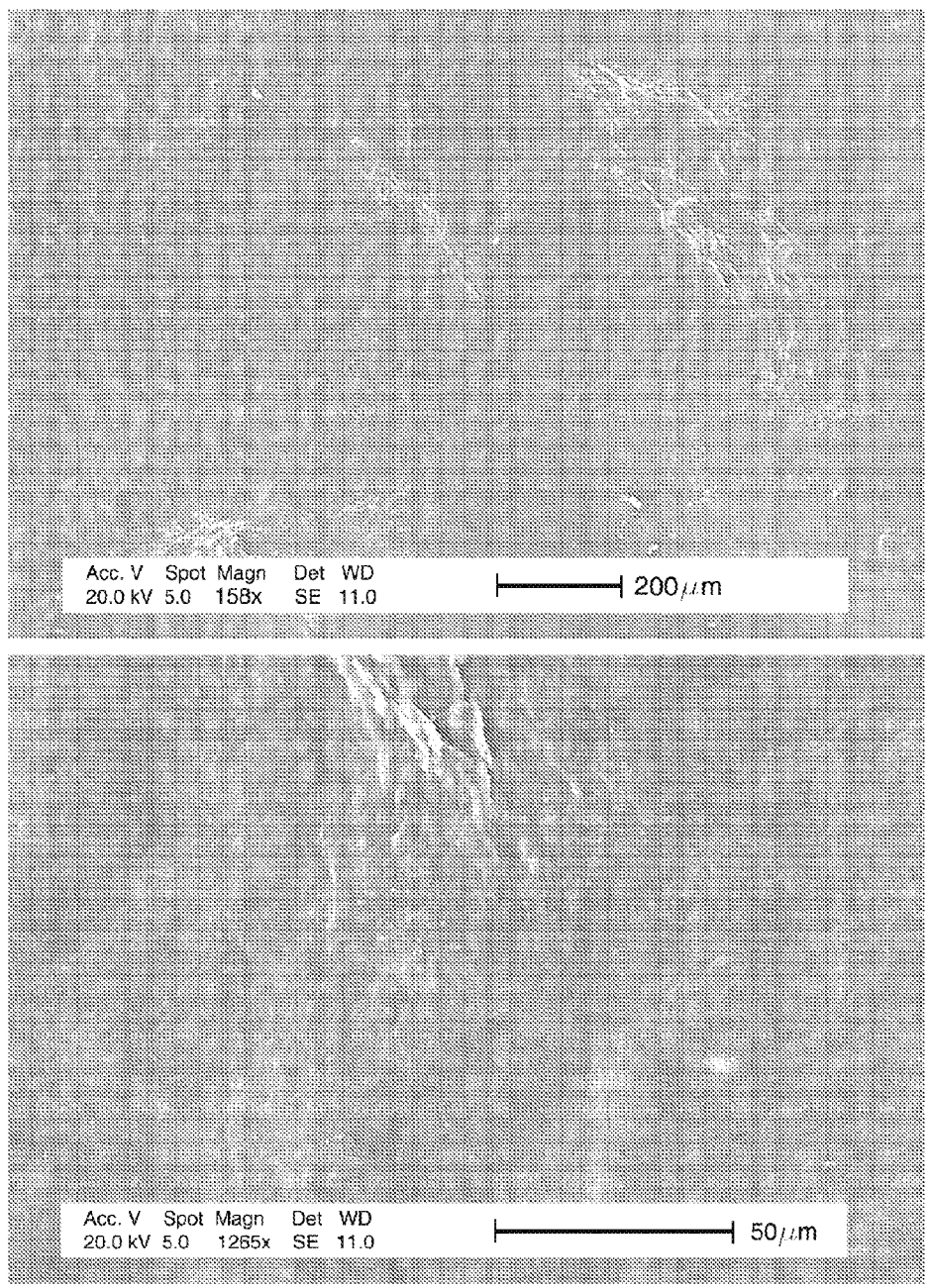

FIG. 4 depicts the $^{13}$C NMR spectra of reconstituted pure chitin dissolved in [C$_2$mim]OAc. NMR samples were prepared by first dissolving reconstituted pure chitin in [C$_2$mim]OAc at 100° C. for 1 hour resulting in a clear solution. DMSO-d6 was then added to make a 5% chitin solution for analysis.

The chitin signals at 101.1 (C-1), 80.0 (C-4), 75.2 (C-5), 72.2 (C-3), 63.0 (C-6), and 59.2 (C-2) ppm, are all well resolved. The two signals at 75.2 and 72.2 ppm as well resolved peaks, indicate the existence of α-chitin and are attributed to the different configurations of C3 and C5 resulting from hydrogen bonds. The signals at 169.1 and 21.9 ppm are from carbonyl and methyl carbons of acetate groups in acetylamine, respectively. All chemical shifts are comparable to the values reported in the literature, in which either concentrated HCl or NaOH with deuterated water were used as solvents, or when solid state $^{13}$C NMR was applied. All other large signals can be attributed to the [C$_2$mim]OAc and DMSO-d6.

Tables IV and V summarize the tensile strength of various polymers prepared by the disclosed process.

TABLE IV

| Example No. | Conc. of spinning solution | Composition | Ultimate Stress (MPa) | Failure Strain (%) | Young's Modulus (GPa) |
|---|---|---|---|---|---|
| 2 | 7.14 wt % | 100% chitin | 107.7 ± 17.1 | 5.2 ± 0.8 | 4.3 ± 0.7 |
| 3 | 3.67 wt % | 100% chitin | 289.9 ± 31.5 | 9.1 ± 2.9 | 4.3 ± 0.7 |
| 3 | 4.2 wt % | 100% chitin | 144.1 ± 41.6 | 7.5 ± 1.2 | 8.2 ± 3.2 |
| | 10.3 wt % total biomass | Chitin:Cellulose = 1:15.8, (wt/wt) | 159.0 ± 31.8 | 5.4 ± 1.8 | 6.6 ± 1.2 |
| Comparative Example 7 | 11.5 wt % of cellulose | 100% cellulose | 85.5 ± 14.0 | 8.0 ± 1.8 | 6.0 ± 1.5 |

TABLE V

| | Conc. of total biomass (wt. %) | Ultimate stress (MPa) | Failure strain (%) | Young's modulus (GPa) |
|---|---|---|---|---|
| PG chitin fiber | 3.9[a] | 260.1 ± 29.2 | 1.9 ± 0.0 | 15.3 ± 1.7 |
| DMSO pre-treatment | 4.8[a] | 299.4 ± 98.2 | 3.6 ± 0.0 | 9.1 ± 7.1 |
| | 7.1[a] | 107.7 ± 17.1 | 5.2 ± 0.8 | 4.3 ± 0.7 |
| PG chitin fiber | 3.7[b] | 271.8 ± 3.8 | 10.4 ± 2.6 | 10.3 ± 2.2 |
| DMSO co-solvent | 4.2[b] | 121.5 ± 19.6 | 7.0 ± 1.1 | 6.5 ± 1.8 |
| PG chitin fiber direct extraction | 3.4 | 80.1 ± 9.5 | 5.0 ± 0.9 | 4.7 ± 0.8 |
| Shrimp shells fiber direct extraction | 3.8 | 133.8 ± 12.9 | 3.3 ± 0.3 | 8.6 ± 1.6 |
| | 3.2[b] | 196.1 ± 15.3 | 3.6 ± 1.4 | 12.1 ± 4.4 |
| Pure chitin/ cellulose fiber | 11.5[c] | 240.8 ± 11.5 | 6.0 ± 0.8 | 9.1 ± 0.6 |
| | 11.5[d] | 224.5 ± 3.1 | 4.4 ± 0.4 | 9.0 ± 0.3 |
| Shrimp shell/ cellulose fiber | 10.0[e] | 173.3 ± 24.8 | 6.3 ± 1.0 | 7.1 ± 1.2 |

[a]The solution weight does not include the weight of DMSO.
[b]The solution weight includes weight of DMSO (4.6 wt %).
[c]Pure chitin/cellulose = 1:2 (wt/wt).
[d]Pue chitin/cellulose = 3:4 (wt/wt)
[e]Shrimp shells/cellulose = 1:4.3 (wt/wt)

These results show that the produced dry chitin fiber from either Example 2 or Example 3 yields a tensile strength of 107.7-289.9 MPa, breaking elongation of 5.2-9.1%, with Young's modulus of 4.3-11.3 GPa, suggesting this chitin fiber is stronger than a cellulose fiber (85.5 MPa) produced by the disclosed process, or comparable with the pure cellulose fiber prepared by the same cellulose concentration and same method in literature (129 MPa) (See Sukhanova T. E. et al. Vysokomol. Soedin. Ser. B 31 (1989) 381; Chem. Abstr. 111 (20): 175985n). However, our chitin fibers are weaker than other chitin fibers prepared by DMAc/LiCl (390 MPa with 3% elongation and 1 GPa initial modulus), or by TCA system (e.g. 706 MPa with a 13% breaking elongation) as reported in the literature. Our shrimp shell/cellulose composite fiber (159 MPa) is stronger than the cellulose fiber (85.5 or 129 MPa). Fiber production can be optimized to reach the target property.

In addition, when DMSO (5 wt %) is added to the biomass/ionic liquid solution, although the amount of chitin is low, for example 2.8 wt %, fibers can be pulled from this solution directly. At a concentration of from about 0.68 wt % to about 0.94 wt %, (based on the fact that shrimp shell comprise approximately 27.2 wt % of chitin), this process provides a method of directly providing fibers from a source of chitin having a low amount of chitin.

FIG. 1 depicts the IR spectra of polymer films prepared by the disclosed process. Spectrum 1A depicts the IR spectrum of a polymer film comprising chitin derived from shrimp shells according to Example 1. Spectrum 1B depicts the IR spectrum of a polymer film comprising practical grade chitin according to Example 2. Spectrum 1C depicts the IR spectrum of a polymer film comprising practical grade chitin according to Example 3. The IR spectra of FIGS. 1A, 1B, and 1C have almost identical IR plots. The IR analysis in FIG. 1 confirms that the only component in the fibers is chitin, for example, for the film produced by Example 2, no peaks appeared at 1436 and 1406 cm$^{-1}$ indicating no residue DMSO left in the film.

Figure 2:
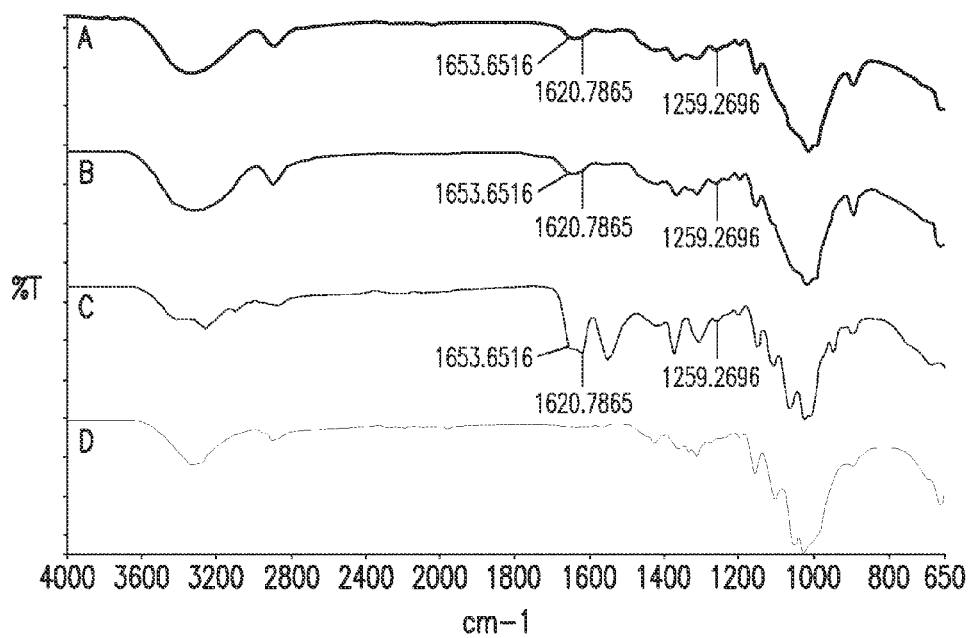
FIG. 2 is the IR spectra of composite polymer fibers with fibers made from a single polymer. Spectrum 2A depicts a polymer comprising chitin/cellulose (3:4 wt/wt). Spectrum 2B depicts a polymer comprising chitin derived from shrimp shell/cellulose (1:15.8 wt/wt). Spectrum 2C depicts a polymer comprising chitin. Spectrum 2D depicts a polymer comprising cellulose.

FIG. 2 depicts the comparison of the IR spectra of composite polymer fibers with fibers made from a single polymer. Spectrum 2A depicts a polymer comprising chitin/cellulose (3:4 wt/wt). Spectrum 2B depicts a polymer comprising chitin derived from shrimp shell/cellulose (1:15.8 wt/wt). Spectrum 2C depicts a polymer comprising chitin. Spectrum 2D depicts a polymer comprising cellulose. The IR spectra in FIG. 2 show the existence of peaks of 1654 and 1621 cm$^{-1}$, which are peaks due to C=O stretching mode of singly hydrogen-bonded to NH and doubly hydrogen-bonded to both NH and C(6)OH, respectively, in the composite chitin/cellulose and shrimp shell/cellulose films confirming the existence of chitin in the composite films.

Figure 3:
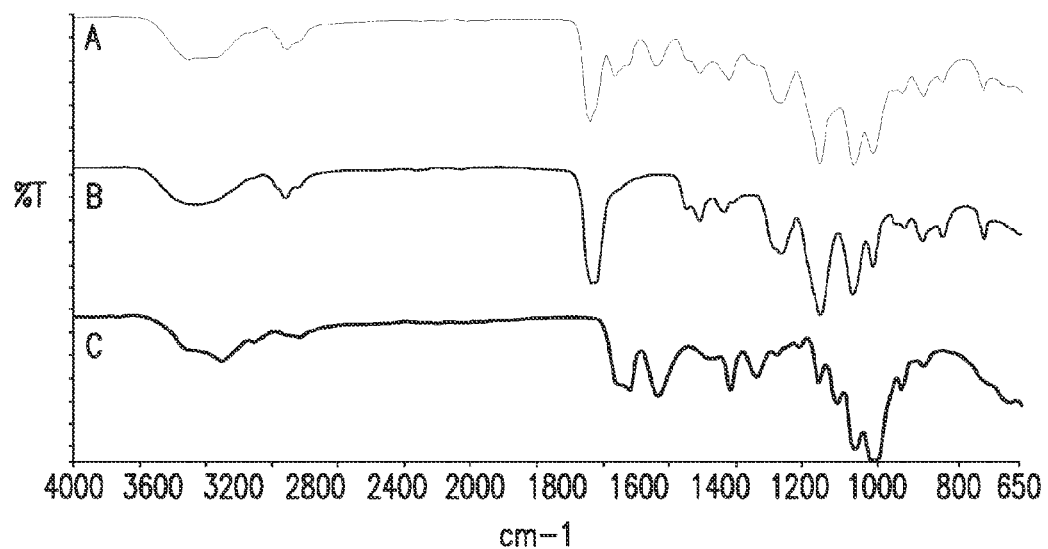
FIG. 3 is the IR spectra obtained from fibers comprising a blended polymer comprising 2:1 Poly-HEMA/chitin (Spectrum 3A), pure Poly-HEMA (Spectrum 3B), and pure chitin (Spectrum 3C).

FIG. 3 depicts the comparison of IR spectra obtained from fibers comprising pure Poly-HEMA (3B), pure chitin (3C) and a blended polymer comprising 2:1 Poly-HEMA/chitin (3A). Both poly-HEMA and pure chitin peaks were found in the blend (3A), which confirms the blend structure is formed. Peaks at 1714 and 2942 cm$^{-1}$ are stretching of C=O, and alkyl from poly-HEMA. Peak at 3257, 3099, 1651, 1622, 1550 cm$^{-1}$ are stretching of N—H (asymmetric), N—H (symmetric), amide I (singly H-bond), amide I (doubly H-bond), and amide II from chitin, respectively.

Table VI provides a comparison of the EDS analysis of reconstituted chitin obtained by various methods versus control.

TABLE VI

| Element | Weight % | Atomic % | Element | Weight % | Atomic % |
|---|---|---|---|---|---|
| | Practical grade chitin | | | Reconstituted practical grade chitin by the method of Example 2 | |
| C K | 31.01 ± 1.06 | 36.56 ± 1.17 | C K | 47.79 ± 3.30 | 55.24 ± 3.37 |
| N K | 26.63 ± 0.79 | 26.93 ± 0.87 | N K | 4.98 ± 1.02 | 4.94 ± 1.05 |
| O K | 40.34 ± 0.23 | 35.71 ± 0.29 | O K | 44.05 ± 2.35 | 38.25 ± 2.35 |
| Si K | 0.43 ± 0.01 | 0.22 ± 0.01 | Si K | 3.19 ± 0.06 | 1.58 ± 0.02 |
| Cl K | 0.75 ± 0.04 | 0.30 ± 0.01 | Total | 100 | 100 |
| Ca K | 0.85 ± 0.06 | 0.30 ± 0.02 | | | |
| Total | 100.01 | 100.00 | | | |
| | Reconstituted practical grade chitin by using DMSO as co-solvent | | | Reconstituted practical grade chitin using microwave radiation heating | |
| C K | 48.01 ± 0.15 | 55.55 ± 0.13 | C K | 31.08 ± 0.59 | 36.36 ± 0.65 |
| N K | 5.21 ± 0.50 | 5.15 ± 0.47 | N K | 26.13 ± 0.76 | 26.21 ± 0.78 |
| O K | 43.77 ± 0.57 | 37.76 ± 0.15 | O K | 42.36 ± 0.30 | 37.21 ± 0.21 |
| Si K | 3.01 ± 0.07 | 1.54 ± 0.04 | Si K | 0.44 ± 0.20 | 0.22 ± 0.10 |
| Total | 100.00 | 100.00 | Total | 100.00 | 100.00 |

Table VII shows the compositional analysis (wt %) of chitin and crustacean shells.

TABLE VII

| | Pure chitin | Practical grade chitin | Shrimp shells | Crustacean shells |
|---|---|---|---|---|
| Moisture content | 5.5 | 5.3 | 8.7 | N/A |
| Ash content | 0.3 | 2.2 | 34.5 | 30-50 |
| Chitin content | 81.8 | 78.9 | 27.2 | 13-41 |
| Chitin content of the reconstituted chitin from dissolution of each chitin source | 87.1 | 84.7 | 81.1 | N/A |

Table VIII is a comparison of the thermostability of [C$_2$mim]OAc under various conditions.

TABLE VIII

| | Mass lost in 15 h | Mass lost in 19 h | Mass lost in 24 h |
|---|---|---|---|
| a. 100° C. in N$_2$ | 1.2% | 1.3% | 1.4% |
| b. 100° C. in air | 1.2% | 1.4% | 1.7% |
| c. 110° C. in N$_2$ | 2.8% | 3.1% | 3.5% |
| d. 110° C. in air | 12.2% | 14.3% | 16.8% |
| e. 130° C. in air | 21.2% | 26.5% | 32.8% |

Table IX is a comparison of shrimp shells dissolution in air or under nitrogen, and reconstitution of chitin from the solution by using DI water as coagulant.

TABLE IX

| | Dissolution in air$^a$ | Dissolution under N$_2$$^a$ |
|---|---|---|
| Amount of chitin dissolved in 10 g [C$_2$mim]OAc | 0.46 g | 0.43 g |
| Percent dissolved$^b$ | 4.6% | 4.3% |
| Reconstituted chitin from shrimp shells | 0.08 g | 0.08 g |
| Chitin reconstitution yield$^c$ | 52.1% | 55.5% |

$^a$Experimental details: 1 g of shrimp shells was mixed with 10 g [C$_2$mim]OAc, the reaction happened at 100° C. for 19 h under the target environment.
$^b$Calculated by eq. 1.
$^c$Calculated by eq. 2, where chitin content for shrimp shells and reconstituted chitin from shrimp shells are 27.2 wt % and 81.1%, individually, based on our result shown in Table VII.

Table X is a comparison of the chemical composition observed in the EDS analysis for chitinous samples and the chitin reconstituted from them.

TABLE X

| Element | Weight % | Atomic % | Element | Weight % | Atomic % |
|---|---|---|---|---|---|
| | Pure chitin | | | Reconstituted pure chitin | |
| C K | 30.06 ± 1.06 | 35.18 ± 1.12 | C K | 29.72 ± 0.47 | 34.78 ± 0.51 |
| N K | 27.09 ± 0.08 | 27.18 ± 0.01 | N K | 27.80 ± 0.42 | 27.90 ± 0.45 |
| O K | 42.86 ± 1.12 | 37.65 ± 1.12 | O K | 42.49 ± 0.04 | 37.33 ± 0.06 |
| Total | 100.00 | 100.00 | Total | 100.00 | 100.00 |
| | Practical grade chitin | | | Reconstituted practical grade chitin | |
| C K | 31.01 ± 1.06 | 36.56 ± 1.17 | C K | 31.08 ± 0.59 | 36.36 ± 0.65 |
| N K | 26.63 ± 0.79 | 26.93 ± 0.87 | N K | 26.13 ± 0.76 | 26.21 ± 0.78 |
| O K | 40.34 ± 0.23 | 35.71 ± 0.29 | O K | 42.36 ± 0.30 | 37.21 ± 0.21 |
| Si K | 0.43 ± 0.01 | 0.22 ± 0.01 | Si K | 0.44 ± 0.20 | 0.22 ± 0.10 |
| Cl K | 0.75 ± 0.04 | 0.30 ± 0.01 | Total | 100.00 | 100.00 |
| Ca K | 0.85 ± 0.06 | 0.30 ± 0.02 | | | |
| Total | 100.01 | 100.00 | | | |
| | Shrimp shells | | | Reconstituted shrimp shell chitin | |
| C K | 22.55 ± 0.79 | 28.95 ± 0.74 | C K | 30.22 ± 0.15 | 35.54 ± 0.13 |
| N K | 27.31 ± 0.54 | 30.06 ± 0.31 | N K | 25.14 ± 0.50 | 25.35 ± 0.47 |
| O K | 37.20 ± 0.25 | 35.85 ± 0.57 | O K | 43.82 ± 0.57 | 38.20 ± 0.15 |
| Si K | 0.23 ± 0.04 | 0.13 ± 0.02 | Si K | 0.83 ± 0.07 | 0.42 ± 0.04 |
| Ca K | 12.19 ± 0.98 | 4.69 ± 0.42 | Total | 100.00 | 99.50 |
| Mg K | 0.53 ± 0.06 | 0.33 ± 0.04 | | | |
| Total | 99.99 | 100.00 | | | |

Table XI is from microwave heating on practical grade chitin dissolution in [C$_2$mim]OAc.

TABLE XI

|  | Heating for 2 min | Heating for 4 min |
|---|---|---|
| Amount dissolved, g | 0.04 | 0.04 |
| Percent dissolved, % | 100 | 100 |
| Amount regenerated, g | 0.0264 | 0.0214 |
| Chitin reconstitution yield, % | 70.85 | 57.43 |

Table XII is a comparison of complete dissolution of chitinous samples in [$C_2$mim]OAc.

TABLE XII

|  | Maximum solubility chitinous sample dissolved, mass % | Time to reach complete dissolution | Chitin reconstitution yield, % |
|---|---|---|---|
| Pure chitin[a] | 17.5 | 4 h | 98.3 |
| Practical grade chitin[b] | 0.8 | 15 d | 14.1 |
| Shrimp shells[b] | 1.7 | 29 d | 25.4 |

[a]Pure chitin was dissolved in 2 g IL;
[b]Chitin samples were dissolved in 10 g IL.

Table XIII is a percent chitin dissolved in [$C_2$mim]OAc at 100° C. for 19 h and reconstitution yield of chitin coagulated with water

TABLE XIII

|  | Percent Dissolved, % | Chitin reconstitution yield, wt % |
|---|---|---|
| Pure chitin[a] | 80.0 | 98.1 |
| Practical grade chitin[b] | 15.2 | 64.8 |
| Shrimp shells[b] | 46.0 (10.2[c]) | 52.1 (60.8[c]) |

[a]0.5 g pure chitin was mixed with 2 g IL;
[b]1 g chitin sample was mixed with 10 g IL;
[c]Result of a study conducted at room temperature for 4 months with occasional stirring.

Table XIV shows the degree of acetylation (DA) and crystallinity of chitinous samples. Table XV shows the thermostability of chitins. Table XVI shows the melting temperature of chitins.

TABLE XIV

|  | DA, % | CrI, % |
|---|---|---|
| Pure chitin | 91.35 | 70.7 |
| Reconstituted pure chitin | 87.99 | 70.9 |
| Practical grade chitin | 80.43 | 68.2 |
| Reconstituted practical grade chitin | 80.61 | 64.0 |
| Reconstituted shrimp shells | 83.29 | 70.9 |

TABLE XV

|  | Pure chitin | Chitin reconstituted from pure chitin | Practical grade chitin | Reconstituted practical grade chitin | Reconstituted shrimp shell chitin |
|---|---|---|---|---|---|
| $1^{st} T_{onset}$ (° C.) | 223.63 | 276.52 | 278.97 | 296.67 | 298.66 |
| $1^{st} T_{5\% onset}$ (° C.) | 181.33 | 248.19 | 225.69 | 237.33 | 237.44 |
| $2^{nd} T_{onset}$ (° C.) | 450.46 | 457.14 | 397.65 | 462.90 | 479.36 |
| Char (wt %) | 6.66 | 5.89 | 2.23 | 0.81 | 1.39 |

TABLE XVI

|  | Pure chitin | Reconstituted pure chitin | Practical grade chitin | Reconstituted practical grade chitin | Reconstituted shrimp shell chitin |
|---|---|---|---|---|---|
| $T_m$ (° C.) | 177.94 | 133.97 | 175.35 | 129.98 | 195.51 |

Table XVII shows the relative viscosities of chitin in [$C_2$mim]OAc at 35° C.

TABLE XVII

| Samples | Conc. of chitin in [$C_2$mim]OAc (%) | Total heating time (sec)[a] | Relative Viscosity ($\eta_{rel}$)[b] |
|---|---|---|---|
| [$C_2$mim]OAc | 0 | N/A | 1 |
| Pure chitin | 0.21 | 120 | 1.13 |
| PG-chitin | 0.21 | 120 | 2.02 |
| Shrimp shells | 0.21 | 120 | 1.55 |
| Rec. pure chitin | 0.21 | 60 | 1.10 |
| Rec. PG-chitin | 0.21 | 60 | 1.28 |
| Rec. shrimp shell chitin | 0.21 | 60 | 1.43 |

[a]Reconstitued chitin samples are easier to be completely dissolved than unprocessed chitin, thus less heating time was used.
[b]($\eta_{rel}$) = flow time of the solution/flow time of the solvent ([$C_2$mim]OAc]).

Table XVIII contains data related to dissolution and recovery of chitin from IL solution and resulting fiber properties.

TABLE XVIII

| Samples | Avail. Chitin Recovered (%)[a] | Relative Viscosity ($\eta_{rel}$)[b] | Conc. To pull fiber (wt. %) | Fiber thickness (mm)[c] | Ultimate stress (MPa)[d] | Failure strain (%)[d] | Young's modulus (GPa)[d] |
|---|---|---|---|---|---|---|---|
| Pure chitin | 40.2 | 1.13 | —[e] | | | | |
| PG-chitin | 87.4 | 2.02 | 3.4 | 0.13(3) | 80(9) | 5.0(9) | 4.7(8) |
| Shrimp shells | 94.0 | 1.55 | 3.8 | 0.06(1) | 133(13) | 3.3(3) | 8.6(2) |
| Rec. pure chitin[f] | | 1.10 | —[e] | | | | |
| Rec. PG-chitin[f] | | 1.28 | 4.0 | 0.09(1) | 132(10) | 6.9(4) | 5.3(5) |
| Rec. shrimp shells[f] | | 1.43 | 2.1 | 0.07(1) | 237(26) | 13(4) | 10(1) |

TABLE XVIII-continued

| Samples | Avail. Chitin Recovered (%)[a] | Relative Viscosity ($\eta_{rel}$)[b] | Conc. To pull fiber (wt. %) | Fiber thickness (mm)[c] | Ultimate stress (MPa)[d] | Failure strain (%)[d] | Young's modulus (GPa)[d] |
|---|---|---|---|---|---|---|---|
| Cellulose MCC[g] | | | 11.5 | 0.15(3) | 129(17) | 24(3) | |
| Cellulose pulp[h] | | | 4.3 | 0.07(1) | 217(17) | 13(0) | |

[a]See ESI eq. 2.
[b]$\eta_{rel} = t_s/t_0$ ($t_s$: Flow time of solution, $t_0$: flow time of IL (35° C.; same concentrations).
[c]Avg. five samples.
[d]Avg. three fibers.
[e]Fibers could not be formed.
[f]Second dissolution.
[g]Microcrystalline cellulose of DP = 270.[18]
[h]Kraft pulp of degree of polymerization (DP) = 1056.

Adjunct Ingredients

The following are non-limiting examples of adjunct ingredient suitable for use in the disclosed process.

When pharmaceutical activity is a desired property of the disclosed fibers, films, or beads, one or more of the adjunct ingredients can be a pharmaceutical active. It is not intended that the category be limited by the specific examples. Those of ordinary skill in the art will be able to readily identify those pharmaceutical actives that can be used in the disclosed methods and compositions. For example, one can identify a compound with a given property or activity by consulting various sources, such as the Merck Index (13th Edition, Wiley, 2001), The United States Pharmacopeia-National Formulary (USP-NF), and the FDA's Orange book, which are each incorporated by reference herein at least for their teachings of pharmaceutical actives. Once a compound with a desired property is identified, the skilled artisan can determine the manner in which the compound can be combined with the chitin, the regenerated chitin, the admixture of chitin and one or more naturally occurring or synthetic polymers. Such determinations can be performed based on the compound's structure, which can readily be determined by consulting the sources mentioned herein or experimentally. Knowing a compound's structure can readily reveal at what step in the process the adjunct ingredient can be added. Those of ordinary skill in the art will recognize numerous other compounds that fall within the categories and that are useful according to the disclosed films, fibers, beads, compositions and processes.

Some specific examples of pharmaceutical actives that can be used in the disclosed process or as a component of a resulting film, fiber, or bead include, but are not limited to, aspirin, LIBRIUM™, isoniazid, penicillin, PRONTOSIL™, cisplatin, 6-mercaptopurine, RITUXAN™, TAXOL™, phenobarbital, PROZAC™, ALLEGRA™, VIOXX™, quinine, ivermectin, L-dopa, THORAZINE™, salvarsan, TAGAMET™, AZT, crixivan, salbutamol, digoxin, fluride, LOVASTATIN™, erythropoietin, hydrocortisone, insulin, oral contraceptives, oxytocin, PREMARIN™, RU-486, thyroxine, thalidomide, cyclosporine, fentanyl, methadone, morphine, botox, vitamins, FOSAMAX™, RITALIN™, and VIAGRA™, including ionic derivatives thereof.

Other examples of pharmaceutical actives include, but are not limited to, pantoprazole, sold under the trade names PROTONIX™ and PANTOZOL™, and rabeprazole, sold under the trade names ACIPHEX™ and PARIET™, which are used to treat gastrointestinal disorders. Risedronate, sold under the trade name ACTONEL™, and alendronate, sold under the trade name FOSAMAX™, are used to treat osteoporosis and are further examples of suitable adjunct ingredients. Further examples include losartan, sold under the trade names NU-LOTAN™, COZAAR™, and HYZAAR™, and fosinopril, sold under the trade name MONOPRIL™, Atorvastatin, sold under the trade name LIPITOR™, and pravastatin, sold under the trade name PRAVACHOL™, are used to treat cholesterol and montelukast, which is used to treat asthma and is sold under the trade name SINGULAIR™.

The following are further examples of pharmaceutical actives that are suitable for use in forming the disclosed films, fibers, or beads. Prostaglandin $E_2$, Prostaglandin $F2_A$, Sulprostone, Cetapril, Benzaepril, Captopril, Methyl hexaneamine, Synephrine, Isoetharine, Methoxyphenamine, Tamsulosin, Tolazoline, Bufuralol, Nadoxolol, Acetylsalicylic acid, ammonium salicylate, Buthalital Sodium, Thiopental Sodium, and Isobutyl p-Aminobenzoate.

Further examples of pharmaceutical actives that can be used as adjunct ingredients include the following. Adrenergic: adrenalone, amidephrine mesylate, apraclonidine hydrochloride, brimonidine tartrate, dapiprazole hydrochloride, deterenol hydrochloride, dipivefrin, dopamine hydrochloride, ephedrine sulfate, epinephrine, epinephrine bitartrate, epinephryl borate, esproquin hydrochloride, etafedrine hydrochloride, hydroxyamphetamine hydrobromide, levonordefrin, mephentermine sulfate, metaraminol bitartrate, metizoline hydrochloride, naphazoline hydrochloride, norepinephrine bitartrate, oxidopamine, oxymetazoline hydrochloride, phenylephrine hydrochloride, phenylpropanolamine hydrochloride, phenylpropanolamine polistirex, prenalterol hydrochloride, propylhexedrine, pseudoephedrine hydrochloride, tetrahydrozoline hydrochloride, tramazoline hydrochloride, xylometazoline hydrochloride.

Adrenocortical steroid: ciprocinonide, desoxycorticosterone acetate, desoxycorticosterone pivalate, dexamethasone acetate, fludrocortisone acetate, flumoxonide, hydrocortisone hemisuccinate, methylprednisolone hemisuccinate, naflocort, procinonide, timobesone acetate, tipredane.

Adrenocortical suppressant: aminoglutethimide, trilostane.

Alcohol deterrent: disulfuram.

Aldosterone antagonist: canrenoate potassium, canrenone, dicirenone, mexrenoate potassium, prorenoate potassium, spironolactone.

Amino acid: alanine, aspartic acid, cysteine hydrochloride, cystine, histidine, isoleucine, leucine, lysine, lysine acetate, lysine hydrochloride, methionine, phenylalanine, proline, serine, threonine, tryptophan, tyrosine, valine.

Ammonia detoxicant: arginine: arginine glutamate, arginine hydrochloride.

Anabolic: bolandiol dipropionate, bolasterone, boldenone undecylenate, bolenol, bolnantalate, ethylestrenol, methenolone acetate, methenolone enanthate, mibolerone, nandrolone cyclotate, norbolethone, pizotyline, quinbolone, stenbolone acetate, tibolone, zeranol.

Analeptic: modafinil.

Analgesic: acetaminophen, alfentanil hydrochloride, aminobenzoate potassium, aminobenzoate sodium, anidoxime, anileridine, anileridine hydrochloride, anilopam hydrochloride, anirolac, antipyrine, aspirin, benoxaprofen, benzydamine hydrochloride, bicifadine hydrochloride, brifentanil hydrochloride, bromadoline maleate, bromfenac sodium, buprenorphine hydrochloride, butacetin, butixirate, butorphanol, butorphanol tartrate, carbamazepine, carbaspirin calcium, carbiphene hydrochloride, carfentanil citrate, ciprefadol succinate, ciramadol, ciramadol hydrochloride, clonixeril, clonixin, codeine, codeine phosphate, codeine sulfate, conorphone hydrochloride, cyclazocine, dexoxadrol hydrochloride, dexpemedolac, dezocine, diflunisal, dihydrocodeine bitartrate, dimefadane, dipyrone, doxpicomine hydrochloride, drinidene, enadoline hydrochloride, epirizole, ergotamine tartrate, ethoxazene hydrochloride, etofenamate, eugenol, fenoprofen, fenoprofen calcium, fentanyl citrate, floctafenine, flufenisal, flunixin, flunixin meglumine, flupirtine maleate, fluproquazone, fluradoline hydrochloride, flurbiprofen, hydromorphone hydrochloride, ibufenac, indoprofen, ketazocine, ketorfanol, ketorolac tromethamine, letimide hydrochloride, levomethadyl acetate, levomethadyl acetate hydrochloride, levonantradol hydrochloride, levorphanol tartrate, lofemizole hydrochloride, lofentanil oxalate, lorcinadol, lomoxicam, magnesium salicylate, mefenamic acid, menabitan hydrochloride, meperidine hydrochloride, meptazinol hydrochloride, methadone hydrochloride, methadyl acetate, methopholine, methotrimeprazine, metkephamid acetate, mimbane hydrochloride, mirfentanil hydrochloride, molinazone, morphine sulfate, moxazocine, nabitan hydrochloride, nalbuphine hydrochloride, nalmexone hydrochloride, namoxyrate, nantradol hydrochloride, naproxen, naproxen sodium, naproxol, nefopam hydrochloride, nexeridine hydrochloride, noracymethadol hydrochloride, ocfentanil hydrochloride, octazamide, olvanil, oxetorone fumarate, oxycodone, oxycodone hydrochloride, oxycodone terephthalate, oxymorphone hydrochloride, pemedolac, pentamorphone, pentazocine, pentazocine hydrochloride, pentazocine lactate, phenazopyridine hydrochloride, phenyramidol hydrochloride, picenadol hydrochloride, pinadoline, pirfenidone, piroxicam olamine, pravadoline maleate, prodilidine hydrochloride, profadol hydrochloride, propiram fumarate, propoxyphene hydrochloride, propoxyphene napsylate, proxazole, proxazole citrate, proxorphan tartrate, pyrroliphene hydrochloride, remifentanil hydrochloride, salcolex, salethamide maleate, salicylamide, salicylate meglumine, salsalate, sodium salicylate, spiradoline mesylate, sufentanil, sufentanil citrate, talmetacin, talniflumate, talosalate, tazadolene succinate, tebufelone, tetrydamine, tifurac sodium, tilidine hydrochloride, tiopinac, tonazocine mesylate, tramadol hydrochloride, trefentanil hydrochloride, trolamine, veradoline hydrochloride, verilopam hydrochloride, volazocine, xorphanol mesylate, xylazine hydrochloride, zenazocine mesylate, zomepirac sodium, zucapsaicin.

Androgen: fluoxymesterone, mesterolone, methyltestosterone, nandrolone decanoate, nandrolone phenpropionate, nisterime acetate, oxandrolone, oxymetholone, silandrone, stanozolol, testosterone, testosterone cypionate, testosterone enanthate, testosterone ketolaurate, testosterone phenylacetate, testosterone propionate, trestolone acetate.

Anesthesia, adjunct to: sodium oxybate.

Anesthetic: aliflurane, benoxinate hydrochloride, benzocaine, biphenamine hydrochloride, bupivacaine hydrochloride, butamben, butamben picrate, chloroprocaine hydrochloride, cocaine, cocaine hydrochloride, cyclopropane, desflurane, dexivacaine, diamocaine cyclamate, dibucaine, dibucaine hydrochloride, dyclonine hydrochloride, enflurane, ether, ethyl chloride, etidocaine, etoxadrol hydrochloride, euprocin hydrochloride, fluoroxene, halothane, isobutamben, isoflurane, ketamine hydrochloride, levoxadrol hydrochloride, lidocaine, lidocaine hydrochloride, mepivacaine hydrochloride, methohexital sodium, methoxyflurane, midazolam hydrochloride, midazolam maleate, minaxolone, nitrous oxide, norflurane, octodrine, oxethazaine, phencyclidine hydrochloride, pramoxine hydrochloride, prilocalne hydrochloride, procaine hydrochloride, propanidid, proparacaine hydrochloride, propofol, propoxycaine hydrochloride, pyrrocaine, risocaine, rodocaine, roflurane, salicyl alcohol, sevoflurane, teflurane, tetracaine, tetracaine hydrochloride, thiamylal, thiamylal sodium, thiopental sodium, tiletamine hydrochloride, zolamine hydrochloride.

Anorectic compounds including dexfenfluramine.

Anorexic: a minorex, amphecloral, chlorphentermine hydrochloride, clominorex, clortermine hydrochloride, diethylpropion hydrochloride, fenfluramine hydrochloride, fenisorex, fludorex, fluminorex, levamfetamine succinate, mazindol, mefenorex hydrochloride, phenmetrazine hydrochloride, phentermine, sibutramine hydrochloride.

Antagonist: atipamezole, atosiban, bosentan, cimetidine, cimetidine hydrochloride, clentiazem maleate, detirelix acetate, devazepide, donetidine, etintidine hydrochloride, famotidine, fenmetozole hydrochloride, flumazenil, icatibant acetate, icotidine, isradipine, metiamide, nadide, nalmefene, nalmexone hydrochloride, naloxone hydrochloride, naltrexone, nilvadipine, oxilorphan, oxmetidine hydrochloride, oxmetidine mesylate, quadazocine mesylate, ranitidine, ranitidine bismuth citrate, ranitidine hydrochloride, sufotidine, teludipine hydrochloride, tiapamil hydrochloride, tiotidine, vapiprost hydrochloride, zaltidine hydrochloride.

Anterior pituitary activator: epimestrol.

Anterior pituitary suppressant: danazol.

Anthelmintic: albendazole, anthelmycin, bromoxanide, bunamidine hydrochloride, butonate, cambendazole, carbantel lauryl sulfate, clioxanide, closantel, cyclobendazole, dichlorvos, diethylcarbamazine citrate, dribendazole, dymanthine hydrochloride, etibendazole, fenbendazole, furodazole, hexylresorcinol, mebendazole, morantel tartrate, niclosamide, nitramisole hydrochloride, nitrodan, oxantel pamoate, oxfendazole, oxibendazole, parbendazole, piperamide maleate, piperazine, piperazine citrate, piperazine edetate calcium, proclonol, pyrantel pamoate, pyrantel tartrate, pyrvinium pamoate, rafoxanide, stilbazium iodide, tetramisole hydrochloride, thiabendazole, ticarbodine, tioxidazole, triclofenol piperazine, vincofos, zilantel.

Anti-acne: adapalene, erythromycin salnacedin, inocoterone acetate, accutane.

Anti-adrenergic: acebutolol, alprenolol hydrochloride, atenolol, bretylium tosylate, bunolol hydrochloride, carteolol hydrochloride, celiprolol hydrochloride, cetamolol hydrochloride, ciprolol hydrochloride, dexpropranolol hydrochloride, diacetolol hydrochloride, dihydroergotamine mesylate, dilevalol hydrochloride, esmolol hydrochloride, exaprolol hydrochloride, fenspiride hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, phentolamine mesylate, practolol, propranolol hydrochloride, proroxan hydrochloride, solypertine taitrate, sotalol hydrochloride, timolol, timolol maleate, tiprenolol hydrochloride, tolamolol, zolertine hydrochloride.

Anti-allergic: amlexanox, astemizole, azelastine hydrochloride, eclazolast, minocromil, nedocromil, nedocromil calcium, nedocromil sodium, nivimedone sodium, pemirolast potassium, pentigetide, pirquinozol, poisonoak extract, probicromil calcium, proxicromil, repirinast, tetrazolast meglumine, thiazinamium chloride, tiacrilast, tiacrilast sodium, tiprinast meglumine, tixanox.

Anti-amebic: berythromycin, bialamicol hydrochloride, chloroquine, chloroquine hydrochloride, chloroquine phosphate, clamoxyquin hydrochloride, clioquinol, emetine hydrochloride, iodoquinol, paromomycin sulfate, quinfamide, symetine hydrochloride, teclozan, tetracycline, tetracycline hydrochloride.

Anti-androgen: benorterone, cioteronel, cyproterone acetate, delmadinone acetate, oxendolone, topterone, zanoterone.

Anti-anemic: epoetin alfa, epoetin beta, ferrous sulfate, dried, leucovorin calcium.

Anti-anginal: amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen, verapamil hydrochloride.

Anti-anxiety agent: adatanserin hydrochloride, alpidem, binospirone mesylate, bretazenil, glemanserin, ipsapirone hydrochloride, mirisetron maleate, ocinaplon, ondansetron hydrochloride, panadiplon, pancopride, pazinaclone, serazapine hydrochloride, tandospirone citrate, zalospirone hydrochloride.

Anti-arthritic: lodelaben.

Anti-asthmatic: ablukast, ablukast sodium, azelastine hydrochloride, bunaprolast, cinalukast, crornitrile sodium, cromolyn sodium, enofelast, isamoxole, ketotifen fumarate, levcromakalim, lodoxamide ethyl, lodoxamide tromethamine, montelukast sodium, ontazolast, oxarbazole, oxatomide, piriprost, piriprost potassium, pirolate, pobilukast edamine, quazolast, repirinast, ritolukast, sulukast, tetrazolast meglumine, tiaramide hydrochloride, tibenelast sodium, tomelukast, tranilast, verlukast, verofylline, zarirlukast.

Anti-atherosclerotic: mifobate, timefuronc.

Anticholelithic: monoctanoin.

Anticholelithogenic: chenodiol, ursodiol.

Anticholinergic: alverinc citrate, anisotropine methylbromide, atropine, atropine oxide hydrochloride, atropine sulfate, belladonna, benapryzine hydrochloride, benzetimide hydrochloride, benzilonium bromide, biperiden, biperiden hydrochloride, biperiden lactate, clidinium bromide, cyclopentolate hydrochloride, dexetimide, dicyclomine hydrochloride, dihexyverine hydrochloride, domazoline fumarate, elantrine, elucaine, ethybenztropine, eucatropine hydrochloride, glycopyrrolate, heteronium bromide, homatropine hydrobromide, homatropine methylbromide, hyoscyamine, hyoscyamine hydrobromide, hyoscyamine sulfate, isopropamide iodide, mepenzolate bromide, methylatropine nitrate, metoquizine, oxybutynin chloride, parapenzolate bromide, pentapiperium methylsulfate, phencarbamide, poldine methylsulfate, proglumide, propantheline bromide, propenzolate hydrochloride, scopolamine hydrobromide, tematropium methylsulfate, tiquinamide hydrochloride, tofenacin hydrochloride, toquizine, triampyzine sulfate, trihexyphenidyl hydrochloride, tropicamide.

Anticoagulant: ancrod, anticoagulant citrate dextrose solution, anticoagulant citrate phosphate dextrose adenine solution, anticoagulant citrate phosphate dextrose solution, anticoagulant heparin solution, anticoagulant sodium citrate solution, ardeparin sodium, bivalirudin, bromindione, dalteparin sodium, desirudin, dicumnarol, heparin calcium, heparin sodium, lyapolate sodium, nafamostat mesylate, phenprocoumon, tinzaparin sodium, warfarin sodium.

Anticoccidal: maduramicin.

Anticonvulsant: albutoin, ameltolide, atolide, buramate, carbamazepine, cinromide, citenamide, clonazepam, cyheptamide, dezinamide, dimethadione, divalproex sodium, eterobarb, ethosuximide, ethotoin, flurazepam hydrochloride, fluzinamide, fosphenyloin sodium, gabapentin, ilepcimide, lamotrigine, magnesium sulfate, mephenyloin, mephobarbital, methetoin, methsuximide, milacemide hydrochloride, nabazenil, nafimidone hydrochloride, nitrazepam, phenacemide, phenobarbital, phenobarbital sodium, phensuximide, phenyloin, phenyloin sodium, primidone, progabide, ralitoline, remacemide hydrochloride, ropizine, sabeluzole, stiripentol, sulthiame, thiopental sodium, tiletamine hydrochloride, topiramate, trimethadione, valproate sodium, valproic acid, vigabatrin, zoniclezole hydrochloride, zonisamide.

Antidepressant: adatanserin hydrochloride, adinazolam, adinazolam mesylate, alaproclate, aletamine hydrochloride, amedalin hydrochloride, amitriptyline hydrochloride, amoxapine, aptazapine maleate, azaloxan fumarate, azepindole, azipramine hydrochloride, bipenamol hydrochloride, bupropion hydrochloride, butacetin, butriptyline hydrochloride, caroxazone, cartazolate, ciclazindol, cidoxepin hydrochloride, cilobamine mesylate, clodazon hydrochloride, clomipramine hydrochloride, cotinine fumarate, cyclindole, cypenamine hydrochloride, cyprolidol hydrochloride, cyproximide, daledalin tosylate, dapoxetine hydrochloride, dazadrol maleate, dazepinil hydrochloride, desipramine hydrochloride, dexamisole, deximafen, dibenzepin hydrochloride, dioxadrol hydrochloride, dothiepin hydrochloride, doxepin hydrochloride, duloxetine hydrochloride, eclanamine maleate, encyprate, etoperidone hydrochloride, fantridone hydrochloride, fehmetozole hydrochloride, fenmetramide, fezolamine fumarate, fluotracen hydrochloride, fluoxetine, fluoxetine hydrochloride, fluparoxan hydrochloride, gamfexine, guanoxyfen sulfate, imafen hydrochloride, imiloxan hydrochloride, imipramine hydrochloride, indeloxazine hydrochloride, intriptyline hydrochloride, iprindole, isocarboxazid, ketipramine fumarate, lofepramine hydrochloride, lortalamine, maprotiline, maprotiline hydrochloride, melitracen hydrochloride, milacemide hydrochloride, minaprine hydrochloride, mirtazapine, moclobemide, modaline sulfate, napactadine hydrochloride, napamezole hydrochloride, nefazodone hydrochloride, nisoxetine, nitrafudam hydrochloride, nomifensine maleate, nortriptyline hydrochloride, octriptyline phosphate, opipramol hydrochloride, oxaprotiline hydrochloride, oxypertine, paroxetine, phenelzine sulfate, pirandamine hydrochloride, pizotyline, pridefine hydrochloride, prolintane hydrochloride, protriptyline hydrochloride, quipazine maleate, rolicyprine, seproxetine hydrochloride, sertraline hydrochloride, sibutramine hydrochloride, sulpiride, suritozole, tametraline hydrochloride, tampramine fumarate, tandamine hydrochloride, thiazesim hydrochloride, thozalinone, tomoxetine hydrochloride, trazodone hydrochloride, trebenzomine hydrochloride, trimipramine, trimipramine maleate, venlafaxine hydrochloride, viloxazine hydrochloride, zimeldine hydrochloride, zometapine.

Antidiabetic: acetohexamide, buformin, butoxamine hydrochloride, camiglibose, chlorpropamide, ciglitazone, englitazone sodium, etoformin hydrochloride, gliamilide, glibornuride, glicetanile sodium, gliflumide, glipizide, glucagon, glyburide, glyhexamide, glymidine sodium, glyoctamide, glyparamide, insulin, insulin, dalanated, insulin human, insulin human, isophane, insulin human zinc, insulin human zinc, extended, insulin, isophane, insulin lispro, insulin, neutral, insulin zinc, insulin zinc, extended, insulin zinc, prompt, linogliride, linogliride fumarate, metformin, methyl palmoxirate, palmoxirate sodium, pioglitazone hydrochloride, pirogliride tartrate, proinsulin human, seglitide acetate, tolazamide, tolbutamide, tolpyrramide, troglitazone, zopolrestat, and sitagliptin.

Antidiarrheal: rolgamidine, diphenoxylate hydrochloride (lomotil), metronidazole (flagyl), methylprednisolone (medrol), sulfasalazine (azulfidine).

Antidiuretic: argipressin tannate, desmopressin acetate, lypressin.

Antidote: dimercaprol, edrophonium chloride, fomepizole, leucovorin calcium, levoleucovorin calcium, methylene blue, protamine sulfate.

Antidyskinetic: selegiline hydrochloride.

Anti-emetic: alosetron hydrochloride, batanopride hydrochloride, bemesetron, benzquinamide, chlorpromazine, chlorpromazine hydrochloride, clebopride, cyclizine hydrochloride, dimenhydrinate, diphenidol, diphenidol hydrochloride, diphenidol pamoate, dolasetron mesylate, domperidone, dronabinol, fludorex, flumeridone, galdansetron hydrochloride, granisetron, granisetron hydrochloride, lurosetron mesylate, meclizine hydrochloride, metoclopramide hydrochloride, metopimazine, ondansetron hydrochloride, pancopride, prochlorperazine, prochlorperazine edisylate, prochlorperazine maleate, promethazine hydrochloride, thiethylperazine, thiethylperazine malate, thiethylperazine maleate, trimethobenzamide hydrochloride, zacopride hydrochloride.

Anti-epileptic: felbamate, loreclezole, tolgabide.

Anti-estrogen: clometherone, delmadinone acetate, nafoxidine hydrochloride, nitromifene citrate, raloxifene hydrochloride, tamoxifen citrate, toremifene citrate, trioxifene mesylate.

Antifibrinolytic: nafamostat mesylate.

Antifungal: acrisorcin, ambruticin, amphotericin b, azaconazole, azaserine, basifungin, bifonazole, biphenamine hydrochloride, bispyrithione magsulfex, butoconazole nitrate, calcium undecylenate, candicidin, carbol-fuchsin, chlordantoin, ciclopirox, ciclopirox olamine, cilofungin, cisconazole, clotrimazole, cuprimyxin, denofungin, dipyrithione, doconazole, econazole, econazole nitrate, enilconazole, ethonam nitrate, fenticonazole nitrate, filipin, fluconazole, flucytosine, fungimycin, griseofulvin, hamycin, isoconazole, itraconazole, kalafungin, ketoconazole, lomofimgin, lydimycin, mepartricin, miconazole, miconazole nitrate, monensin, monensin sodium, naftifine hydrochloride, neomycin undecylenate, nifuratel, nifurmerone, nitralamine hydrochloride, nystatin, octanoic acid, orconazole nitrate, oxiconazole nitrate, oxifungin hydrochloride, parconazole hydrochloride, partricin, potassium iodide, proclonol, pyrithione zinc, pyrroInitrin, rutamycin, sanguinarium chloride, saperconazole, scopafungin, selenium sulfide, sinefungin, sulconazole nitrate, terbinafine, terconazole, thiram, ticlatone, tioconazole, tolciclate, tolindate, tolnaftate, triacetin, triafungin, undecylenic acid, viridofulvin, zinc undecylenate, zinoconazole hydrochloride. One specific antifungal that is suitable is itraconazole.

Antiglaucoma agent: alprenoxime hydrochloride, colforsin, dapiprazole hydrochloride, dipivefrin hydrochloride, naboctate hydrochloride, pilocarpine, pimabine.

Antihemophilic: antihemophilic factor.

Antihemorrhagic: poliglusam.

Antihistaminic: acrivastine, antazoline phosphate, astemizole, azatadine maleate, barmastine, bromodiphenhydramine hydrochloride, brompheniramine maleate, carbinoxamine maleate, cetirizine hydrochloride, chlorpheniramine maleate, chlorpheniramine polistirex, cinnarizine, clemastine, clemastine fumarate, closiramine aceturate, cycliramine maleate, cyclizine, cyproheptadine hydrochloride, dexbrompheniramine maleate, dexchlorpheniramine maleate, dimethindene maleate, diphenhydramine citrate, diphenhydramine hydrochloride, dorastine hydrochloride, doxylamine succinate, ebastine, levocabastine hydrochloride, loratadine, mianserin hydrochloride, noberastine, orphenadrine citrate, pyrabrom, pyrilamine maleate, pyroxamine maleate, rocastine hydrochloride, rotoxamine, tazifylline hydrochloride, temelastine, terfenadine, tripelennamine citrate, tripelennamine hydrochloride, triprolidine hydrochloride, zolamine hydrochloride.

Antihyperlipidemic: cholestyramine resin, clofibrate, colestipol hydrochloride, crilvastatin, dalvastatin, dextrothyroxine sodium, fluvastatin sodium, gemfibrozil, lecimibide, lovastatin, niacin, pravastatin sodium, probucol, simvastatin, tiqueside, xenbucin.

Antihyperlipoproteinemic: acifran, beloxamide, bezafibrate, boxidine, butoxamine hydrochloride, cetaben sodium, ciprofibrate, gemcadiol, halofenate, lifibrate, meglutol, nafenopin, pimetine hydrochloride, theofibrate, tibric acid, treloxinate.

Antihypertensive: alfuzosin hydrochloride, alipamide, althiazide, amiquinsin hydrochloride, amlodipine besylate, amlodipine maleate, anaritide acetate, atiprosin maleate, belfosdil, bemitradine, bendacalol mesylate, bendroflumethiazide, benzthiazide, betaxolol hydrochloride, bethanidine sulfate, bevantolol hydrochloride, biclodil hydrochloride, bisoprolol, bisoprolol fumarate, bucindolol hydrochloride, bupicomide, buthiazide: candoxatril, candoxatrilat, captopril, carvedilol, ceronapril, chlorothiazide sodium, cicletanine, cilazapril, clonidine, clonidine hydrochloride, clopamide, cyclopenthiazide, cyclothiazide, darodipine, debrisoquin sulfate, delapril hydrochloride, diapamide, diazoxide, dilevalol hydrochloride, diltiazem malate, ditekiren, doxazosin mesylate, ecadotril, enalapril maleate, enalaprilat, enalkiren, endralazine mesylate, epithiazide, eprosartan, eprosartan mesylate, fenoldopam mesylate, flavodilol maleate, flordipine, flosequinan, fosinopril sodium, fosinoprilat, guanabenz, guanabenz acetate, guanacline sulfate, guanadrel sulfate, guancydine, guanethidine monosulfate, guanethidine sulfate, guanfacine hydrochloride, guanisoquin sulfate, guanoclor sulfate, guanoctine hydrochloride, guanoxabenz, guanoxan sulfate, guanoxyfen sulfate, hydralazine hydrochloride, hydralazine polistirex, hydroflumethiazide, indacrinone, indapamide, indolaprif hydrochloride, indoramin, indoramin hydrochloride, indorenate hydrochloride, lacidipine, leniquinsin, levcromakalim, lisinopril, lofexidine hydrochloride, losartan potassium, losulazine hydrochloride, mebutamate, mecamylamine hydrochloride, medroxalol, medroxalol hydrochloride, methalthiazide, methyclothiazide, methyldopa, methyldopate hydrochloride, metipranolol, metolazone, metoprolol fumarate, metoprolol succinate, metyrosine, minoxidil, monatepil maleate, muzolimine, nebivolol, nitrendipine, oformine, pargyline hydrochloride, pazoxide, pelanserin hydrochloride, perindopril erbumine, phenoxybenzamine hydrochloride, pinacidil, pivopril, polythiazide, prazosin hydrochloride, primidolol, prizidilol hydrochloride, quinapril hydrochloride, quinaprilat, quinazosin hydrochloride, quinelorane hydrochloride, quinpirole hydrochloride, quinuclium bromide, ramipril, rauwolfia serpentina, reserpine, saprisartan potassium, saralasin acetate, sodium nitroprusside, sulfinalol hydrochloride, tasosartan, teludipine hydrochloride, temocapril hydrochloride, terazosin hydrochloride, terlakiren, tiamenidine, tiamenidine hydrochloride, ticrynafen, tinabinol, tiodazosin, tipentosin hydrochloride, trichlormethiazide, trimazosin hydrochloride, trimethaphan camsylate, trimoxamine hydrochloride, tripamide, xipamide, zankiren hydrochloride, zofenoprilat arginine.

Antihypotensive: ciclafrine hydrochloride, midodrine hydrochloride.

Anti-infective: difloxacin hydrochloride, lauryl isoquinolinium bromide, moxalactam disodium, ornidazole, pentisomicin, sarafloxacin hydrochloride, protease inhibitors of hiv and other retroviruses, integrase inhibitors of hiv and other retroviruses, cefaclor (CECLOR™), acyclovir (ZOVIRAX™), norfloxacin (NOROXIN™), cefoxitin (MEFOXIN™), cefuroxime axetil (CEFTIN™), ciprofloxacin (CIPRO™).

Anti-infective, topical: alcohol, aminacrine hydrochloride, benzethonium chloride: bithionolate sodium, bromchlorenone, carbamide peroxide, cetalkonium chloride, cetylpyridinium chloride: chlorhexidine hydrochloride, clioquinol, domiphen bromide, fenticlor, fludazonium chloride, fuchsin, basic, furazolidone, gentian violet, halquinols, hexachlorophene: hydrogen peroxide, ichthammol, imidecyl iodine, iodine, isopropyl alcohol, mafenide acetate, meralein sodium, mercufenol chloride, mercury, ammoniated, methylbenzethonium chloride, nitrofurazone, nitromersol, octenidine hydrochloride, oxychlorosene, oxychlorosene sodium, parachlorophenol, camphorated, potassium permanganate, povidone-iodine, sepazonium chloride, silver nitrate, sulfadiazine, silver, symclosene, thimerfonate sodium, thimerosal: troclosene potassium.

Anti-inflammatory: acetaminophen, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium.

Antikeratinizing agent: doretinel, linarotene, pelretin.

Antimalarial: acedapsone, amodiaquine hydrochloride, amquinate, arteflene, chloroquine, chloroquine hydrochloride, chloroquine phosphate, cycloguanil pamoate, enpiroline phosphate, halofantrine hydrochloride, hydroxychloroquine sulfate, mefloquine hydrochloride, menoctone, mirincamycin hydrochloride, primaquine phosphate, pyrimethamine, quinine sulfate, tebuquine.

Antimicrobial: aztreonam, chlorhexidine gluconate, imidurea, lycetamine, nibroxane, pirazmonam sodium, propionic acid, pyrithione sodium, sanguinarium chloride, tigemonam dicholine.

Antimigraine: dolasetron mesylate, naratriptan hydrochloride, sergolexole maleate, sumatriptan succinate, zatosetron maleate.

Antimitotic: podofilox.

Antimycotic: amorolfine.

Antinauseant: buclizine hydrochloride, cyclizine lactate, naboctate hydrochloride.

Antineoplastic: acivicin, aclarubicin, acodazole hydrochloride, acrqnine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, ethiodized oil I 131, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, gold au 198, hydroxyurea, idarubicin hydrochloride, ifosfamide, ilmofosine, interferon alfa-2a, interferon alfa-2b, interferon alfa-N1, interferon alfa-N3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safmgol, safingol hydrochloride, semustine, simtrazene, sparfosate sodium, sparsomycin, spirogermanium hydrochloride, spiromustine, spiroplatin, streptonigrin, streptozocin, strontium chloride sr 89, sulofenur, talisomycin, taxane, taxoid, tecogalan sodium, tegafur, teloxantrone hydrochloride, temoporfin, teniposide, teroxirone, testolactone, thiamiprine, thioguanine, thiotepa, tiazofurin, tirapazamine, topotecan hydrochloride, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Other anti-neoplastic compounds include: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, atrsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dioxamycin, diphenyl spiromustine, docosanol, dolasetron, doxifluridine, droloxifene, dronabinol, duocannycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, 4-irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A +myobacterium cell wall sk, mopidamol, multiple drug resistance genie inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone +pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofuran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfmosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, zinostatin stimalamer.

Anti-cancer supplementary potentiating agents: tricyclic anti-depressant drugs (e.g., imipramine, desipramine, amitryptyline, clomiprainine, trimipramine, doxepin, nortriptyline, protriptyline, amoxapine and maprotiline), non-tricyclic anti-depressant drugs (e.g., sertraline, trazodone and citalopram), $Ca^{++}$ antagonists (e.g., verapamil, nifedipine, nitrendipine and caroverine), calmodulin inhibitors (e.g., prenylamine, trifluoroperazine and clomipramine), amphotericin B, triparanol analogues (e.g., tamoxifen), antiarrhythmic drugs (e.g., quinidine), antihypertensive drugs (e.g., reserpine), thiol depleters (e.g., buthionine and sulfoximine) and Multiple Drug Resistance reducing agents such as Cremaphor EL.

Antineutropenic: filgrastim, lenograstim, molgramostim, regramostim, sargramostim.

Antiobsessional agent: fluvoxamine maleate.

Antiparasitic: abamectin, clorsulon, ivermectin.

Antiparkinsonian: benztropine mesylate, biperiden, biperiden hydrochloride, biperiden lactate, carmantadine, ciladopa hydrochloride, dopamantine, ethopropazine hydrochloride, lazabemide, levodopa, lometraline hydrochloride, mofegiline hydrochloride, naxagolide hydrochloride, pareptide sulfate, procyclidine hydrochloride, quinetorane hydrochloride, ropinirole hydrochloride, selegiline hydrochloride, tolcapone, trihexyphenidyl hydrochloride. antiperistaltic: difenoximide hydrochloride, difenoxin, diphenoxylate hydrochloride, fluperamide, lidamidine hydrochloride, loperamide hydrochloride, malethamer, nufenoxole, paregoric.

Antipneumocystic: atovaquone.

Antiproliferative agent: piritrexim isethionate.

Antiprostatic hypertrophy: sitogluside.

Antiprotozoal: amodiaquine, azanidazole, bamidazole, carnidazole, chlortetracycline bisulfate, chlortetracycline hydrochloride, flubendazole, flunidazole, halofuginone hydrobromide, imidocarb hydrochloride, ipronidazole, metronidazole, misonidazole, moxnidazole, nitarsone, partricin, puromycin, puromycin hydrochloride, ronidazole, sulnidazole, tinidazole.

Antipruritic: cyproheptadine hydrochloride, methdilazine, methdilazine hydrochloride, trimeprazine tartrate.

Antipsoriatic: acitretin, anthralin, azaribine, calcipotriene, cycloheximide, enazadrem phosphate, etretinate, liarozole fumarate, lonapalene, tepoxalin.

Antipsychotic: acetophenazine maleate, alentemol hydrobromide, alpertine, azaperone, batelapine maleate, benperidol, benzindopyrine hydrochloride, brofbxine, bromperidol, bromperidol decanoate, butaclamol hydrochloride, butaperazine, butaperazine maleate, carphenazine maleate, carvotroline hydrochloride, chlorpromazine, chlorpromazine hydrochloride, chlorprothixene, cinperene, cintriamide, clomacran phosphate, clopenthixol, clopimozide, clopipazan mesylate, cloroperone hydrochloride, clothiapine, clothixamide maleate, clozapine, cyclophenazine hydrochloride, droperidol, etazolate hydrochloride, fenimide, flucindole, flumezapine, fluphenazine decanoate, fluphenazine enanthate, fluphenazine hydrochloride, fluspiperone, fluspirilene, flutroline, gevotroline hydrochloride, halopemide, haloperidol, haloperidol decanoate, iloperidone, imidoline hydrochloride, lenperone, mazapertine succinate, mesoridazine, mesoridazine besylate, metiapine, milenperone, milipertine, molindone hydrochloride, naranol hydrochloride, neflumozide hydrochloride, ocaperidone, olanzapine, oxiperomide, penfluridol, pentiapine maleate, perphenazine, pimozide, pinoxepin hydrochloride, pipamperone, piperacetazine, pipotiazine palniitate, piquindone hydrochloride, prochlorperazine edisylate, prochlorperazine maleate, promazine hydrochloride, remoxipride, remoxipride hydrochloride, rimcazole hydrochloride, seperidol hydrochloride, sertindole, setoperone, spiperone, thioridazine, thioridazine hydrochloride, thiothixene, thiothixene hydrochloride, tioperidone hydrochloride, tiospirone hydrochloride, trifluoperazine hydrochloride, trifluperidol, triflupromazine, triflupromazine hydrochloride, ziprasidone hydrochloride.

Antirheumatic: auranofin, aurothioglucose, bindarit, lobenzarit sodium, phenylbutazone, pirazolac, prinomide tromethamine, seprilose.

Antischistosomal: becanthone hydrochloride, hycanthone, lucanthone hydrochloride, niridazole, oxamniquine, pararosaniline pamoate, teroxalene hydrochloride.

Antiseborrheic: chloroxine, piroctone, piroctone olamine, resorcinol monoacetate. antisecretory: arbaprostil, deprostil, fenoctimine sulfate, octreotide, octreotide acetate, omeprazole sodium, rioprostil, trimoprostil.

Antispasmodic: stilonium iodide, tizanidine hydrochloride.

Antithrombotic: anagrelide hydrochloride, bivalirudin, dalteparin sodium, danaparoid sodium, dazoxiben hydrochloride, efegatran sulfate, enoxaparin sodium, ifetroban, ifetroban sodium, tinzaparin sodium, trifenagrel.

Antitussive: benzonatate, butamirate citrate, chlophedianol hydrochloride, codeine polistirex, codoxime, dextromethorphan, dextromethorphan hydrobromide, dextromethorphan polistirex, ethyl dibunate, guaiapate, hydrocodone bitartrate, hydrocodone polistirex, levopropoxyphene napsylate, noscapine, pemerid nitrate, pipazethate, suxemerid sulfate.

Anti-ulcerative: aceglutamide aluminum, cadexomer iodine, cetraxate hydrochloride, enisoprost, isotiquimide, lansoprazole, lavoltidine succinate, misoprostol, nizatidine, nolinium bromide, pantoprazole, pifamine, pirenzepine hydrochloride, rabeprazole sodium, remiprostol, roxatidine acetate hydrochloride, sucralfate, sucrosofate potassium, tolimidone.

Anti-urolithic: cysteamine, cysteamine hydrochloride, tricitrates.

Appetite suppressant: dexfenfluramine hydrochloride, phendimetrazine tartrate, phentermine hydrochloride.

Benign prostatic hyperplasia therapy agent: tamsulosin hydrochloride.

Blood glucose regulators: human insulin, glucagon, tolazamide, tolbutamide, chloropropamide, acetohexamide and glipizide.

Bone resorption inhibitor: alendronate sodium, etidronate disodium, pamidronate disodium.

Bronchodilator: albuterol, albuterol sulfate, azanator maleate, bamifylline hydrochloride, bitolterol mesylate, butaprost, carbuterol hydrochloride, clorprenaline hydrochloride, colterol mesylate, doxaprost, doxofylline, dyphylline, enprofylline, ephedrine, ephedrine hydrochloride, fenoterol, fenprinast hydrochloride, guaithylline, hexoprenaline sulfate, hoquizil hydrochloride, ipratropium bromide, isoetharine, isoetharine hydrochloride, isoetharine mesylate, isoproterenol hydrochloride, isoproterenol sulfate, metaproterenol polistirex, metaproterenol sulfate, nisbuterol mesylate, oxtriphylline, picumeterol fumarate, piquizil hydrochloride, pirbuterol acetate, pirbuterol hydrochloride, procaterol hydrochloride, pseudoephedrine sulfate, quazodine, quinterenol sulfate, racepinephrine, racepinephrine hydrochloride, reproterol hydrochloride, rimiterol hydrobromide, salmeterol, salmeterol xinafoate, soterenol hydrochloride, sulfonterol hydrochloride, suloxifen oxalate, terbutaline sulfate, theophylline, xanoxate sodium, zindotrine, zinterol hydrochloride.

Carbonic anhydrase inhibitor: acetazolamide, acetazolamide sodium, dichlorphenamide, dorzolamide hydrochloride, methazolamide, sezolamide hydrochloride.

Cardiac depressant: acecamide hydrochloride, acetylcholine chloride, actisomide, adenosine, amiodarone, aprindine, aprindine hydrochloride, artilide fumarate, azimilide Dihydrochloride, bidisomide, bucamide maleate, bucromarone, butoprozine hydrochloride, capobenate sodium, capobenic acid, cifenline, cifenline succinate, clofilium phosphate, disobutamide, disopyramide, disopyramide phosphate, dofetilide, drobuline, edifolone acetate, emilium tosylate, encamide hydrochloride, flecamide acetate, ibutilide fumarate, indecamide hydrochloride, ipazilide fumarate, lorajmine hydrochloride, lorcamide hydrochloride, meobentine sulfate, mexiletine hydrochloride, modecamide, moricizine, oxiramide, pirmenol hydrochloride, pirolazamide, pranolium chloride, procainamide hydrochloride, propafenone hydrochloride, pyrinoline, quindonium bromide, quinidine gluconate, quinidine sulfate, recainam hydrochloride, recainam tosylate, risotilide hydrochloride, ropitoin hydrochloride, sematilide hydrochloride, suricamide maleate, tocamide, tocamide hydrochloride, transcamide.

Cardioprotectant: dexrazoxane, draflazine.

Cardiotonic: actodigin, aminone, bemoradan, butopamine, carbazeran, carsatrin succinate, deslanoside, digitalis, digitoxin, digoxin, dobutamine, dobutamine hydrochloride, dobutamine lactobionate, dobutamine tartrate, enoximone, imazodan hydrochloride, indolidan, isomazole hydrochloride, levdobutamine lactobionate, lixazinone sulfate, medorinone, milrinone, pelrinone hydrochloride, pimobendan, pirioximone, prinoxodan, proscillaridin, quazinone, tazolol hydrochloride, vesnarinone.

Cardiovascular agent: dopexamine, dopexamine hydrochloride.

Choleretic: dehydrocholic acid, fencibutirol, hymecromone, piprozolin, sincalide, tocamphyl.

Cholinergic: aceclidine, bethanechol chloride, carbachol, demecarium bromide, dexpanthenol, echothiophate iodide, isoflurophate, methacholine chloride, neostigmine bromide, neostigmine methylsulfate, physostigmine, physostigmine salicylate, physostigmine sulfate, pilocarpine, pilocarpine hydrochloride, pilocarpine nitrate, pyridostigmine bromide.

Cholinergic agonist: xanomeline, xanomeline tartrate.

Cholinesterase deactivator: obidoxime chloride, pralidoxime chloride, pralidoxime iodide, pralidoxime mesylate.

Coccidiostat: arprinocid, narasin, semduramicin, semduramicin sodium.

Dognition adjuvant: ergoloid mesylates, piracetam, pramiracetam hydrochloride, pramiracetam sulfate, tacrine hydrochloride.

Cognition enhancer: besipirdine hydrochloride, linopirdine, sibopirdine.

Depressant: omeprazole.

Diagnostic aid: aminohippurate sodium, anazolene sodium, arclofenin, arginine, bentiromide, benzylpenicilloyl polylysine, butedronate tetrasodium, butilfenin, coccidioidin, corticorelin ovine triflutate, corticotropin, repository, corticotropin zinc hydroxide, diatrizoate meglumine, diatrizoate sodium, diatrizoic acid, diphtheria toxin for schick test, disofenin, edrophonium chloride, ethiodized oil, etifenin, exametazime, ferristenc, ferumoxides, ferumoxsil, fluorescein, fluorescein sodium, gadobenate dimeglumine, gadoteridol, gadodiamide, gadopentetate dimegiumine, gadoversetamide, histoplasmin, impromidine hydrochloride, indigotindisulfonate sodium, indocyanine green, lobenguane sulfate $I^{123}$, iobenzamic acid, iocarmate meglumine, locarmic acid, iocetamic acid, iodamide, lodamide megiumine, iodipamide meglumine, iodixanol, iodoxamate meglumine, iodoxamic acid, ioglicic acid, ioglucol, ioglucomide, ioglycamic acid, iogulamide, lohexyl, iomeprol, iopamidol, iopanoic acid, iopentol, iophendylate, iprofenin, iopronic acid, ioprocemic acid, iopydol, iopydone, iosefamic acid, ioseric acid, iosulamide meglumine, iosumetic acid, iotasul, iotetric acid, iothalamate meglumine, iothalamate sodium, iothalamic acid, iotrolan, iotroxic acid, ioversol, ioxaglate meglumine, ioxagiate sodium, ioxaglic acid, ioxilan, ioxotrizoic acid, ipodate calcium, ipodate sodium, isosulfan blue, leukocyte typing serum, lidofenin, mebrofenin, meglumine, metrizamide, metrizoate sodium, metyrapone, metyrapone tartrate, mumps skin test antigen, pentetic acid, propyliodone, quinaldine blue, sermorelin acetate, sodium iodide $I^{123}$, sprodiamide, stannous pyrophosphate, stannous sulfur colloid, succimer, teriparatide acetate, tetrofosmin, tolbutamide sodium, tuberculin, tyropanoate sodium, xylose.

Diuretic: ambuphylline, ambuside, amiloride hydrochloride, azolimine, azosemide, brocrinat, bumetanide, chlorothiazide, chlorthalidone, clazolimine, clorexolone, ethacrynate sodium, ethacrynic acid, etozolin, fenquizone, furosemide, hydrochlorothiazide, isosorbide, mannitol, mefruside, ozolinone, piretanide, spiroxasone, torsemide, triamterene, triflocin, urea.

Dopaminergic agent: ibopamine.

Ectoparasiticide: nifluridide, permethrin.

Emetic: apomorphine hydrochloride.

Enzyme inhibitor: acetohydroxamic acid, alrestatin sodium, aprotinin, benazepril hydrochloride, benazeprilat, benurestat, bromocriptine, bromocriptine mesylate, cilastatin sodium, fluorofamide, lergotrile, lergotrile mesylate, levcycloserine, libenzapril, pentopril, pepstatin, perindopril, polignate sodium, sodium amylosulfate, sorbinil, spirapril hydrochloride, spiraprilat, taleranol, teprotide, tolfamide, zofenopril calcium.

Estrogen: chlorotrianisene, dienestrol, diethylstilbestrol, diethylstilbestrol diphosphate, equilin, estradiol, estradiol cypionate, estradiol enanthate, estradiol undecylate, estradiol valerate, estrazinol hydrobromide, estriol, estrofurate, estrogens, conjugated, estrogens, esterified, estrone, estropipate, ethinyl estradiol, fenestrel, mestranol, nylestriol, quinestrol.

Fibrinolytic: anistreplase, bisobrin lactate, brinolase.

Free oxygen radical scavenger: pegorgotein.

Gastrointestinal motility agents: cisapride (PROPULSID™), metoclopramide (REGLAN™), hyoscyamine (LEVSIN™).

Glucocorticoid: amcinonide, beclomethasone dipropionate, betamethasone, betamethasone acetate, betamethasone benzoate, betamethasone dipropionate, betamethasone sodium phosphate, betamethasone valerate, carbenoxolone sodium, clocortolone acetate, clocortolone pivalate, coprednol, corticotropin, corticotropin, repository, corticotropin zinc hydroxide, cortisone acetate, cortivazol, descinolone acetonide, dexamethasone, dexamethasone sodium phosphate, diflucortolone, diflucortolone pivalate, flucloronide, flumethasone, flumethasone pivalate, flunisolide, fluocinolone acetonide, fluocinonide, fluocortolone, fluocortolone caproate, fluorometholone, fluperolone acetate, fluprednisolone, fluprednisolone valerate, flurandrenolide, formocortal, hydrocortisone, hydrocortisone acetate, hydrocortisone buteprate, hydrocortisone butyrate, hydrocortisone sodium phosphate, hydrocortisone sodium succinate, hydrocortisone valerate, medrysone, methylprednisolone, methylprednisolone acetate, methylprednisoloime sodium phosphate, methylprednisolone sodium succinate, nivazol, paramethasone acetate, prednicarbate, prednisolone, prednisolone acetate, prednisolone hemisuccinate, prednisolone sodium phosphate, prednisolone sodium succinate, prednisolone tebutate, prednisone, prednival, ticabesone propionate, tralonide, triamcinolone, triamcinolone acetonide, triamcinolone acetonide sodium, triamcinolone diacetate, triamcinolone hexacetonide.

Gonad-stimulating principle: buserelin acetate, clomiphene citrate, ganirelix acetate, gonadorelin acetate, gonadorelin hydrochloride, gonadotropin, chorionic, menotropins.

Hair growth stimulant: minoxidil.

Hemostatic: aminocaproic acid, oxamarin hydrochloride, sulmarin, thrombin, tranexarnic acid.

Histamine H2 receptor antagonists: ranitidine (ZANTAC™), famotidine (PEPCID™), cimetidine (TAGAMET™), nizatidine (AXID™).

Hormone: diethylstilbestrol, progesterone, 17 hydroxy progesterone, medroxyprogesterone, norgestrel, norethynodrel, estradiol, megestrol (megace), norethindrone, levonorgestrel, ethyndiol, ethinyl estradiol, mestranol, estrone, equilin, 17 alpha dihydroequilin, equilenin, 17 alpha dihydroequilenin, 17 alpha estradiol, 17 beta estradiol, leuprolide (LUPRON™), glucagon, testolactone, clomiphene, human menopausal gonadotropins, human chorionic gonadotropin, urofollitropin, bromocriptine, gonadorelin, luteinizing hormone releasing hormone and analogs, gonadotropins, danazol, testosterone, dehydroepiandrosterone, androstenedione, dihydroestosterone, relaxin, oxytocin, vasopressin, folliculostatin, follicle regulatory protein, gonadoctrinins, oocyte maturation inhibitor, insulin growth factor, follicle stimulating hormone, luteinizing hormone, tamoxifen., corticorelin ovine triftutate, cosyntropin, metogest, pituitary, posterior, seractide acetate, somalapor, somatrem, somatropin, somenopor, somidobove.

Hypocholesterolemic: lifibrol.

Hypoglycemic: darglitazone sodium: glimepiride.

Hypolipidemic: azalanstat dihydrochloride, colestolone, surfomer, xenalipin.

Hypotensive: viprostol.

Hmgcoa reductase inhibitors: lovastatin (MEVACOR™), simvastatin (ZOCOR™), pravastatin (PRAVACHOL™), fluvasatin (LESCOL™).

Immunizing agent: antirabies serum, antivenin (*latrodectus mactans*), antivenin (*micrurus fulvius*), antivenin (*crotalidae*) polyvalent, BCG vaccine, botulism antitoxin, cholera vaccine, diphtheria antitoxin, diphtheria toxoid, diphtheria toxoid adsorbed, globulin, immune, hepatitis b immune globulin, hepatitis B virus vaccine inactivated, influenza virus vaccine, measles virus vaccine live, meningococcal polysaccharide vaccine group A, meningococcal polysaccharide vaccine group C, mumps virus vaccine live, pertussis immune globulin, pertussis vaccine, pertussis vaccine adsorbed, plague vaccine, poliovirus vaccine inactivated, poliovirus vaccine live oral, rabies immune globulin, rabies vaccine, $Rh_o$ (D) immune globulin, rubella virus vaccine live, smallpox vaccine, tetanus antitoxin, tetanus immune globulin, tetanus toxoid, tetanus toxoid adsorbed, typhoid vaccine, yellow fever vaccine, vaccinia immune globulin, varicella-zoster immune globulin.

Immunomodulator: dimepranol acedoben, imiquimod, interferon beta-Ib, lisofylline, mycophenolate mofetil, prczatide copper acetate.

Immunoregulator: azarole, fanetizole mesylate, frentizole, oxamisole hydrochloride, ristianol phosphate, thymopentin, tilomisole.

Immunostimulant: loxoribine, teceleukin.

Immunosuppressant: azathioprine, azathioprine sodium, cyclosporine, daltroban, gusperimus trihydrochloride, sirolimus, tacrolimus.

Impotence therapy adjunct: delequamine hydrochloride.

Inhibitor: acarbose, atorvastatin calcium, benserazide, brocresine, carbidopa, clavulanate potassium, dazmegrel, docebenone, epoprostenol, epoprostenol sodium, epristeride, finasteride, flurbiprofen sodium, furegrelate sodium, lufironil, miglitol, orlistat, pimagedine hydrochloride, pirmagrel, ponalrestat, ridogrel, sulbactam benzathine, sulbactampivoxil, sulbactam sodium, suronacrine maleate, tazobactam, tazobactam sodium, ticlopidine hydrochloride, tirilazad mesylate, tolrestat, velnacrine maleate, zifrosilone, zileuton.

Keratolytic: alcloxa, aldioxa, benzoyl peroxide, dibenzothiophene, etarotene, isotretinoin, motretinide, picotrin diolamine, resorcinol, resorcinol monoacetate, salicylic acid, sumarotene, tazarotene, tetroquinone, tretinoin.

LHRL agonist: deslorelin, goserelin, histrelin, lutrelin acetate, nafarelin acetate.

Liver disorder treatment: malotilate.

Luteolysin: fenprostalene.

Memory adjuvant: dimoxamine hydrochloride, ribaminol.

Mental performance enhancer: aniracetam.

Mood regulator: fengabine.

Mucolytic: acetylcysteine, carbocysteine, domiodol.

Mucosal protective agents: misoprostol (CYTOTEC™).

Mydriatic: berefrine.

Nasal decongestant: nemazoline hydrochloride, pseudoephedrine polistirex.

Neuroleptic: duoperone fumarate, risperidone.

Neuromuscular blocking agent: atracurium besylate, cisatracurium besylate, doxacurium chloride, gallamine triethiodide, metocurine iodide, mivacurium chloride, pancuronium bromide, pipecuronium bromide, rocuronium bromide, succinylcholine chloride, tubocurarine chloride, vecuronium bromide.

Neuroprotective: dizocilpine maleate.

NMDA antagonist: selfotel.

Non-hormonal sterol derivative: pregnenolone succinate.

Oxytocic: carboprost, carboprost methyl, carboprost tromethamine, dinoprost, dinoprost tromethamine, dinoprostone, ergonovine maleate, meteneprost, methylergonovine maleate, oxytocin, sparteine sulfate.

Plasminogen activator: alteplase, urokinase.

Platelet activating factor antagonist: lexipafant.

Platelet aggregation inhibitor: acadesine, beraprost, beraprost sodium, ciprostene calcium, itazigrel, lifarizine, oxagrelate.

Post-stroke and post-head trauma treatment: citicoline sodium.

Potentiator: pentostatin, talopram hydrochloride.

Progestin: algestone acetophenide, amadinone acetate, anagestone acetate, chlormadinone acetate, cingestol, clogestone acetate, clomegestone acetate, desogestrel, dimethisterone, dydrogesterone, ethynerone, ethynodiol diacetate, etonogestrel, fluorogestone acetate, gestaclone, gestodene, gestonorone caproate, gestrinone, haloprogesterone, hydroxyprogesterone caproate, levonorgestrel, lynestrenol, medrogestone, medroxyprogesterone acetate, methynodiol diacetate, norethindrone, norethindrone acetate, norethynodrel, norgestimate, norgestomet, norgestrel, oxogestone phenpropionate, progesterone, quingestanol acetate, quingestrone, tigestol.

Prostaglandin: cloprostenol sodium, fluprostenol sodium, gemeprost, prostalene, sulprostone.

Prostate growth inhibitor: pentomone.

Prothyrotropin: protirelin.

Psychotropic: minaprine.

Pulmonary surface: beractant, colfosceril palmitate.

Radioactive agent: fibrinogen $I^{125}$, fludeoxyglucose $F^{18}$, fluorodopa $F^{18}$, insulin $I^{125}$, insulin $I^{131}$, iobenguane $I^{123}$, iodipamide sodium $I^{131}$% iodoantipyrine $I^{131}$% iodocholesterol $I^{131}$% iodohippurate sodium $I^{123}$, iodohippurate sodium $I^{125}$, iodohippurate sodium $I^{131}$% iodopyracet $I^{125}$, iodopyracet $I^{131}$, iofetamine hydrochloride $I^{123}$, iomethin $I^{125}$, iomethin $I^{131}$% iothalamate sodium $I^{125}$, iothalamate sodium $I^{131}$, iotyrosine $I^{131}$, liothyronine $I^{125}$, liothyronine $I^{131}$% merisoprol acetate $Hg^{197}$, merisoprol acetate $Hg^{203}$, merisoprol $Hg^{197}$, selenomethionine $Se^{75}$, technetium $Tc^{99m}$ antimony trisulfide colloid, technetium $Tc^{99m}$ bicisate, technetium $Tc^{99m}$ disofenin, technetium $Tc^{99m}$ etidronate, technetium $Tc^{99m}$ exametazime, technetium $Tc^{99m}$ furifosmin, technetium $Tc^{99m}$ gluceptate, technetium $Tc^{99m}$ lidofenin, technetium $Tc^{99m}$ mebrofenin, technetium $Tc^{99m}$ medronate, technetium $Tc^{99m}$ medronate disodium, technetium $Tc^{99m}$ mertiatide, technetium $Tc^{99m}$ oxidronate, technetium $Tc^{99m}$ pentetate, technetium $Tc^{99m}$ pentetate calcium trisodium, technetium $Tc^{99m}$ sestamibi, technetium $Tc^{99m}$ siboroxime, technetium $Tc^{99m}$ succimer, technetium $Tc^{99m}$ sulfur colloid, technetium $Tc^{99m}$ teboroxime, technetium $Tc^{99m}$ tetrofosmin, technetium $Tc^{99m}$ tiatide, thyroxine $I^{125}$, thyroxine $I^{131}$, tolpovidone $I^{131}$, triolein $I^{125}$, triolein $I^{131}$.

Regulator: calcifediol, calcitonin, calcitriol, clodronic acid, dihydrotachysterol, etidronic acid, oxidronic acid, piridronate sodium, risedronate sodium, secalciferol.

Relaxant: adiphenine hydrochloride, alcuronium chloride, aminophylline, azumolene sodium, baclofen, benzoctamine hydrochloride, carisoprodol, chlorphenesin carbamate, chlorzoxazone, cinflumide, cinnamedrine, clodanolene, cyclobenzaprine hydrochloride, dantrolene, dantrolene sodium, fenalamide, fenyripol hydrochloride, fetoxylate hydrochloride, flavoxate hydrochloride, fletazepam, flumetramide,-flurazepam hydrochloride, hexafluorenium bromide, isomylamine hydrochloride, lorbamate, mebeverine hydrochloride, mesuprine hydrochloride, metaxalone, methocarbamol, methixene hydrochloride, nafomine malate, nelezaprine maleate, papaverine hydrochloride, pipoxolan.

Hydrochloride, quinctolate, ritodrine, ritodrine hydrochloride, rolodine, theophylline sodium glycinate, thiphenamil hydrochloride, xilobam.

Repartitioning agent: cimaterol.

Scabicide: amitraz, crotamiton.

Sclerosing agent: ethanolamine oleate, morrhuate sodium, tribenoside.

Sedative: propiomazine.

Sedative-hypnotic: allobarbital, alonimid, alprazolam, amobarbital sodium, bentazepam, brotizolam, butabarbital, butabarbital sodium, butalbital, capuride, carbocloral, chloral betaine, chloral hydrate, chlordiazepoxide hydrochloride, cloperidone hydrochloride, clorethate, cyprazepam, dexclamol hydrochloride, diazepam, dichloralphenazone, estazolam, ethchlorvynol, etomidate, fenobam, flunitrazepam, fosazepam, glutethimide, halazepam, lormetazepam, mecloqualone, meprobamate, methaqualone, midaflur, paraldehyde, pentobarbital, pentobarbital sodium, perlapine, prazepam, quazepam, reclazepam, roletamide, secobarbital, secobarbital sodium, suproclone, thalidomide, tracazolate, trepipam maleate, triazolam, tricetamide, triclofos sodium, trimetozine, uldazepam, zaleplon, zolazepam hydrochloride, zolpidem tartrate.

Selective adenosine al antagonist: apaxifylline.

Serotonin antagonist: altanserin tartrate, amesergide, ketanserin, ritanserin.

Serotonin inhibitor: cinanserin hydrochloride, fenclonine, fonazine mesylate, xylamidine tosylate.

Serotonin receptor antagonist: tropanserin hydrochloride.

Steroid: dexamethasone aceflrate, mometasone furoate.

Stimulant: amfonelic acid, amphetamine sulfate, ampyzine sulfate, arbutamine hydrochloride, azabon, caffeine, ceruletide, ceruletide diethylamine, cisapride, dazopride fumarate, dextroamphetamine, dextroamphetamine sulfate, difluanine hydrochloride, dimefline hydrochloride, doxapram hydrochloride, etryptamine acetate, ethamivan, fenethylline hydrochloride, flubanilate hydrochloride, fluorothyl, histamine phosphate, indriline hydrochloride, mefexamide, methamphetamine hydrochlo ride, methylphenidate hydrochloride, pemoline, pyrovalerone hydrochloride, xamoterol, xamoterol fumarate.

Suppressant: amfhutizole, coxchicine, tazofelone.

Symptomatic multiple sclerosis: fampridine.

Synergist: proadifen hydrochloride.

Thyroid hor move: levothyroxine sodium, liothyronine sodium, liotrix.

Thyroid inhibitor: methimazole, propylthiouracil.

Thyromimetic: thyromedan hydrochloride.

Tranquilizer: bromazepam, buspirone hydrochloride, chlordiazepoxide, clazolam, clobazam, clorazepate dipotassium, clorazepate monopotassium, demoxepam, dexmedetomidine, enciprazine hydrochloride, gepirone hydrochloride, hydroxyphenamate, hydroxyzine Hydrochloride, hydroxyzine pamoate, ketazolam, lorazepam, lorzafone, loxapine, loxapine succinate, medazepam hydrochloride, nabilone, nisobamate, oxazepam, pentabamate, pirenperone, ripazepam, rolipram, sulazepam, taciamine hydrochloride, temazepam, triflubazam, tybamate, valnoctamide.

Amyotrophic lateral sclerosis agents: riluzole.

Cerebral ischemia agents: dextrorphan hydrochloride.

Paget's disease agents: tiludronate disodium.

Unstable angina agents: tirofiban hydrochloride.

Uricosuric: benzbromarone, irtemazole, probenecid, sulfinpyrazone.

Vasoconstrictor: angiotensin amide, felypressin, methysergide, methysergide maleate.

Vasodilator: alprostadil, azaclorzine hydrochloride, bamethan sulfate, bepridil hydrochloride, buterizine, cetiedil citrate, chromonar hydrochloride, clonitrate, diltiazem hydrochloride, dipyridamole, droprenilamine, erythrityl tetranitrate, felodipine, flunarizine hydrochloride, fostedil, hexobendine, inositol niacinate, iproxamine hydrochloride, isosorbide dinitrate, isosorbide mononitrate, isoxsuprine hydrochloride, lidoflazine, mefenidil, mefenidil fumarate, mibefradil dihydrochloride, mioflazine hydrochloride, mixidine, nafronyl oxalate, nicardipine hydrochloride, nicergoline, nicorandil, nicotinyl alcohol, nifedipine, nimodipine, nisoldipine, oxfenicine, oxprenolol hydrochloride, pentaerythritol tetranitrate, pentoxifylline, pentrinitrol, perhexyline maleate, pindolol, pirsidomine, prenylamine, propatyl nitrate, suloctidil, terodiline hydrochloride, tipropidil hydrochloride, tolazoline hydrochloride, xanthinol niacinate.

Vulnerary: allantoin.

Wound healing agent: ersofermin.

Xanthine oxidase inhibitor: allopurinol, oxypurinol.

Other pharmaceutical agents include: 1-decpyrrolidinone, 1-dodecpyrrolidinone, 16α-fluoroestradiol, 16-epiestriol, 16α-gitoxin, 17α estradiol, 17β estradiol, 1alpha-hydroxyvitamin D2,2'-nor-cGMP, 20-epi-1,25 dihydroxyvitamin D3, 22-oxacalcitriol, 2CVV, 3-isobutyl GABA, 6-FUDCA, 7-methoxytacrine, abamectin, abanoquil, abecarnil, abiraterone, acadesine, acamprosate, acarbose, aceclofenac, acemannan, acetomepregenol, acetyl-L-carnitine, acetylcysteine, N-acetylmethadol, acifran, acipimox, acitemate, acitretin, aclarubicin, aclatonium, napadisilate, aconiazide, acrivastinet, adafenoxate, adapalene, adatanserin, adecypenol, adefovir dipivoxil, adelmidrol, ademetionine, adinazolam, adiposin, adozelesin, adrafinil, alacepril, aladapcin, alaptide, albendazole, albolabrin, aldecalmycin, aldesleukin, alendronic acid, alentemol, alfacalcidol, alfuizosin, alglucerase, alinastine, alosetron, alpha idosone, alprostadil, altretamine, altromycin B, ambamustine, amelometasone, amesergide, amezinium metilsulfate, amfebutamone, amidox, amifloxacin, amifostine, amiodarone, amisulpride, amlexanox, amlodipine, amlodipine, ampiroxicam, aminone, amrubicin, amsacrine, amylin, amythiamicin, anagrelide, anakinra, ananain, anaritide, anastrozole, andrographolide, anordrin, apadoline, apafant, apaxifylline, aphidicolin glycinate, apraclonidine, aprosulate sodium, aptiganel, apurinic acid, aranidipine, arbekacin, arbidol, arbutamine, ardeparin sodium, arecatannin B1, argatroban, aripiprazol, arotinolol, asimadoline, aspalatone, asperfuran, aspoxicillin, astemizole, asulacrine, atamestane, atenolol, S-atevirdine, atosiban, atovaquone, atpenin B, atrimustine, atrinositol, aureobasidin A, azadirachtine, azasetron, azatyrosine, azelaic acid, azelastine, azelnidipine, azimilide, azithromycin, azosemide, aztreonam, baccatin III, bacoside A, bacoside B, bactobolamine, balazipone, balhimycin, balofloxacin, balsalazide, bambuterol, baohuoside 1, bamidipine, basifungin, batebulast, batimastat, beauvericin, becaplermin, becliconazole, befloxatone, belfosdil, bellenamine, benflumetol, benidipine, benzisoxazole, benzochlorins, benzoidazoxan, benzoylstaurosporine, benztropine, bepridil, beractant, beraprost, berlafenone, bertosamil, besipirdine, beta-alethine, betaclamycin B, betamipron, betaxolol, betulinic acid, bevantolol, bicalutamide, bifemelane, birnakalim, bimithil, binospirone, bioxalomycin alpha2, biriperone, bis-benzimidazole A, bis-benzimidazole B, bisantrene, bisaramil, bisaziridinylspermine, bisnafide, bisoprolol, bistramide D, bistramide K, bistratene A, boldine, bopindolol, brefeldin, breflate, brimonidine, bromfenac, bromperidol, bropirimine, bucindolol, budesonide, budipine, budotitane, bunaprolast, bunazosin, butenafine, buthionine sulfoximine, butixocort propionate, cadexomer iodine, calanolide A, calcipotriol, calphostin C, camonagrel, candesartan, candesartan cilexetil, candoxatril, candoxatrilat, capecitabine, capromab, capsaicin, captopril, carbazomycin C, carbetocin, carbovir, carboxamide-amino-triazole, carboxyamidotriazole, carboxymethylated β-1,3-glucan, carperitide, carteolol, carumonam, carvedilol, carvotroline, carzelesin, castanospermine, cebaracetam, cecropin B, cefcapene pivoxil, cefdaloxime pentexil tosilate, cefdinir, cefditoren pivoxil, cefepime, cefetamet, cefetamet pivoxil, cefixime, cefluprenam, cefmnetazole, cefmninox, cefodizime, cefoselis, cefotetan, cefotiam, cefotiam hexetil, cefozopran, cefpimizole, cefpiramide, cefpirome, cefpodoxime proxetil, cefprozil, cefsulodin, cefteram, ceftibuten, ceftriaxone, cefuroxime axetil, celastrol, celikalim, celiprolol, cepacidine A, cericlamine, cerivastatin, ceronapril, certoparin sodium, cetiedil, cetirizine, chloroorienticin A, chloroorienticin B, chloroquinoxaline sulfonamide, cibenzoline, cicaprost, ciclesonide, cicletanine, cicloprolol, cidofovir, cilansetron, cilazapril, cilnidipine, cilobradine, cilostazol, cimetropium bromide, cinitapride, cinolazepam, cioteronel, ciprofibrate, ciprofloxacin, ciprostene, cis-porphyrin, cisapride, cisatracurium besilate, cistinexine, citalopram, citicoline, citreamicin alpha, cladribine, clarithromycin, clausenamide, clebopride, clinafloxacin, clobazam, clobetasone butyrate, clodronic acid, clomethiazole, clopidogrel, clotrimazole, colestimide, colfosceril palmitate, collismycin A, collismycin B, combretastatin A4, complestatin, conagenin, contignasterol, contortrostatin, cosalane, costatolide, cotinine, coumermycin A1, cucumariosid, curacin A, curdlan sulfate, curiosin, cyclazosin, cyclic HPMPC, cyclobenzaprine, cyclobut A, cyclobut G, cyclocapron, cycloplatam, cyclosin, cyclothialidine, cyclothiazomycin, cypemycin, cyproterone, cytarabine ocfosfate, cytochalasin B, dacliximab, dactimicin, daidzein, daidzin, dalfopristin, dalteparin sodium, danaparoid, daphnodorin A, dapiprazole, dapitant, darifenacin, darlucin A, darsidomine, ddUTP, decitabine, deferiprone, deflazacort, dehydrodidemnin B, dehydroepiandrosterone, delapril, delequamine, delfaprazine, delmopinol, delphinidin, deoxypyridinoline, deprodone, depsidomycin, deramciclane, dermatan sulfate, desflurane, desirudin, deslorelin, desmopressin, desogestrel, desoxoarniodarone, detajmium bitartrate, dexifosfamide, dexketoprofen, dexloxiglumide, dexmedetomidine, dexpemedolac, dexrazoxane, dexsotalol, dextrin 2-sulphate, dexverapamil, dezinamide, dezocine, diaziquone, diclofenac digolil, diclofenac potassium, dicranin, didemnin B, didox, dienogest, diethylhomospermine, diethylnorspermine, dihydrexidine, dihydro-5-azacytidine, dimethyl prostaglandin A1, dimethylhomospermine, dimiracetam, dioxamycin, diphencyprone, diphenyl spiromustine, diprafenone, dipropylnorspermine, dirithromycin, discodermolide, disulfuram, ditekiren, docarpamine, docosanol, 1-dofetilide, dolasetron, domitroban, dopexamine, dorzolamide, dosmalfate, dotarizine, doxacurium chloride, doxazosin, doxifluridine, doxofylline, draculin, draflazine, droloxifene, dronabinol, drosperidone, drotaverine acephyllinate, droxicam, ebiratide, ebrotidine, ebselen, ecabapide, ecabet, ecadotril, ecdisteron, echicetin, echistatin, ecomustine, ecteinascidin 722, ecteinascidin 729, ecteinascidin 743, edaravone, edelfosine, edobacomab, edrecolomab, efegatran, eflornithine, efonidipine, egualen, elcatonin, eletriptan, elgodipine, eliprodil, eltenac, emakalim, emedastine, emiglitate, emitefur, emoctakin, enadoline hydrochloride, enalapril, enazadrem, englitazone, enlimomab, enoxacin, enoxaparin sodium, enoximone, entacapone, enterostatin, epoprostenol, epoxymexrenone, epristeride, eprosartan, eptastigmine, erdosteine, ersentilide, ersofermin, erytlritol, esuprone, etanidazole, etanterol, ethacizin, ethinylestradiol, etizolam, etodolac, etoposide phosphate, etrabamine, everninomicin, examorelin, exemestane, fadrozole, faeriefungin, famciclovir, fampridine, fantofarone, faropenem, fasidotril, fasudil, fazarabine, fedotozine, felbamate, fenofibrate, fenoldopam, fenretinide, fenspiride, fenticonazole, fepradinol, ferpifosate sodium, ferristene, ferrixan, ferumoxsil, fexofenadine, flavopiridol, flecamide, flerobuterol, fleroxacin, flesinoxan, flezelastine, flobufen, flomoxef, florfenicol, florifenine, flosatidil, fluasterone, fluconazole, fludarabine, flumazenil, flumecinol, flumequine, flunarizine, fluocalcitriol, fluorodaunorunicin hydrochloride, fluoxetine, R-fluoxetine, S-fluparoxan, flupirtine, flurbiprofen axetil, flurithromycin, fluticasone propionate, flutrimazole, fluvastatin, fluvoxamine, forasartan, forfenimex, formestane, formoterol, formoterol, R,R-fosfomycin, trometamol, fosinopril, fosphenyloin, fostriecin, fotemustine, gabapentin, gadobenic acid, gadobutrol, gadodiamide, gadodiamide-EOB-DTPA, gadolinium texaphyrin, gadoteric acid, gadoteridol, gadoversetamide, galantamine, galdansetron, gallopamil, galocitabine, gamolenic acid, ganirelix, gepirone, gestrinone, girisopam, glaspimod, glaucocalyxin A, glutapyrone, glycopine, glycopril, granisetron, grepafloxacin, halichondrin B, halofantrine, halomon, halopredone, hatomamicin, hatomarubigin A, hatomarubigin B, hatomarubigin C, hatomarubigin D, ibogaine, ibopamine, ibudilast, illimaquinone, ilmofosine, ilomastat, iloperidone, iloprost, imidapril, imidazenil, indinavir, indolidan, indometacin farnesil, indometacin, tropine ester, indoramin, inocoterone, inogatran, inolimomab, interferon alfa, interferon alfa-2a, interferon alfa-2B, interferon alfa-N 1, interferon alfa-N3, interferon β, interferon β-1 A1, interferon β-1B, interferon gamma-1A, interferon gamma-1B, interferon omega, interferon, consensus, interleukin-1, interleukin-1 alpha, interleukin-1 β, interleukin-10, interleukin-11, interleukin-12, interleukin-12, interleukin-15, interleukin-2, interleukin-3, interleukin-4, interleukin-5, interleukin-7, interleukin-8, iobenguane, iobitridol, iodoamiloride, iododoxorubicin, iofratol, iomeprol, iopentol, iopromide, iopyrol, iotriside, ioversol, ioxilan, ipazilide, IpdR, ipenoxazone, ipidacrine, ipomeanol, 4-ipriflavone, ipsapirone, irbesartan, irinotecan, irloxacin, irsogladine, irtemazole, isalsteine, isbogrel, isepamicin, isobengazole, isofloxythepin, isohomohalicondrin B, isopropyl unoprostone, isradipine, itameline, itasetron, itopride, itraconazole, ketoprofen, R-ketoprofen, S-ketorolac, lacidipine, lactitol, lactivicin, laennec, lafutidine, lamelrarin-N triacetate, lamifiban, lamivudine, lamotrigine, lanoconazole, lanperisone, lanreotide, lansoprazole, latanoprost, lateritin, laurocapram, lazabemide, lemefloxacin, lemildipine, leminoprazole, lenercept, lenograstim, lentinan sulfate, leptin, leptolstatin, lercanidipine, lerisetron, lesopitron, letrazuril, letrozole, leucomyzin, leuprorelin, levcromakalim, levetiracetam, levobetaxolol, levobunolol, levobupivacaine, levocabastine, levocamitine, levodropropizine, levofloxacin, levomoprolol, levonorgestrel, levormeloxifene, levosimendan, levosulpiride, linotroban, linsidomine, lintitript, lintopride, liothyronine sodium, lirexapride, lisinopril, lobaplatin, lobucavir, lodoxamide, lombricine, lomefloxacin, lomerizine, lometrexol, lonazolac, lonidamine, loracarbef, loratadine, lorglumide, lornoxicam, losartan, losigamone, losoxantrone, loteprednol, loviride, loxoribine, lubeluzole, lurtotecan, luteinizing hormone, lutetium, luzindole, lydicamycin, lysofylline, lysostaphin, magainin 2 amide, magnolol, mallotochromene, mallotojaponin, malotilate, mangafodipir, manidipine, maniwamycin A, mannostatin A, manumycin E, manumycin F, mapinastine, marimastat, masoprocol, maspin, massetolide, meterelin, methoxatone, methylhistamine, R-alpha, methylinosine monophosphate, methylprednisolone aceponate, methylprednisolone suleptanate, metipamide, metoclopramide, metoprolol, S-metrifonate, mibefradil, michellarnine B, microcolin A, midodrine, mifepristone, miglitol, milacemide, milameline, mildronate, milnacipran, milrinone, miltefosine, minaprine, miokamycin, mipragoside, mirfentanil, mirimostim, mirtazapine, misoprostol, mitoguazone, mitolactol, mitonafide, mitoxantrone, mivacurium chloride, mivazerol, mixanpril, mizolastine, mizoribine, moclobemide, modafinil, moexipril, mofarotene, mofezolac, molgramostim, mometasone, montirelin, mopidamol, moracizine, mosapramine, mosapride, motilide, moxiraprine, moxonidine, nadifloxacin, nadroparin calcium, nafadotride, nafamostat, nafarelin, naftopidil, naglivan, nagrestip, nalmefene, naphterpin, napsagatran, naratriptan, nartograstim, nasaruplase, nateplase, niperotidine, niravoline, nisamycin, nisin, nisoldipine, nitazoxanide, nitecapone, nitrendipine, nitrendipine, S-nitrofurantoin monohydrate, nitrullyn, nizatidine, ofloxacin, okicenone, olanzapine, olopatadine, olprinone, olsalazine, omeprazole, onapristone, ondansetron, ondansetron, R-ontazolast, oracin, otenzepad, oxaliplatin, oxamisole, oxandrolone, oxaprozin, oxaunomycin, oxcarbazepine, oxiconazole, oxiracetam, oxodipine, ozagrel, palauamine, palinavir, palmitoylrhizoxin, pamaqueside, pamicogrel, pamidronic acid, panamesine, panaxytriol, panipenem, panipenum, pannorin, panomifene, pantethine, pantoprazole, parabactin, pamaparin sodium, paroxetine, parthenolide, pazelliptine, pazufloxacin, pefloxacin, pegaspargase, peldesine, pemedolac, pemirolast, penciclovir, pentafuside, pentamidine, pentamorphone, pentigetide, pentosan, pentostatin, pentrozole, perflubron, perfosfamide, pergolide, perindoprilat, perospirone, phenaridine, phenazinomycin, phenserine, phensuccinal, phentolamine mesilate, phenylacetate, phenylalanyl ketoconazole, picenadol, picibanil, picroliv, picumeterol, pidotimod, pilocarpine hydrochloride, pilsicamide, pimagedine, pimilprost, pimobendan, pinacidil, pinocebrin, pioglitazone, pipecuronium bromide, pirarubicin, piretanide, pirfenidone, piritrexim, pirlindole, pirmagrel, pirmenol, pirodavir, pirodomast, piroxicam cinnamate, propagermanium, propentofylline, propionylcamitine, L-propiram, propiram +paracetamol, propiverine, propyl bis-acridone, prostaglandin J2, prostratin, protegrin, protosufloxacin, prulifloxacin, pyrazoloacridine, quazepam, quetiapine, quiflapon, quinagolide, quinapril, quinfamide, quinupristin, raloxifene, raltitrexed, ramatroban, ramipril, ramosetron, ranelic acid, ranitidine bismuth citrate, ranolazine, recainam, regavirumab, relaxin, repirinast, resinferatoxin, reticulon, revipariin sodium, revizinone, ricasetron, ridogrel, rifabutin, rifapentine, rifaximin, rilopirox, riluzole, rimantadine, rimexolone, rimoprogin, riodipine, ripisartan, risedronic acid, rispenzepine, risperidone, ritanserin, ritipenem, ritipenem acoxil, ritolukast, ritonavir, rizatriptan benzoate, rohitukine, rokitamycin, ropinirole, ropivacaine, roquinimex, roxatidine, roxindole, roxithromycin, rubiginone B1, ruboxyl, rufloxacin, rupatidine, ruzadolane, safingol, safironil, saintopin, salbutamol, R-salmeterol, salmeterol, R-sainacedin, sameridine, sampatrilat, sanfetrinem, saprisartan, sapropterin, saquinavir, sarcophytol A sargramostim, sarpogrelate, saruplase, saterinone, satigrel, satumomab pendetide, selegiline, selenium thiosemicarbazone, sematilide, semduramicin, semotiadil, semustine, sermorelin, sertaconazole, sertindole, sertraline, setiptiline, sevirumab, sevoflurane, sezolamide, silipide, silteplase, simendan, simvastatin, sinitrodil, sinnabidol, sipatrigine, sirolimus, sizofuran, somatomedin B, somatomedin C, somatrem, somatropin, sonermin, stalol, staurosporine, stavudine, stepronin, stipiamide, stiripentol, stobadine, succibun, sucralfate, sulfasalazine, sulfmosine, sulfoxamine, sulopenem, sultamicillin, sultopride, sulukast, sumatriptan, symakalim, tandospirone, tapgen, taprostene, tasosartan, tazanolast, tazarotene, teicoplanin, telenzepine, tellurapyrylium, telmesteine, telmisartan, temocapril, temoporfin, temozolomide, tenidap, teniposide, tenosal, tenoxicam, tepirindole, tepoxalin, terazosin, terbinafine, terfenadine, terflavoxate, terguride, terlakiren, terlipressin, terodiline, tertatolol, testosterone buciclate, tetrachlorodecaoxide, tetrazomine, thaliblastine, thalidomide, thiocoraline, thiofedrine, thiomarinol, thioperamide, thyroid stimulating hormone, tiagabine, tianeptine, tiapafant, tibolone, ticlopidine, tienoxolol, tilisolol, tilnoprofen arbamel, tiludronic acid, tinzaparin sodium, tiotropium bromide, tipredane, tiqueside, tirandalydigin, tirapazamine, tirilazad, tirofiban, tiropramide, topsentin, torasemide, toremifene, tosufloxacin, trafermin, trandolapril, traxanox, tretinoin, tretinoin tocoferil, triacetyluridine, tricaprilin, trichohyalin, trichosanthin, alpha, triciribine, trientine, triflavin, trimegestone, triptorelin, troglitazone, trombodipine, tropisetron, trospectomycin, trovafloxacin, trovirdine, tucaresol, tulobuterol, tylogenin, urapidil, uridine triphosphate, valaciclovir, valproate magnesium, valproate semisodium, valsartan, vamicamide, vanadeine, vaminolol, vapreotide, variolin B, velaresol, venlafaxine, veramine, verapamil, S-verdins, veroxan, verteporfin, vesnarinone, vexibinol, vigabatrin, vinbumine citrate, vinburnine resinate, vinconate, vinorelbine, vinpocetine, vinpocetine citrate, vintoperol, vinxaltine, voriconazole, vorozole, voxergolide, xemilofiban, ximoprofen, yangambin, zabicipril, zacopride, zacopride, R-zafirlukast, zalcitabine, zaleplon, zalospirone, zaltoprofen, zanamivir, zankiren, zanoterone, zatebradine, zatosetron, zenarestat, zeniplatin, zifrosilone, zilascorb, zileuton, zinostatin stimalamer, ziprasidone, zoledronic acid, zolmitriptan, zolpidem, zonisamide, zopiclone, zopiclone, S-zopolrestat, zotepine.

When antibacterial activity is a desired property of the disclosed films, fibers, or beads, one or more of the following can be an used as an adjunct ingredient. Further examples of suitable antibacterial agents include, but are not limited to, acedapsone, acetosulfone sodium, alamecin, alexidine, amdinocillin, amdinocillin pivoxil, amicycline, amifloxacin, amifloxacin mesylate, amikacin, amikacin sulfate, aminosalicylic acid, aminosalicylate sodium, amoxicillin, amphomycin, ampicillin, ampicillin sodium, apalcillin sodium, apramycin, aspartocin, astromicin sulfate, avilamycin, avoparcin, azithromycin, azlocillin, azlocillin sodium, bacampicillin hydrochloride, bacitracin, bacitracin methylene disalicylate, bacitracin zinc, bambermycins, benzoylpas calcium, berythromycin, betamicin sulfate, biapenem, biniramycin, biphenamine hydrochloride, bispyrithione magsulfex, butikacin, butirosin sulfate, capreomycin sulfate, carbadox, carbenicillin disodium, carbenicillin indanyl sodium, carbenicillin phenyl sodium, carbenicillin potassium, carumonam sodium, cefaclor, cefadroxil, cefamandole, cefamandole nafate, cefamandole sodium, cefaparole, cefatrizine, cefazaflur sodium, cefazolin, cefazolin sodium, cefbuperazone, cefdinir, cefepime, cefepime hydrochloride, cefetecol, cefixime, cefmenoxime hydrochloride, cefmetazole, cefmetazole sodium, cefonicid monosodium, cefonicid sodium, cefoperazone sodium, ceforanide, cefotaxime sodium, cefotetan, cefotetan disodium, cefotiam hydrochloride, cefoxitin, cefoxitin sodium, cefpimizole, cefpimizole sodium, cefpiramide, cefpiramide sodium, cefpirome sulfate, cefpodoxime proxetil, cefprozil, cefroxadine, cefsulodin sodium, ceftazidime, ceftibuten, ceftizoxime sodium, ceftriaxone sodium, cefuroxime, cefuroxime axetil, cefuroxime pivoxetil, cefuroxime sodium, cephacetrile sodium, cephalexin, cephalexin hydrochloride, cephaloglycin, cephaloridine, cephalothin sodium, cephapirin sodium, cephradine, cetocycline hydrochloride, cetophenicol, chloramphenicol, chloramphenicol palmitate, chloramphenicol pantothenate complex, chloramphenicol sodium succinate, chlorhexidine phosphanilate, chloroxylenol, chlortetracycline bisulfate, chlortetracycline hydrochloride, cinoxacin, ciprofloxacin, ciprofloxacin hydrochloride, cirolemycin, clarithromycin, clinafloxacin hydrochloride, clindamycin, clindamycin hydrochloride, clindamycin palmitate hydrochloride, clindamycin phosphate, clofazimine, cloxacillin benzathine, cloxacillin sodium, cloxyquin, colistimethate sodium, colistin sulfate, coumermycin, coumermycin sodium, cyclacillin, cycloserine, dalfopristin, dapsone, daptomycin, demeclocycline, demeclocycline hydrochloride, demecycline, denofungin, diaveridine, dicloxacillin, dicloxacillin sodium, dihydrostreptomycin sulfate, dipyrithione, dirithromycin, doxycycline, doxycycline calcium, doxycycline fosfatex, doxycycline hyclate, droxacin sodium, enoxacin, epicillin, epitetracycline hydrochloride, erythromycin, erythromycin acistrate, erythromycin estolate, erythromycin ethylsuccinate, erythromycin gluceptate, erythromycin lactobionate, erythromycin propionate, erythromycin stearate, ethambutol hydrochloride, ethionamide, fleroxacin, floxacillin, fludalanine, flumequine, fosfomycin, fosfomycin tromethamine, fumoxicillin, furazolium chloride, furazolium tartrate, fusidate sodium, fusidic acid, gentamicin sulfate, gloximonam, gramicidin, haloprogin, hetacillin, hetacillin potassium, hexedine, ibafloxacin, imipenem, isoconazole, isepamicin, isoniazid, josamycin, kanamycin sulfate, kitasamycin, levofuraltadone, levopropylcillin potassium, lexithromycin, lincomycin, lincomycin hydrochloride, lomefloxacin, lomefloxacin hydrochloride, lomefloxacin mesylate, loracarbef, mafenide, meclocycline, meclocycline sulfosalicylate, megalomicin potassium phosphate, mequidox, meropenem, methacycline, methacycline hydrochloride, methenamine, methenamine hippurate, methenamine mandelate, methicillin sodium, metioprim, metronidazole hydrochloride, metronidazole phosphate, mezlocillin, mezlocillin sodium, minocycline, minocycline hydrochloride, mirincamycin hydrochloride, monensin, monensin sodiumr, nafcillin sodium, nalidixate sodium, nalidixic acid, natainycin, nebramycin, neomycin palmitate, neomycin sulfate, neomycin undecylenate, netilmicin sulfate, neutramycin, nifuiradene, nifuraldezone, nifuratel, nifuratrone, nifurdazil, nifurimide, nifiupirinol, nifurquinazol, nifurthiazole, nitrocycline, nitrofurantoin, nitromide, norfloxacin, novobiocin sodium, ofloxacin, onnetoprim, oxacillin sodium, oximonam, oximonam sodium, oxolinic acid, oxytetracycline, oxytetracycline calcium, oxytetracycline hydrochloride, paldimycin, parachlorophenol, paulomycin, pefloxacin, pefloxacin mesylate, penamecillin, penicillin G benzathine, penicillin G potassium, penicillin g procaine, penicillin g sodium, penicillin V, penicillin V benzathine, penicillin V hydrabamine, penicillin V potassium, pentizidone sodium, phenyl aminosalicylate, piperacillin sodium, pirbenicillin sodium, piridicillin sodium, pirlimycin hydrochloride, pivampicillin hydrochloride, pivampicillin pamoate, pivampicillin probenate, polymyxin B sulfate, porfiromycin, propikacin, pyrazinamide, pyrithione zinc, quindecamine acetate, quinupristin, racephenicol, ramoplanin, ranimycin, relomycin, repromicin, rifabutin, rifametane, rifamexil, rifamide, rifampin, rifapentine, rifaximin, rolitetracycline, rolitetracycline nitrate, rosaramicin, rosaramicin butyrate, rosaramicin propionate, rosaramicin sodium phosphate, rosaramicin stearate, rosoxacin, roxarsone, roxithromycin, sancycline, sanfetrinem sodium, sarmoxicillin, sarpicillin, scopafungin, sisomicin, sisomicin sulfate, sparfloxacin, spectinomycin hydrochloride, spiramycin, stallimycin hydrochloride, steffimycin, streptomycin sulfate, streptonicozid, sulfabenz, sulfabenzamide, sulfacetamide, sulfacetamide sodium, sulfacytine, sulfadiazine, sulfadiazine sodium, sulfadoxine, sulfalene, sulfamerazine, sulfameter, sulfamethazine, sulfamethizole, sulfamethoxazole, sulfamonomethoxine, sulfamoxole, sulfanilate zinc, sulfanitran, sulfasalazine, sulfasomizole, sulfathiazole, sulfazamet, sulfisoxazole, sulfisoxazole acetyl, sulfisboxazole diolamine, sulfomyxin, sulopenem, sultamricillin, suncillin sodium, talampicillin hydrochloride, teicoplanin, temafloxacin hydrochloride, temocillin, tetracycline, tetracycline hydrochloride, tetracycline phosphate complex, tetroxoprim, thiamphenicol, thiphencillin potassium, ticarcillin cresyl sodium, ticarcillin disodium, ticarcillin monosodium, ticlatone, tiodonium chloride, tobramycin, tobramycin sulfate, tosufloxacin, trimethoprim, trimethoprim sulfate, trisulfapyrimidines, troleandomycin, trospectomycin sulfate, tyrothricin, vancomycin, vancomycin hydrochloride, virginiamycin, and zorbamycin. Penicillin G, which is used as an antibacterial agent for infections including pneumonia, meningitis, and skin, bone, joint, stomach, blood, and heart valve infections, is a particular example suitable for use herein. tazobactum, sold under the trade names ZOSYN™ and TAZOCIN™, ceftrioxone, sold under the trade name ROCEPHIN™, and metronidazol, sold under the trade name FLAGYL™, are also used to treat bacterial infections and are further examples of suitable compounds that can be used to prepare the disclosed ionic liquids.

When antiviral activity is a desired property of the disclosed films, fibers or beads, one or more of the following antivirals can be used as an adjunct ingredient. Examples of suitable antiviral actives include, but are not limited to, acemannan, acyclovir, acyclovir sodium, adefovir, alovudine, alvircept sudotox, amantadine hydrochloride, aranotin, arildone, atevirdine mesylate, pyridine, cidofovir, cipamfylline, cytarabine hydrochloride, delavirdine mesylate, desciclovir, didanosine, disoxaril, edoxudine, enviradene, enviroxime, famciclovir, famotine hydrochloride, fiacitabine, fialuridine, fosarilate, foscarnet sodium, fosfonet sodium, ganciclovir, ganciclovir sodium, idoxuridine, kethoxal, lamivudine, lobucavir, memotine hydrochloride, methisazone, nevirapine, penciclovir, pirodavir, ribavirin, rimantadine hydrochloride, saquinavir mesylate, somantadine hydrochloride, sorivudine, statolon, stavudine, tilorone hydrochloride, trifluridine, valacyclovir hydrochloride, vidarabine, vidarabine phosphate, vidarabine sodium phosphate, viroxime, zalcitabine, zidovudine, zinviroxime, and Tamiflu.

When pesticidal activity is a desired property of the disclosed films, fibers, or beads, one or more of the following pesticides can be used as an adjunct ingredient. Included within the meaning of "pesticide" are insecticides and fungicides. Examples of suitable pesticides include, but are not limted to, carfentrazone-ethyl, sulfentrazone, clomazone, diclofop-methyl, oxamyl propargite, prosulfuron, pyridate, pyriftalid, S-metolachlor, simazine, terbuthylazine, terbutryn, triasulfuron, trifloxysulfuron, trinexapac-ethyl, ametryn, atrazine, benoxacor, bifenthrin, butafenacil, choline azide, chlortoluron, cinosulfuron, clodinafop, cloquintocet, DEET, desmetryn, dicamba, dimethachlor, dimethametryn, DTPA NaFe, EDDHA NaFe, fenclorim, flumetralin, fluometuron, fluthiacetmethyl, halosulfuron, isoproturon, metobromuron, metolachlor, norflurazon, oxasulfuron, piperophos, pretilachlor, primisulfuron, prometryn, propaquizafop, acibenzolar-s-methyl, chlorothalonil, cyproconazole, cyprodinil, difenoconazole, fenpropidin, fenpropimorph, furalaxyl, metalaxyl, metalaxyl-m, oxadixyl, penconazole, propiconazole, pyrifenox, thiabendazol, abamectin, bromopropylate, cypermethrin, cypermethrin high-cis, cyromazine, diafenthiuron, diazinon, dichlorvos, disulfoton, emamectinbenzoate, fenoxycarb, formothion, furathiocarb, lufenuron, methidathion, permethrine, codlemone, phosphamidon, profenofos, pymetrozine, quinalphos, terrazole, thiamethoxam, thiocyclam, thiometon, triallate, trifloxystrobin, vinclozolin, zetacypermethrin, and the like. Prohexadione is a FDA approved reduced risk fungicide and is also useful for the disclosed ionic liquids. Further examples of suitable pesticides can be found in The Pesticide Manual, 11$^{th}$ Edition, British Crop Protection Council, 1997, which is incorporated by reference herein at least for its teaching of pesticides.

When herbicidal activity is a desired property of the disclosed films, fibers or beads, one or more of the ions in the disclosed ionic liquids can be a herbicide. Examples of suitable herbicides include, but are not limited to, carfentrazone, imazapyr, benefin, acifluorfen, and 2-[2-chloro-3-(2,2,2-trifluoroethoxymethyl)-4-methylsulfonylbenzoyl]-cyclohexane-1.

Other suitable herbicides include inhibitors of the biosynthesis of branched amino acids such as ethoxysulfuron, flumetsulam, halosulfuron, imazamox, imazapyr, imazaquin, imazethapyr, metosulam, nicosulfuron, primisulfuron, prosulfuron, rimsulfuron, thifensulfuron-methyl, triflusulfuron, N-[(4,6-dimethoxypyrimidin-2-yl)aminocarbonyl]-2-dimethylaminocarbonyl-5-formylaminobenzenesulfonamide (Foramsulfuron), and the like. Still further, suitable herbicides include inhibitors of the photosynthesis electron transport such as ametryne, atrazine, bromoxynil, cyanazine, diuron, hexazinone, metribuzin, pyridate, terbuthylazine, and the like. In yet further examples, suitable herbicides for the disclosed ionic liquids include synthetic auxins such as copyralid, dicamba, diflufenzopyr, fluoroxypyr, and the like. Inhibitors of fatty acid biosynthesis, such as butylate, EPTC, fenoxaprop-P-ethyl, and the like, can also be used in the disclosed ionic liquid compositions. In other examples, suitable herbicides can include inhibitors of cell division such as acetochlor, alachlor, dimethenamid, flufenacet, mefenacet, metolachlor, S-metolachlor, thenylchlor, and the like. In still other examples, the herbicide can be an inhibitor of protoporphyrinogen oxidase, such as fluthiacet-methyl, carfentrazone-ethyl, and the like. Inhibitors of hydroxyphenylpyruvate dioxygenase, such as isoxaflutole, mesotrione, sulcotrione, 4-(4-trifluoromethyl-2-methylsulfonylbenzoyl)-5-hydroxy-1-methyl-3-methylpyrazole, and the like, can also be used. Further examples of suitable herbicides include, but are not limited to, glyphosate, pendimethalin, trifluralin, asulam, triaziflam, diflufenican, glufosinate-ammonium, and the like. Clofencet, fluoroxpyr, mesosulfuron, diflufenzopyr are further examples of suitable herbicides and they are FDA approved.

In addition to the pharmaceutical, antibacterial, antiviral, pesticidal, and herbicidal ingredients disclosed herein, other compounds that are suitable as adjunct ingredients include the food additives Allura Red AC (FD&C Red No. 40), Tartrazine (FD&C Yellow No. 5), Indigotine (FD&C Blue No. 2), Erythrosine (FD&C Red No. 3), and Sunset Yellow (FD&C Yellow No. 6), which are FDA-approved color additives for food use. Further, nutraceuticals such as fatty acids, cholesterols, vitamins, minerals, and trace elements can be adjunct ingredients.

Agrochemicals, neutraceuticals, oil dispersant can also been used as an adjunct ingredients. Other suitable active ingredients that can be used as adjunct ingredients herein are disclosed in U.S. Application 20070093462, which is incorporated by reference herein in its entirety for its teachings of active substances.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A process for preparing chitin films, fibers, or beads, comprising:
   a) contacting an ionic liquid with a chitinous biomass to form a residue and a chitin comprising solution, wherein the ionic liquid comprises a cation and an anion, wherein the cation is 3-ethyl-1-methyl-1H-imidazol-3-ium and the anion is a $C_{1-8}$ carboxylate;
   b) adding a coagulant to the solution formed in step (a) and casting the chitin comprising solution into a film, a fiber, or a bead.

2. The process according to claim 1, further comprising adding an adjunct ingredient to the chitin comprising solution, wherein the adjunct ingredient is one or more pharmaceuticals, herbicides, insecticides, food ingredient, antibiotic, fatty acid, vitamin, or mineral.

3. The process according to claim 1, wherein the ionic liquid is 3-ethyl-1-methyl-1H-imidazol-3-ium acetate.

4. The process according to claim 1, wherein the chitinous biomass is chosen from practical grade chitin, shrimp shells, or crab shells.

5. The process according to claim 1, wherein the chitinous biomass is dissolved or dispersed in the ionic liquid at a temperature of from about 70° C. to about 130° C.

6. The process according to claim 1, wherein the coagulant is chosen from water or a $C_1$-$C_4$ linear or branched alcohol.

7. The process according to claim 1, wherein the coagulant is a mixture of water and one or more $C_1$-$C_4$ linear or branched alcohols.

8. The process according to claim 1, wherein a co-solvent is added in step (a).

9. The process according to claim 8, wherein the co-solvent is dimethylsulfoxide, DMSO.

10. A process for preparing chitin films, comprising:
 a) dissolving or dispersing a source of chitin in an first ionic liquid to form a first solution wherein the ionic liquid comprises a cation and an anion, wherein the cation is 3-ethyl-1-methyl-1H-imidazol-3-ium and the anion is a $C_{1-8}$ carboxylate;
 b) separating any undissolved material to form a second solution;
 c) adding a first coagulant to the second solution to form regenerated chitin;
 d) isolating the regenerated chitin;
 e) redissolving the regenerated chitin in a second ionic liquid; and
 f) adding a second coagulant and casting the regenerated chitin from step (e) into a film, a fiber, or a bead.

11. The process according to claim 10, wherein the source of chitin is chosen from practical grade chitin, shrimp shells, or crab shells.

12. The process according to claim 10, wherein the source of chitin is dissolved or dispersed in the organic solvent or first ionic liquid at a temperature of from about 0° C. to about 50° C.

13. The process according to claim 10, wherein in step (b) the second solution is free of undissolved solids.

14. The process according to claim 10, wherein the first coagulant is chosen from water or a $C_1$-$C_4$ linear or branched alcohol.

15. The process according to claim 10, wherein the first coagulant is a mixture of water and one or more $C_1$-$C_4$ linear or branched alcohols.

16. The process according to claim 10, wherein the regenerated chitin in step (d) is isolated by filtration or centrifugation.

17. The process according to claim 10, wherein the second ionic liquid is 3-ethyl-1-methyl-1H-imidazol-3-ium acetate.

18. The process according to claim 10, wherein the regenerated chitin is dissolved or dispersed in step (e) in the second ionic liquid at a temperature of from about 70° C. to about 130° C.

19. The process according to claim 10, wherein the second coagulant is chosen from water or a $C_1$-$C_4$ linear or branched alcohol.

20. The process according to claim 10, wherein the second coagulant is a mixture of water and one or more $C_1$-$C_4$ linear or branched alcohols.

21. A mixture of chitinous biomass and an ionic liquid, wherein the ionic liquid comprises a cation and an anion, wherein the cation is 3-ethyl-1-methyl-1H-imidazol-3-ium and the anion is a $C_{1-8}$ carboxylate.

22. The mixture of claim 21, wherein the ionic liquid is 3-ethyl-1-methyl-1H-imidazol-3-ium acetate.

23. The mixture of claim 22, wherein the chitinous biomass is selected from the group consisting of practical grade chitin, shrimp shells, and crab shells.

24. A chitin fiber, wherein the fiber is pulled from a mixture of crustacean shells and the ionic liquid is 3-ethyl-1-methyl-1H-imidazol-3-ium acetate.

25. The mixture of claim 21, further comprising an adjunct ingredient, wherein the adjunct ingredient is one or more of pharmaceutical, herbicide, insecticide, food ingredient, antibiotic, fatty acid, vitamin, or mineral.

\* \* \* \* \*